(12) United States Patent
Shi et al.

(10) Patent No.: US 11,490,856 B2
(45) Date of Patent: Nov. 8, 2022

(54) METHOD AND A SYSTEM FOR ANALYZING NEUROPHARMACOLOGY OF A DRUG

(71) Applicant: City University of Hong Kong, Kowloon (HK)

(72) Inventors: Peng Shi, Kowloon (HK); Xin Wang, Kowloon (HK); Xudong Lin, Kowloon (HK)

(73) Assignee: City University of Hong Kong, Kowloon (HK)

( * ) Notice: Subject to any disclaimer, the term of this patent is extended or adjusted under 35 U.S.C. 154(b) by 1094 days.

(21) Appl. No.: 16/127,471

(22) Filed: Sep. 11, 2018

(65) Prior Publication Data

US 2020/0077947 A1    Mar. 12, 2020

(51) Int. Cl.
*A61B 5/00* (2006.01)
*G06T 7/00* (2017.01)
*G06K 9/62* (2022.01)
*G16H 30/40* (2018.01)

(52) U.S. Cl.
CPC .......... *A61B 5/4848* (2013.01); *A61B 5/0042* (2013.01); *A61B 5/0071* (2013.01); *A61B 5/7267* (2013.01); *G06K 9/6218* (2013.01); *G06T 7/0014* (2013.01); *G16H 30/40* (2018.01); *A61B 2503/40* (2013.01); *A61B 2503/42* (2013.01); *A61B 2576/00* (2013.01); *G06T 2207/10056* (2013.01); *G06T 2207/20024* (2013.01); *G06T 2207/20081* (2013.01); *G06T 2207/30016* (2013.01)

(58) Field of Classification Search
CPC combination set(s) only.
See application file for complete search history.

(56) References Cited

U.S. PATENT DOCUMENTS

2016/0162652 A1* 6/2016 Siekmeier ............. G16H 50/50
706/46
2017/0071522 A1* 3/2017 Parsey ................ A61B 5/0042

OTHER PUBLICATIONS

G. Bruni et al., "Zebrafish Behavioral Profiling Identifies Multitarget Antipsychotic-Like Compounds", Nature Chemical Biology 12,559 (2016).
J. Rihel et al., "Zebrafish Behavioral Profiling Links Drugs to Biological Targets and Rest/Wake Regulation", Science 327, 348 (2010).

* cited by examiner

*Primary Examiner* — Brenda C Bernardi
(74) *Attorney, Agent, or Firm* — Renner Kenner Greive Bobak Taylor & Weber

(57) ABSTRACT

A method for analyzing neuropharmacology of a drug, including the steps of providing a set of brain activity maps representing changes of a brain activity of a living species under an influence of a plurality of known drugs each consisting of a known chemical structure; clustering the set of brain activity maps to form a plurality of functional classifiers; and classifying a brain activity map associated with a chemical compound using the functional classifiers so as to predict a neuropharmacology of the chemical compound.

41 Claims, 42 Drawing Sheets
(42 of 42 Drawing Sheet(s) Filed in Color)

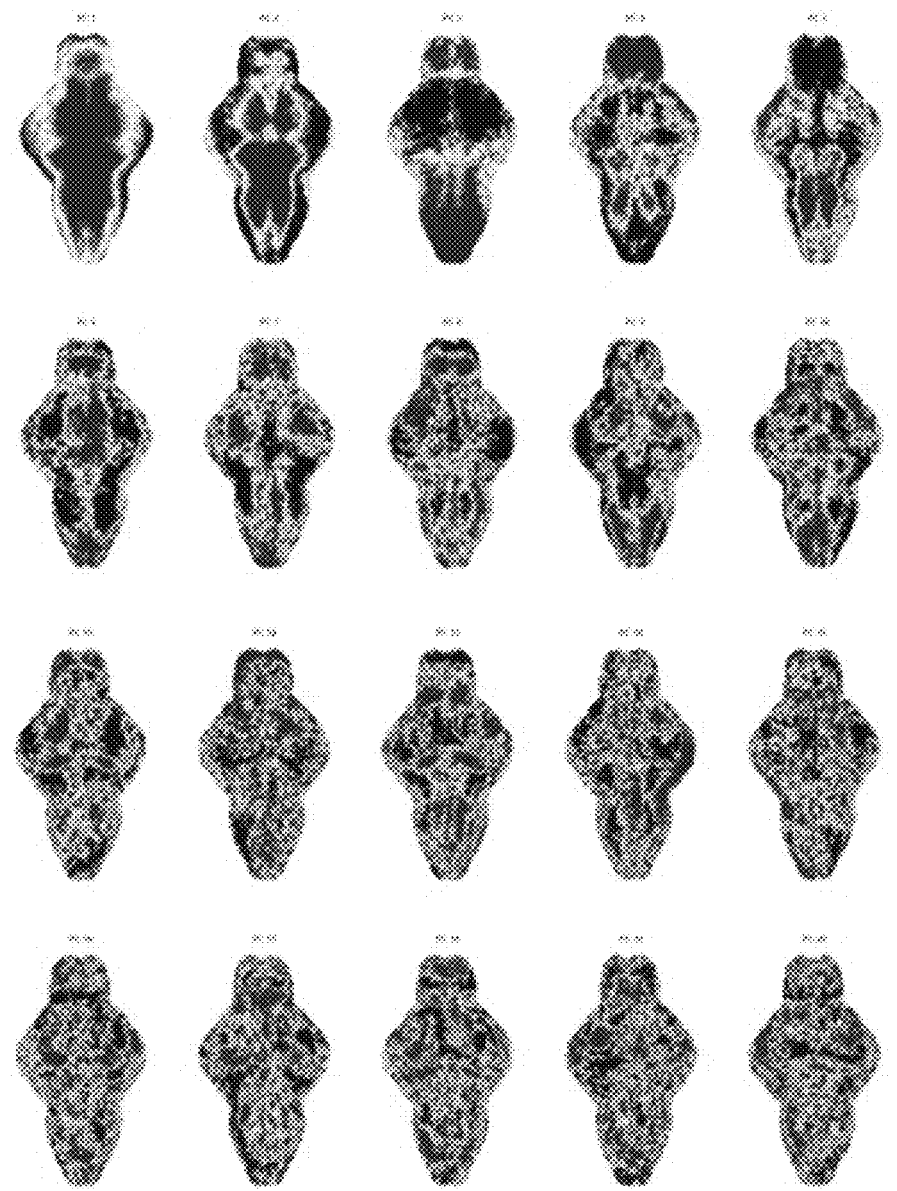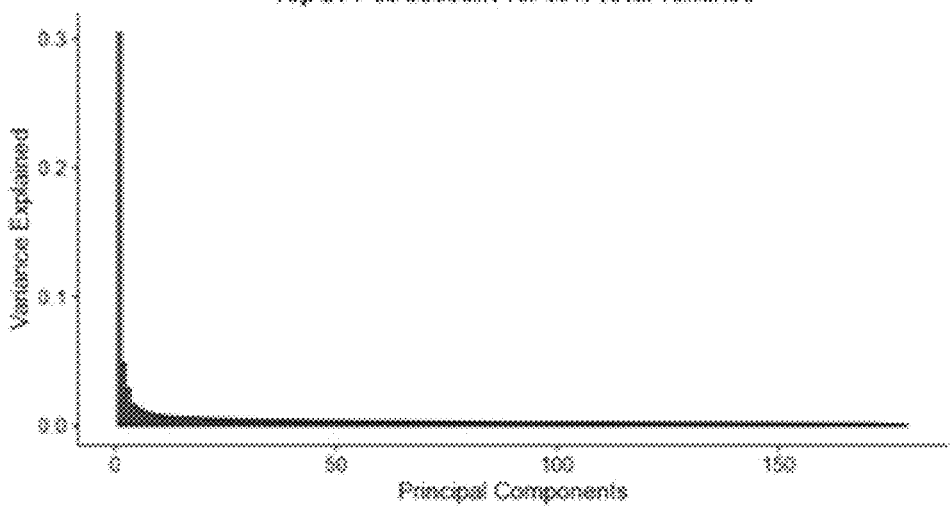
FIG. 16

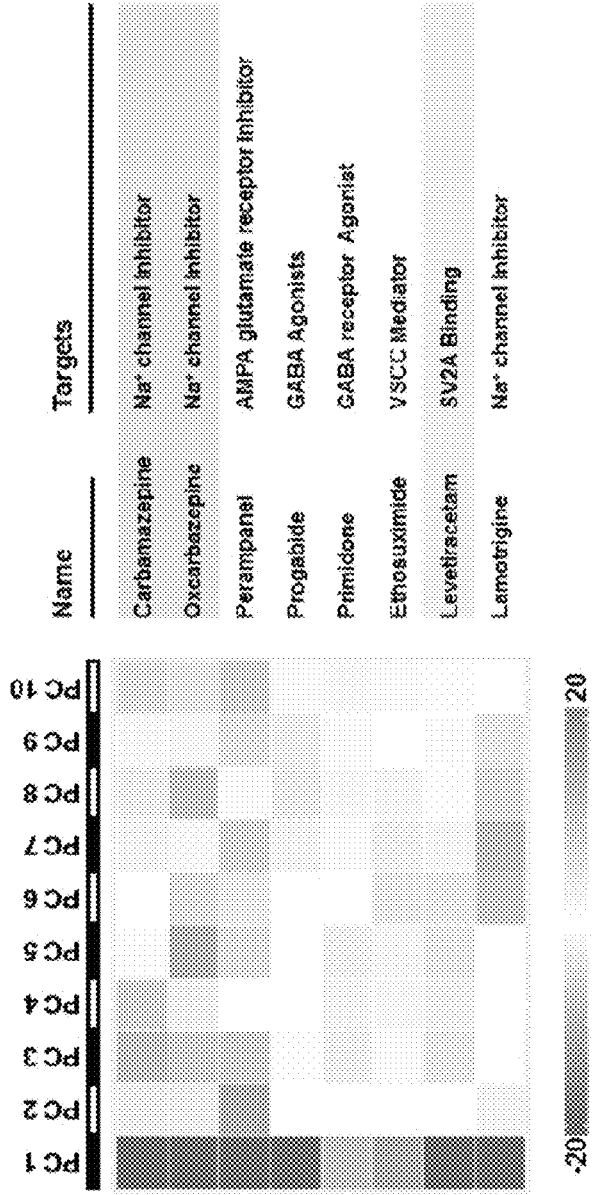
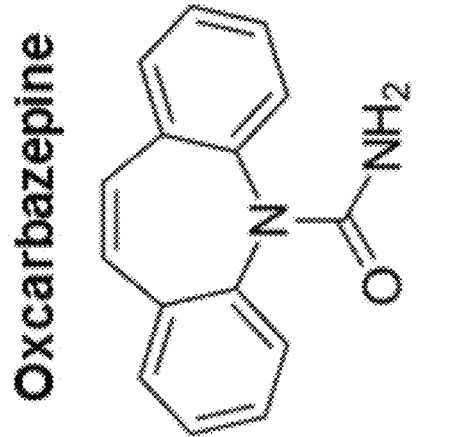
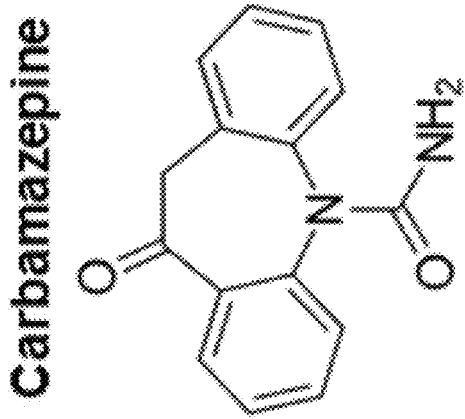
FIG. 27

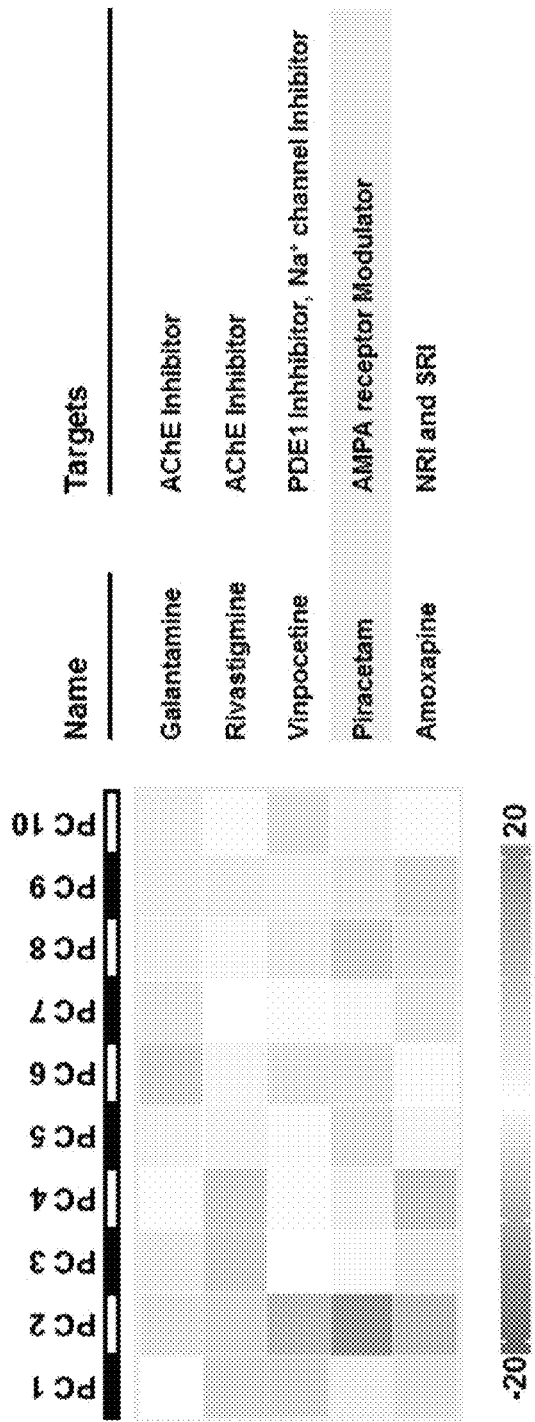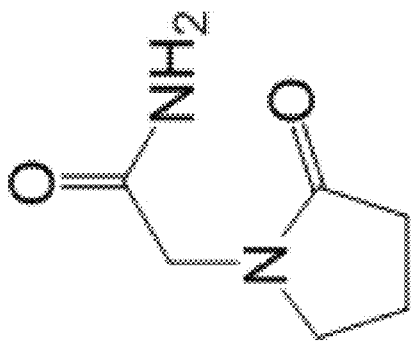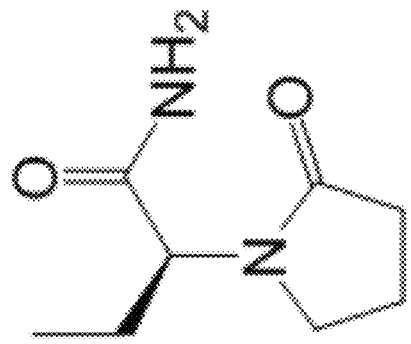
FIG. 28

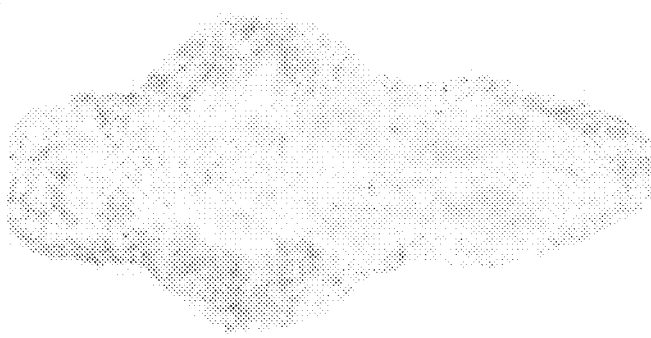
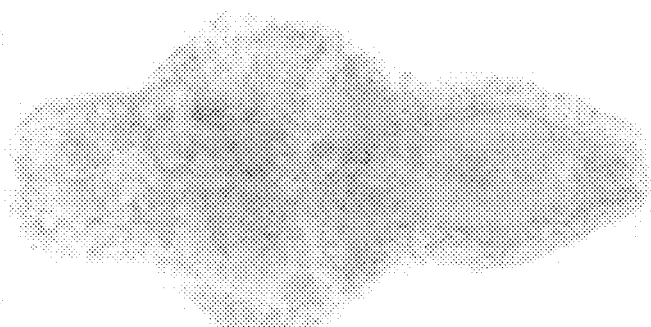
FIG. 31

FIG. 32

| Rank | Compound Name | Targets |
|---|---|---|
| 1 | Volinanserin | 5-HT2A receptor Inhibitor |
| 2 | Sb 216763 | GSK3 inhibitor |
| 3 | Picamilone | GABA prodrug |
| 4 | Sazetidine A | ACh partial Agonist |
| 5 | Gaboxadol | GABAA receptor Agonist |
| 6 | AR-A014418 | GSK3 Inhibitor |
| 7 | IOX1 | 2OG oxygenase Inhibitor |
| 8 | Tubastatin A | HDAC6 Inhibitor |
| 9 | TWS119 | GSK3 Inhibitor |
| 10 | Tabimorelin | Growth hormone secretagogue |
| 11 | GYKI 52466 | AMPA Modulator |
| 12 | Rotundine | D1/D2 Dopaminergic receptors Inhibitor |
| 13 | CI-994 | HDAC Inhibitor |
| 14 | ING-135 | GSK3 Inhibitor |
| 15 | Yangonin | CB1 receptor Ligand |
| 16 | GYKI 53655 | AMPA Modulator |
| 17 | NNC-711 | GABA uptake Inhibitor, Anticonvulsant |
| 18 | Fanapanel | AMPA Modulator |
| 19 | CX-614 | Ampakine, Antidepressant |
| 20 | P7C3 | Neuroprotective |
| 21 | 7,8-Dihydroxyflavone | TrkB Agonist |
| 22 | AL-108 | Neuroprotective |
| 23 | PNU-120596 | positive allosteric a7 ACh Modulator |
| 24 | Sumanirole | D2 receptor Agonist |
| 25 | Piperlongumine | Inhibitor of A-beta production, Natural product |
| 26 | YC-S-169 | HDAC Inhibitor |
| 27 | Varenicline | ON |
| 28 | SKF 89976A | GABA Modulator |
| 29 | Roscovitine | CDK5 Inhibitor |
| 30 | LM22A-4 | BDNF mimetics |
| 31 | Cytisine | Nicotinic acetylcholine receptor Agonist |
| 32 | TCS 1205 | GABAA a2 Agonist and GABAA a1 partial Agonist |
| 33 | BIMU-8 | 5-HT4 receptor selective Agonist |
| 34 | CP-154,526 | CRHR1 Inhibitor |
| 35 | Palmatine | AChE Inhibitor, alkaloid |
| 36 | DU-14 | Steroid sulfatase Inhibitor |
| 37 | FG-4592 | HIF a prolyl hydroxylase Inhibitor |
| 38 | Cytidine | Memory Enhancer |
| 39 | CX-646 | Ampakine |
| 40 | LM22A-3 | BDNF mimetics |
| 41 | Safinamide | MAOI |
| 42 | PF 4778574 | AMPA Modulator |
| 43 | Famprofazone | NSAID |
| 44 | Nefiracetam | GABAergic, ACnergic, MNAergic Modulator |
| 45 | Harmane | MAOI |
| 46 | Nociceptin | Neuropeptide |
| 47 | Kavain | Na+ and Ca2+ channels Inhibitor |
| 48 | BIX-01294 | HKMT Inhibitor |
| 49 | Baicalin | prolyl endopeptidase Inhibitor |
| 50 | Ampalex | Ampakine |
| 51 | Salidroside | Anxiolytic |

FIG. 33

| Rank | Drug Name | Mechanism of Action & Targets |
|---|---|---|
| 1 | Volinanserin | 5-HT2A receptor inhibitor |
| 2 | SB 216763 | GSK3 inhibitor |
| 3 | Pikamilone | GABA prodrug |
| 4 | Sazetidine A | ACh partial Agonist |
| 5 | Gaboxadol | GABAA receptor Agonist |
| 6 | AR-A014418 | GSK3 inhibitor |
| 7 | IOX1 | 2OG oxygenase inhibitor |
| 8 | Tubastatin A | HDAC6 inhibitor |
| 9 | TWS119 | GSK-3β inhibitor |
| 10 | Tabimorelin | Growth hormone secretagogue |
| 11 | GYKI-52466 | AMPA Modulator |
| 12 | Trimethadione | T-type Ca2+ Channel inhibitor |
| 13 | Rotundine | D1/D2 Dopaminergic receptors inhibitor |
| 14 | Tacedinaline | HDAC Inhibitor |
| 15 | ING-135 | GSK3 inhibitor |
| 16 | Stiripentol | GABA Modulator |
| 17 | Yangonin | CB1 receptor Ligand |
| 18 | GYKI-53655 | AMPA Modulator |
| 19 | Phenytoin | Na+ Channel inhibitor |
| 20 | NNC 711 | GABA uptake inhibitor, Anticonvulsant |
| 21 | Fanapanel | AMPA Modulator |
| 22 | CX-614 | Ampakine, Antidepressant |
| 23 | P7C3 | Neuroprotective |
| 24 | 7,8-Dihydroxyflavone | TrkB agonist |
| 25 | AL-108 | Neuroprotective |
| 26 | PNU-120596 | positive allosteric α7 ACh modulator |
| 27 | Methsuximide | VGCC Modulator |
| 28 | Sumanirole | D2 receptor Agonist |
| 29 | Piperlongumine | inhibitor of A-beta production, Natural product |
| 30 | YC-8-169 | HDAC3 inhibitor |
| 31 | Vanoxerine | DRI |
| 32 | SKF 89976A | GABA uptake inhibitor |
| 33 | γ-Aminobutyric acid | GABA Modulator |
| 34 | Roscovitine | CDK5 inhibitor |
| 35 | LM22A-4 | BDNF mimetics |
| 36 | Cytisine | Nicotinic acetylcholine receptor Agonist |
| 37 | TCS 1205 | GABAA α3 agonist and GABAA α1 partial Agonist |
| 38 | BIMU-8 | 5-HT4 receptor selective Agonist |
| 39 | CP-154,526 | CRHR1 inhibitor |
| 40 | Palmatine | AChE inhibitor, alkaloid |
| 41 | DU-14 | Steroid sulfatase inhibitor |
| 42 | FG-4592 | HIF α prolyl hydroxylase inhibitor |
| 43 | Cytidine | Memory Enhancer |
| 44 | CX-546 | Ampakine |
| 45 | LM22A-3 | BDNF mimetics |
| 46 | Safinamide | MAOI |
| 47 | PF 4778574 | AMPA Modulator |
| 48 | Famprofazone | NSAID |
| 49 | Nefiracetam | GABAergic, AChnergic, MNAergic Modulator |
| 50 | Harmane | MAO Inhibitor |
| 51 | Nociceptin | Neuropeptide |
| 52 | Kavain | Na+ and Ca2+ channels inhibitor |
| 53 | BIX-01294 | HKMT inhibitor |
| 54 | Baicalin | prolyl endopeptidase inhibitor |
| 55 | Ampalex | Ampakine |
| 56 | Salidroside | Anxiolytic |

FIG. 36

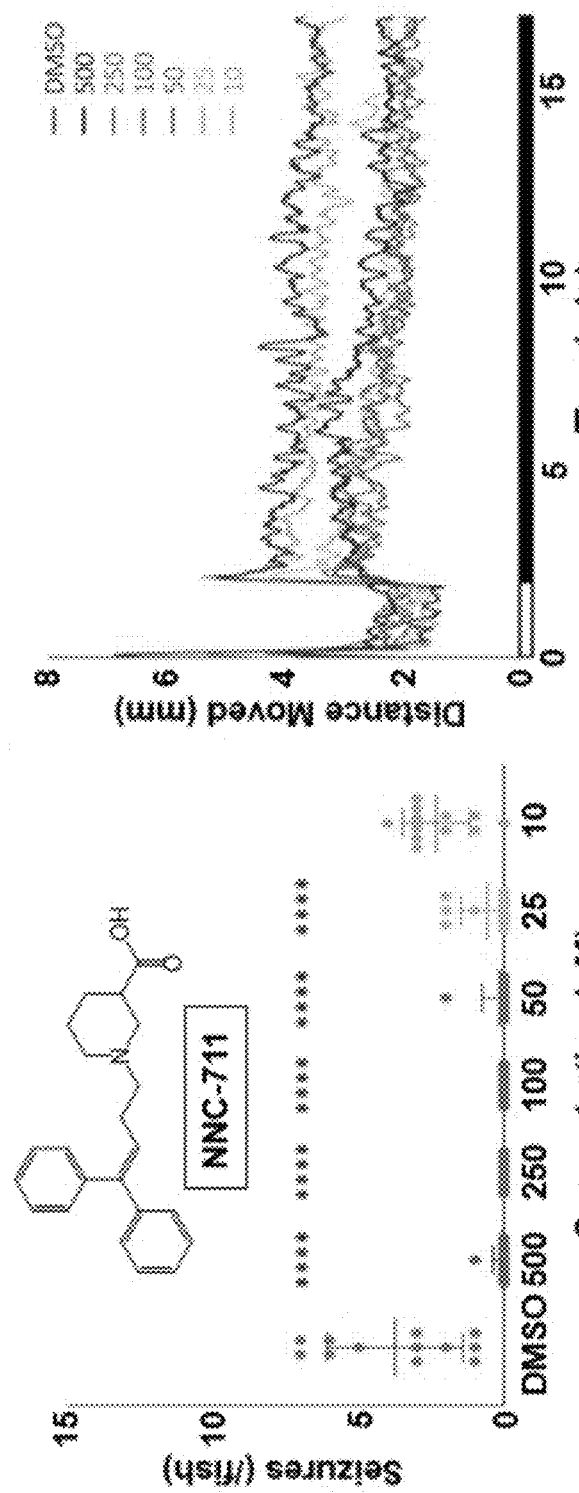
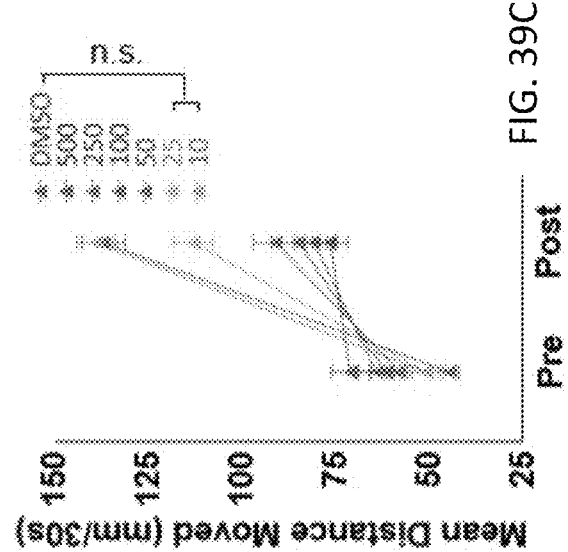
FIG. 39A
FIG. 39B
FIG. 39C

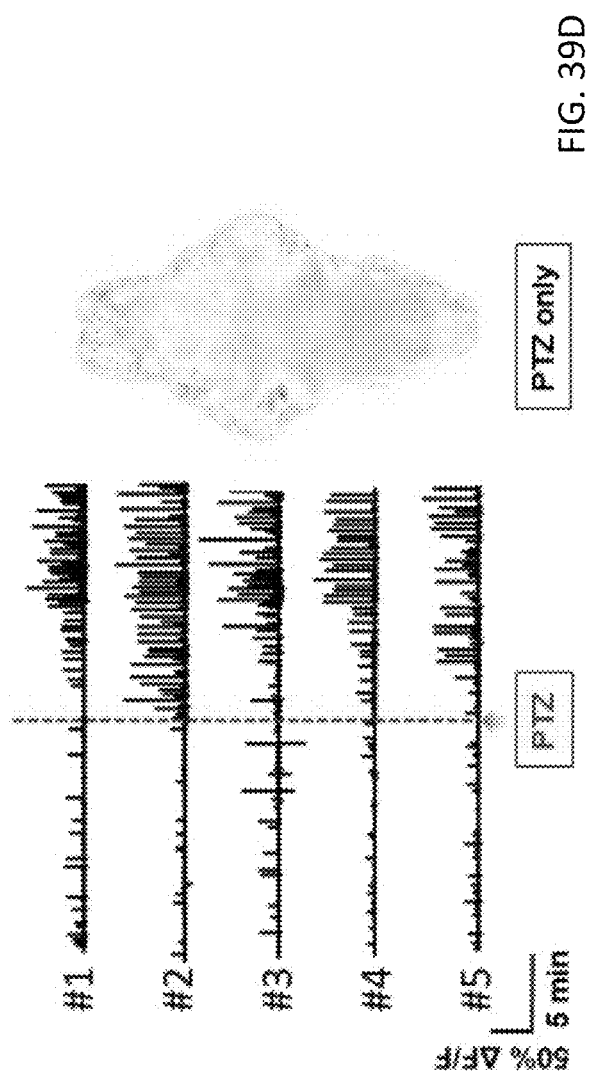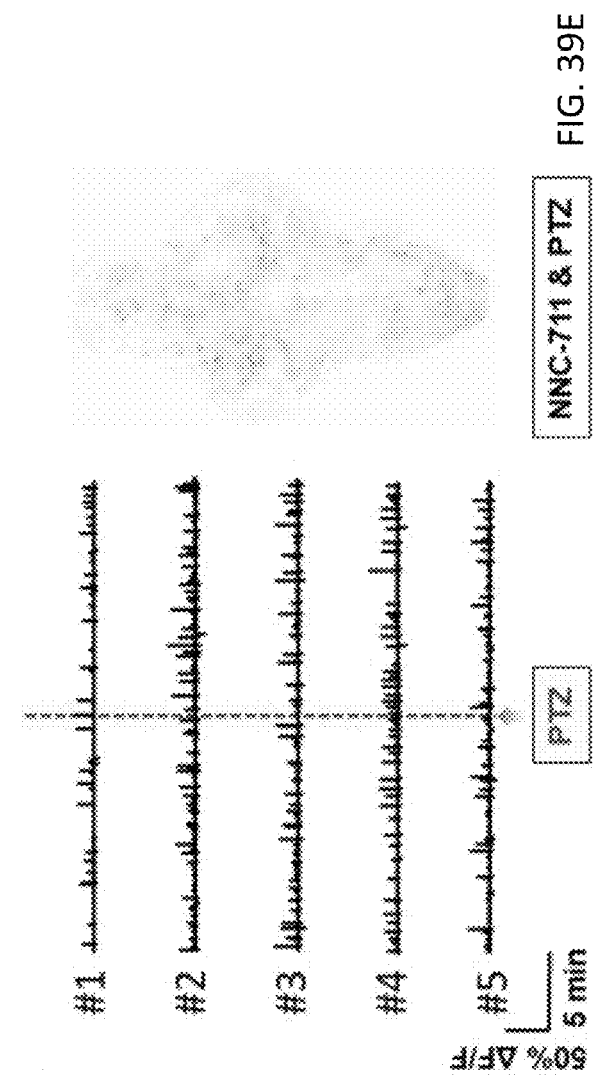

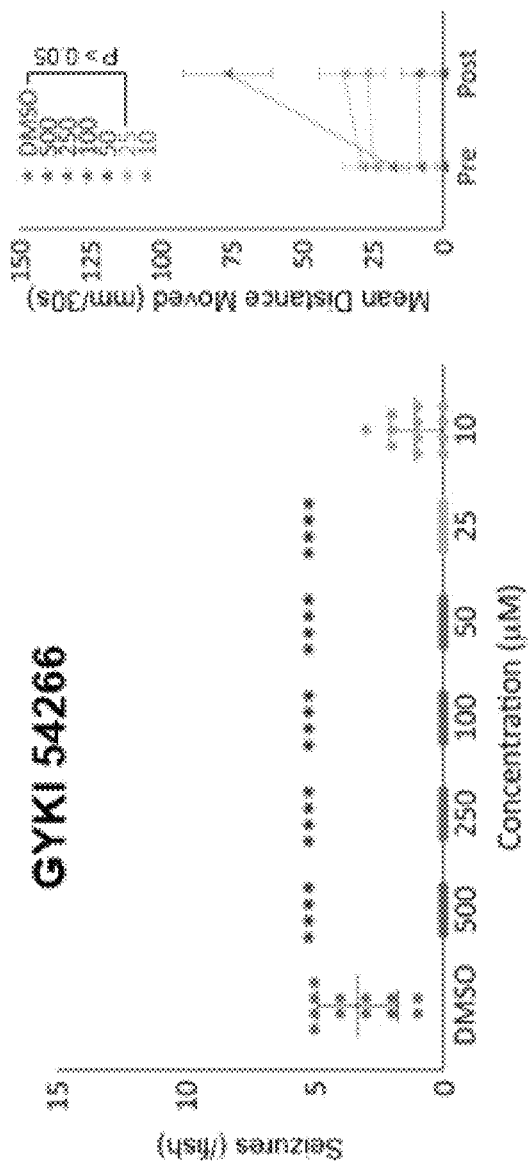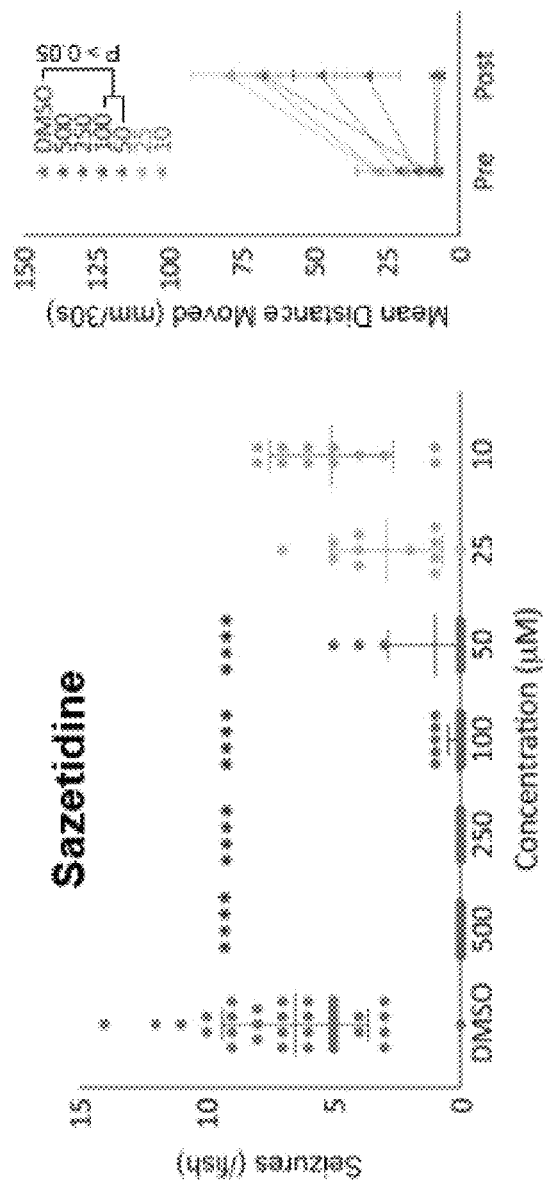

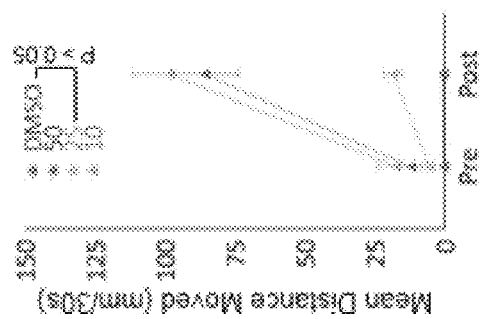
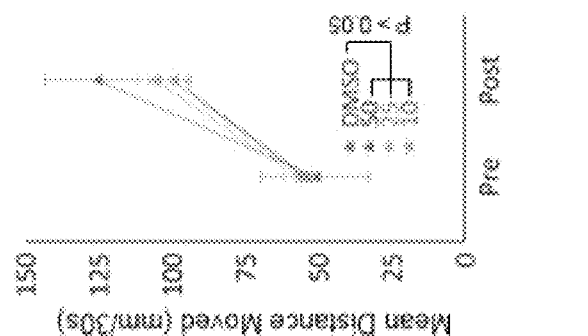
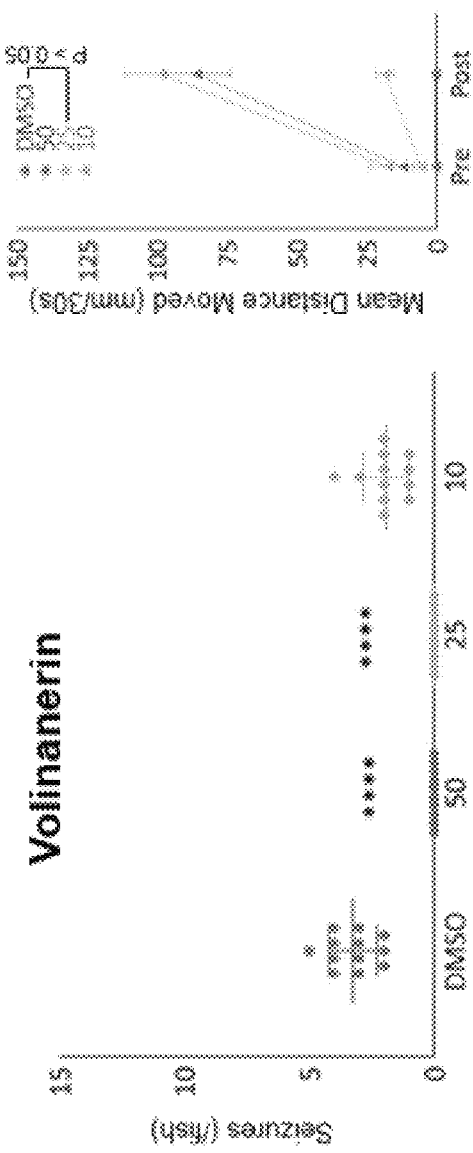
FIG. 40C
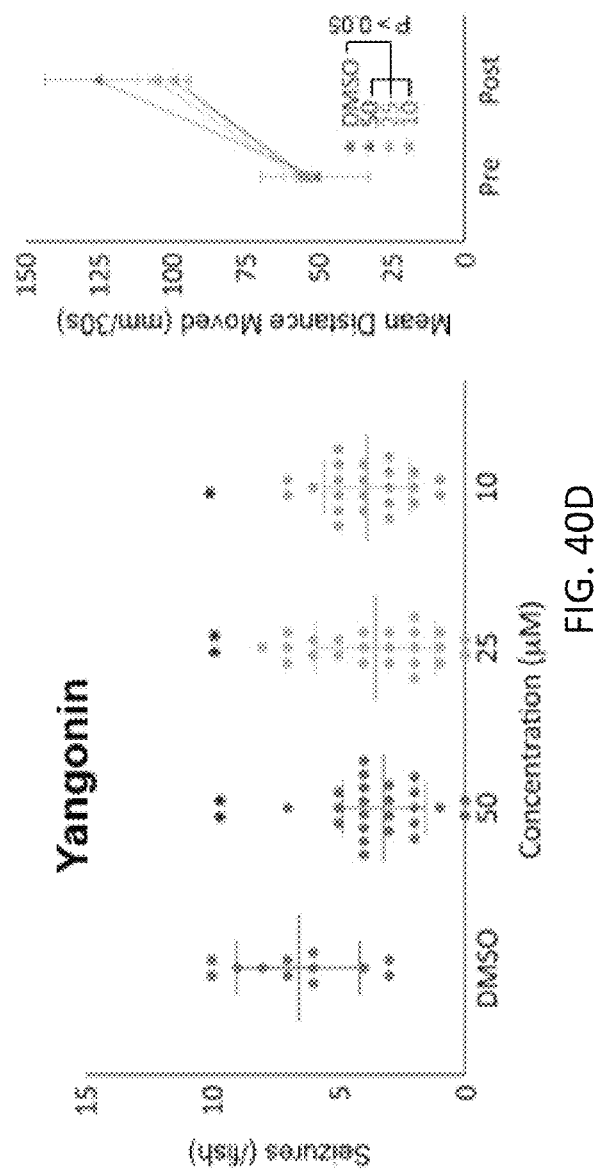
FIG. 40D

METHOD AND A SYSTEM FOR ANALYZING NEUROPHARMACOLOGY OF A DRUG

TECHNICAL FIELD

The present invention relates to a method and a system for analyzing neuropharmacology of a drug, and particularly, although not exclusively, to a drug screening method that utilizes functional brain physiology phenotypes and computational bioinformatics analysis.

BACKGROUND

Drug screening is a method for identifying and verifying pharmaceutical effect of a chemical compound on living species. In general, it is necessary to perform multiple stages of the drug screen process from predicting the effect of an unknown drug to verifying the pharmacology of such drug before allowing the drug to be used as medication for human beings.

SUMMARY OF THE INVENTION

In accordance with a first aspect of the present invention, there is provided a method for analyzing neuropharmacology of a drug, comprising the steps of: providing a set of brain activity maps representing changes of a brain activity of a living species under an influence of a plurality of known drugs each consisting of a known chemical structure; clustering the set of brain activity maps to form a plurality of functional classifiers; and classifying a brain activity map associated with a chemical compound using the functional classifiers so as to predict a neuropharmacology of the chemical compound.

In an embodiment of the first aspect, the step of classifying a brain activity map with the chemical compound using the functional classifiers includes a statistical analysis and/or a machine learning process.

In an embodiment of the first aspect, the step of classifying the brain activity map with the chemical compound using the functional classifiers comprises the step of identifying a relationship between the set of brain activity maps and at least one therapeutic function of the known chemical structures of the plurality of known drugs.

In an embodiment of the first aspect, the step of classifying a brain activity map with the chemical compound using the functional classifiers comprises the step of ranking the chemical compound based on the identified relationship associated with the known chemical structures of the plurality of known drugs.

In an embodiment of the first aspect, the relationship is represented as a plurality of coefficients and/or factors being used for the ranking.

In an embodiment of the first aspect, the method further comprises the step of determining standardized scores for each of a plurality of regions of interest on each of the brain activity maps associated with the plurality of known drugs and the chemical compound.

In an embodiment of the first aspect, the standardized scores includes T-scores.

In an embodiment of the first aspect, the method further comprises the step of obtaining a plurality of score maps associated with the standardized scores and each of the brain activity maps.

In an embodiment of the first aspect, each of the plurality of score maps is obtained by filtering the determined standardized scores with a template of a brain of the living species.

In an embodiment of the first aspect, the step of clustering the set of brain activity maps to form a plurality of functional classifiers comprises the step of applying principle component analysis to decompose the plurality of score maps into a plurality of characteristic features.

In an embodiment of the first aspect, the step of clustering the set of brain activity maps to form a plurality of functional classifiers comprises the step of generating the functional classifiers based on the plurality of characteristic features obtained by a supervised clustering method or an unsupervised clustering method.

In an embodiment of the first aspect, the method further comprises the step of generating the brain activity maps representing changes of the brain activity under the influence of each of the plurality of known drugs and the chemical compound.

In an embodiment of the first aspect, the step of generating the brain activity maps comprises the step of obtaining images of a brain of the living species under the influence of each of the plurality of known drugs and the chemical compound.

In an embodiment of the first aspect, the step of generating the brain activity maps further comprises the step of constructing the brain activity maps based on counting neural spikes representing changes of brain activity as detected on the images obtained.

In an embodiment of the first aspect, the method further comprises the step processing image raw data of a plurality of image frames obtained in an image capturing process performed on the living species so as to construct each of the images.

In an embodiment of the first aspect, the method further comprises the step of immobilizing the living species so as to obtain the plurality of image frames.

In an embodiment of the first aspect, the method further comprises the step of orienting the living species being immobilized so as to obtain the plurality of image frames.

In an embodiment of the first aspect, the living species is immobilized and oriented by a microfluidic device.

In an embodiment of the first aspect, the living species is loaded to the microfluidic device using hydrodynamic forces.

In an embodiment of the first aspect, the living species includes a zebrafish.

In an embodiment of the first aspect, the living species includes a zebrafish larva.

In an embodiment of the first aspect, the plurality of known drugs includes central nervous system drugs or agents.

In an embodiment of the first aspect, the chemical compound includes a neuroactive compound.

In accordance with a second aspect of the present invention, there is provided a system for analyzing neuropharmacology of a drug, comprising: an imaging module arranged to generate images of a brain of the living species; a transformation module arranged to generate, based on the images generated by the imaging module, a set of brain activity maps representing changes of a brain activity of a living species under an influence of a plurality of known drugs each consisting of a known chemical structure, and a brain activity map associated with a chemical compound; and a processing module arranged to cluster the set of brain activity maps to form a plurality of functional classifiers, and to classify the brain activity map associated with the chemical compound using the functional classifiers so as to predict a neuropharmacology of the chemical compound.

In an embodiment of the second aspect, the chemical compound includes a neuroactive compound.

In an embodiment of the second aspect, the processing module is arranged to process the set of brain activity maps and/or the brain activity map using a statistical analysis and/or a machine learning process.

In an embodiment of the second aspect, the processing module is arranged to classify the brain activity map by identifying a relationship between the set of brain activity maps and at least one therapeutic function of the known chemical structures of the plurality of known drugs.

In an embodiment of the second aspect, the processing module is further arranged to rank the chemical compound based on the identified relationship associated with the known chemical structures of the plurality of known drugs.

In an embodiment of the second aspect, the transformation module is further arranged to determine T-scores for each of a plurality of regions of interest on each of the brain activity maps associated with the plurality of known drugs and the chemical compound.

In an embodiment of the second aspect, the transformation module is further arranged to generate a plurality of T-score maps associated with the T-scores and each of the brain activity maps.

In an embodiment of the second aspect, each of the plurality of score maps is obtained by filtering the determined T-scores with a template of a brain of the living species.

In an embodiment of the second aspect, the processing module is arranged to apply principle component analysis to decompose the plurality of T-score maps into a plurality of characteristic features.

In an embodiment of the second aspect, the processing module is further arranged to generate the functional classifiers based on the plurality of characteristic features obtained by a supervised clustering processing or an unsupervised clustering processing.

In an embodiment of the second aspect, the transformation module is arrange to construct the brain activity maps based on counting neural spikes representing changes of brain activity as detected on the images obtained.

In an embodiment of the second aspect, the imaging module is arranged to process image raw data of a plurality of image frames obtained by an imager capturing the living species so as to generate each of the images.

In an embodiment of the second aspect, the system further comprises a microfluidic device arranged to load the living species to a position to facilitate the imager to capture the living species so as to generate each of the images.

In an embodiment of the second aspect, the microfluidic device is further arranged to immobilize the living species.

In an embodiment of the second aspect, the microfluidic device is further arranged to orient the living species.

In an embodiment of the second aspect, the microfluidic device is arranged to load the living species using hydrodynamic forces.

In an embodiment of the second aspect, the microfluidic device includes one or more microfluidic channel adapted to accommodate one or more of the respective living species.

In an embodiment of the second aspect, the living species includes a zebrafish.

In an embodiment of the second aspect, the living species includes a zebrafish larva.

In an embodiment of the second aspect, the plurality of known drugs includes central nervous system drugs or agents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present invention will now be described, by way of example, with reference to the accompanying drawings in which:

FIG. 16 shows images of the pheno-print vectors for the top 20 PCs and a plot of top 20 PCs account for 53% total variance of T-score BAMS;

FIG. 27 illustrates molecular targets of the drugs in signature subgroup of BAM cluster 4 (associated with N03:Anti-epileptics ATC category), and similar chemical structures of carbamazepine and oxcarbazepine, two known anti-epileptic drugs;

FIG. 28 illustrates molecular targets of the drugs in the signature subgroup of BAM cluster-8 (associated with N04: Anti-Parkinson drugs ATC category), and chemical structures of Levetiracetam (N03:anti-epileptic) and Piracetam (N06:psychoanaleptics), which are in distinct ATC categories and find largely different clinical uses despite their structural similarity;

FIG. 31 are brain maps showing functional signatures generated from the signature sub-group in BAM cluster 4 (left), cluster 3 (middle) and cluster 8 (right);

FIG. 32 is an illustration showing a prediction of the non-clinical compounds using the HT-BAMing technology; including a list of top-rated compounds predicted to be potent N03:Anti-epileptic drug candidates, the chemical structures of several predicted potent antiepileptic compounds with distinct molecular targets, including GABA modulators (Gaboxadol, NNC-711 and SKF-89976), AMPA modulators (GYKI-52466, GYKI-53655 and Fanapanel) and HDAC inhibitors (Tubastatin A, CI-994 and YC-5-169);

FIG. 33 is a table showing rank-sorting the compounds by correlation to the signature subgroup (the association of BAM cluster 4 with N03:Anti-epileptics ATC category), 14 compounds (Green shaded) ranked in the top were found to have relevant supports of having anticonvulsant effects;

FIG. 36 is a table showing compounds rank-sorted (Blue shaded) based on correlation to the signature subgroup (the association of BAM cluster 4 with N03:Anti-epileptics ATC category) in the reliability test;

FIG. 39A is a plot showing the seizure count over 15 minutes in larvae exposed to 5 mM PTZ after 4-hour pre-incubation with NNC-711 at different concentrations (10~500 nM) in the behavioral test of FIG. 38, a dose-dependent reduction in seizures is noted, error bars indicate standard error of the mean (s.e.m.), n=12, **** indicates p<0.0001 by one way ANOVA tests;

FIG. 39B is a plot showing representative results for the movement behavioral responses with NNC-711 pre-incubation at different concentrations (10~500 nM) of in the behavioral test of FIG. 38;

FIG. 39C is a plot showing a statistical analysis of the locomotive behavior of the larvae in response to the pre-incubation with NNC-711 at different concentrations (10~500 nM), each larva's movement was monitored for 15 minutes after a 2 minute light stimulation, error bars indicate s.e.m., n=12, larvae treated with DMSO were used as a control, "n.s." stands for no significant difference with p>0.05 by ANOVA test;

FIGS. 39D and 39E are plots showing traces of calcium fluctuation from 5 larval brains and the associated T-score BAM showing the seizure activity induced by 5 mM PTZ treatment, and traces of calcium fluctuation from 5 larval brain and the associated T-score BAM showing the reduction of seizure activity in PTZ-larvae by a 4 hour treatment of NNC-711 at 10 µM, respectively; and FIGS. 40A to 40F are plots showing more hit compounds identified from the behavioral test using a PTZ seizure animal model, seizure count over 15 minutes in larvae treated with 5 mM PTZ after 4 hour incubation with Sazetidine, GYKI 54266, Volinanerin, Yangonin, Tubastatin A and Tabimorelin at different concentrations ranging from 10 to 500 µM, compared to control groups only treated with DMSO, the statistical analysis of the larvae's locomotive behavior before and after a 4 hour pre-treatment with the compounds were also included in each panel, compared to controls (DMSO), larval behavior and movement was monitored for 15 minutes after a 2 minute light stimulation, error bars indicate s.e.m., n=12, **p<0.0001, *p<0.001, **p<0.01, *p<0.05 by one way ANOVA.

DETAILED DESCRIPTION OF THE PREFERRED EMBODIMENT

Figure 1:
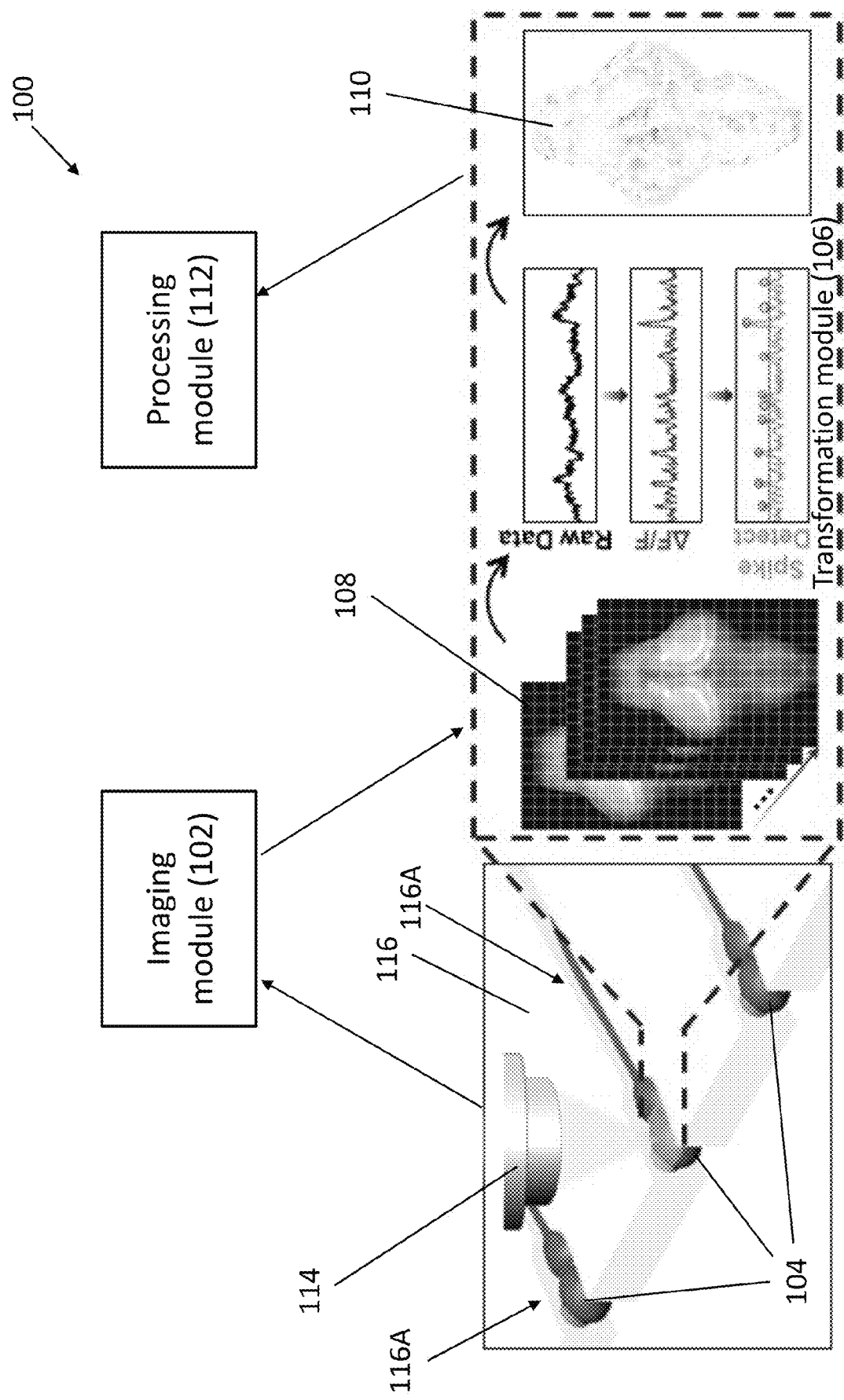
FIG. 1 is an illustration showing a system for analyzing neuropharmacology of a drug in accordance with an embodiment of the present invention.

The inventors have, through their own research, trials and experiments, devised that, treatment rather than cure is generally the rule for most central nervous system (CNS) disorders, with many options only providing limited or partial relief.

Despite tremendous efforts to elucidate the molecular mechanisms of CNS disorders at the level of specific membrane receptors, ion channels and signaling pathways, the understanding of the pathophysiology of these disorders remains incomplete. Many clinically effective pharmacological treatment strategies for CNS disorders are the result of serendipitous discoveries, and often affect multiple pathways through diverse functional mechanisms making it difficult to deconvolute the molecular mechanisms underlying efficacy.

For example, topiramate is an anticonvulsant which may be used for focal and general seizures. In another example, migraine may bind to multiple targets, including voltage-gated sodium channels, high-voltage-activated calcium channels, γ-aminobutyric acid (GABA) receptors, α-amino-3-hydroxy-5-methyl-4-isoxazolepropionic acid (AMPA) receptors and other biogenic amine receptors.

To address the limitations of some CNS pharmacopeia, CNS drug discovery strategies may be limited by their reliance on overly simplified experimental systems, such as isolated biochemical binding tests and in vitro cell-based assays. These systems may not recapitulate the in vivo complexity of the CNS, and may be limited in their ability to predict therapeutic outcomes in the context of human disease biology. Therefore, it may be preferable to establish novel paradigms that can monitor and evaluate the complex brain functionusing multiplexed physiological phenotypes.

In some examples, small whole organisms, such as *C. elegans* and zebrafish may be used in drug screening without prior molecular knowledge of the lead chemicals. However, the readouts may be limited to behavioral analysis and morphological phenotyping in some analysis. Furthermore, some of these assays may suffer from the disadvantage that they fail to correlate a drug's therapeutic effects directly to physiological changes in the CNS of the model organism.

In some preferable embodiments, whole-brain imaging of small animals, such as zebrafish, may provide an effective means of bridging the gap between large-scale cellular activity and behavioral responses. The data can be used to develop drug-screening platforms based purely on complex functional phenotypes. Preferably, the method may be applied to CNS drug discovery beyond the testing of a limited number of agents over a small parameter space of dose and time.

In one preferable embodiment of the present invention, there is provided a method for analyzing neuropharmacology of a drug. The method preferably comprises the steps of providing a set of brain activity maps representing changes of a brain activity of a living species under an influence of a plurality of known drugs each consisting of a known chemical structure; clustering the set of brain activity maps to form a plurality of functional classifiers; and classifying a brain activity map associated with a neuroactive compound using the functional classifiers so as to predict a neuropharmacology of the neuroactive compound.

Preferably, the embodiments of the present invention may be applied as a high-throughput, in vivo drug screening method that combines automated whole-brain activity mapping (BAMing) with computational bioinformatics analysis. Different from some example drug screening methods involving relatively simple models, the preferred method utilizes functional brain physiology phenotypes derived from live, non-anesthetized zebrafish that have been treated with compounds of interest as an input for predicting the therapeutic potential of novel bioactive compounds. Preferably, the method of the present invention may rely on an autonomous robotic system capable of manipulating awake zebrafish larvae for rapid microscopic imaging of their brains at the level of cellular resolution, which may allow for rapid assessment of action potential firing across a whole zebrafish brain; as a result, a large number of whole-brain activity maps (BAMs) can be acquired for a compound library.

In addition, the brain activity maps may be further analyzed. In a first part of the analysis, it may employ a "training set" of 179 clinical drugs to generate information-rich BAMs; the intrinsic coherence among the BAMs for drugs in the training set may be determined by a consensus clustering algorithm. The BAM clusters may be further found to be statistically associated with the drugs' therapeutic categories as determined by the World Health Organization (WHO) Anatomical Therapeutic Chemical (ATC) classification system.

In the second part of the analysis, a strategy employing machine learning may be used to build a functional classifier along with a ranking mechanism to predict the potential novel therapeutic uses of compounds based upon their similarity to clinically used drugs. Using a machine learning process, the successful prediction of compounds may be highlighted with anti-epileptic activity in zebrafish behavioral models from a library of 121 non-clinical compounds. These embodiments may facilitate development of next-generation anti-epileptic agents with novel mechanisms of action.

With reference to FIG. 1, there is shown an embodiment of a system 100 for analyzing neuropharmacology of a drug, which may be used to perform the abovementioned drug screen method. The system comprises an imaging module 102 arranged to generate images of a brain of the living species 104; a transformation module 106 arranged to generate, based on the images 108 generated by the imaging module 102, a set of brain activity maps 110 representing changes of a brain activity of a living species 104 under an influence of a plurality of known drugs each consisting of a known chemical structure, and a brain activity map 110 associated with a chemical compound; and a processing module 112 arranged to cluster the set of brain activity maps 110 to form a plurality of functional classifiers, and to classify the brain activity map 110 associated with the chemical compound using the functional classifiers so as to predict a neuropharmacology of the chemical compound.

In this embodiment, the imaging module 102 is arranged to obtain or generate an image 108 of a living species, in particular an image 108 focusing on the brain of such living species 104. For example, living species such as a zebrafish or a zebrafish larva has a brain and some other parts of it covered by optically transparent or translucent skin, therefore image frames 108 illustrating the brain of a zebrafish or its larva may be captured using imager such as an optical imager 114 or camera.

The transgenic zebrafish line elav13:GCaMP5G may be maintained in aquaria under standard laboratory conditions (at 28° C. under a cycle of 14 h light, 10 h dark). Larvae of 6-8 dpf were used in the HT-BAMing experiments.

Preferably, the imaging module 102 may process image raw data of the image frames 108 obtained by an imager 114 capturing the living species 104 so as to generate images 108 of the brain of the living species 104. For example, the imaging module 102 may further process the image frames by combining multiple image frames of similar objects being captured or to extract important information from the image raw data in multiple images so as to generate an output image that may be more suitable for further analysis.

For example, the imaging process may be performed on a fully automated inverted fluorescent microscope (Olympus IX81) equipped with a cooled sCMOS camera (Neo, ANDOR) with a 10× (NA, 0.4) objective. Micro-manager 1.4 may be installed to control the microscope. For high-resolution, confocal imaging and Leica SP8 microscope with a resonant scanner may be used.

Referring to FIG. 1, the system 100 further comprises a structure for immobilizing and aligning zebrafish larvae such that the image frames captured by the imager is not blurred due to the movements of the living species. Preferably, a microfluidic device 116 may be used load the living species 104 to a position for image capturing to facilitate the imager 114 to capture the living species 104 and to generate the images 108. In addition, the loaded zebrafish larvae may be applied with a predetermined dose of a chemical compound, such as but not limited to a neuroactive compound, a drug which include a known chemical structure but an unknown biological or pharmaceutical effect to a living species or even an unknown chemical compound in a testing agent.

Preferably, the microfluidic device 116 may include one or more microfluidic channels 116A each with a dimension that fit a single zebrafish larva of a predetermined size to be loaded therein. The microfluidic device 116 may load the living species using hydrodynamic forces, such that the zebrafish larva is properly aligned/oriented when it reaches the position for image capturing. In addition, as the movement living species is restricted by the flowing rate of the fluid in each of the microfluidic channels, the living species 104 may be immobilized which facilitate capturing a clear image of the living species 104.

In one example embodiment, a negative mold of a microfluidic chip 116 may be fabricated by high-resolution (30 μm resolution) Computer Numeric Control (CNC) machining using a plain copper plate. The transparent flow channels were then made by molding from the copper molds using polydimethylsiloxane (PDMS). After curing for 12 hours, the PDMS structures were released from the molds and then bonded to glass substrate after plasma treatment to form the final microfluidic chip. Alternatively, the microfluidic chip may be fabricated using any fabrication process (such as 3D-printing, imprint, etching technologies etc.) as appreciated by a skilled person.

Calcium sensitive fluorescent reporters may be used for recording of brain-wide activity in larval zebrafish with single-cell resolution. In this example, changes in the fluorescence of calcium-sensitive fluorophores enable imaging of neuronal activity. To further enhance the throughput of whole brain CNS physiology analysis, an autonomous system capable of orienting and immobilizing multiple awake, non-anesthetized animals may be used for high-throughput recording of brain-wide neuronal activity.

Figure 3:
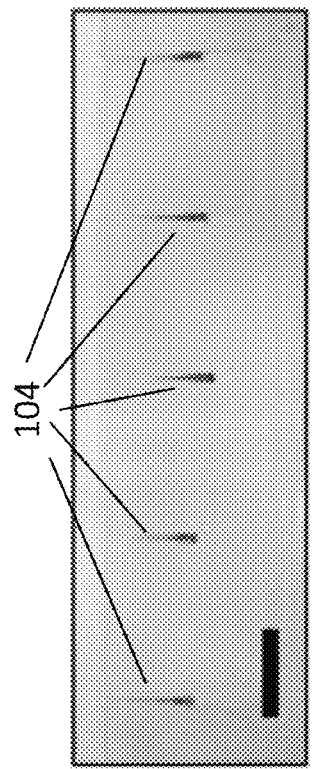
FIG. 3 is an image showing immobilization of multiple awake larvae in a microfluidic chip with a dorsal-up orientation, the scale bar is 5 mm.
Figure 2:
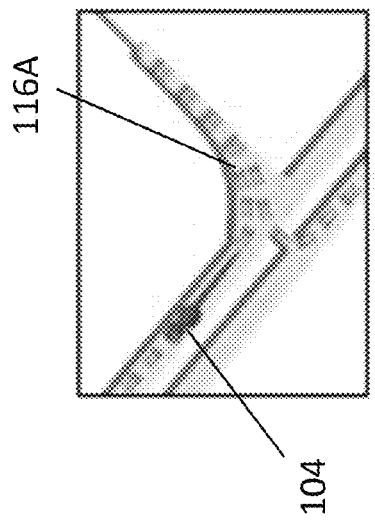
FIG. 2 is a schematic diagram illustrating the use of hydrodynamic force to load, orient and immobilize zebrafish larvae, the arrows indicate the direction of bulk flow in the microfluidic chip.

With reference also to FIG. 2, there is shown an illustration of using hydrodynamic force to load, orient and immobilize zebrafish larvae 104 in a microfluidic channel 116A. The arrows indicate the direction of bulk flow in the microfluidic chip. Referring to FIG. 3, five individual zebrafish larvae 104 may be loaded and aligned in the microfluidic device 116, which facilitate a higher throughput of capturing raw image data using multiple microscopic imagers 114.

Figure 4:
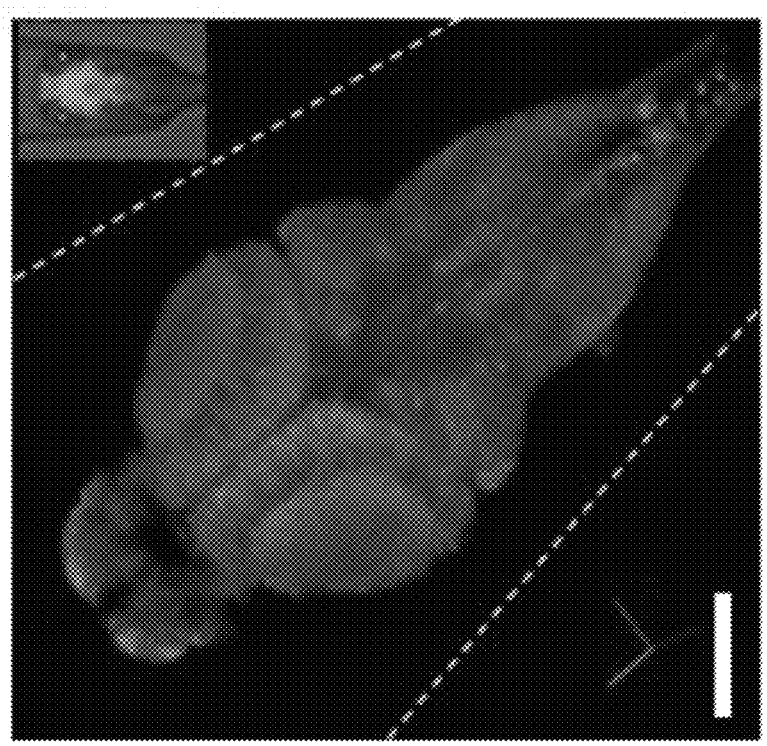
FIG. 4 is a representative brain image of a larva (from elav13:GCaMP5G transgenic line) trapped in the system, the inset shows the merged image of the larva trapped in the chip, and the white dotted line indicates the trapping channel, the scale bar is 100 μm.

In one example experiment performed by the inventors, all larvae were loaded with a dorsal-up orientation to facilitate brain imaging from above. With reference to FIG. 4, the use of transgenic zebrafish (elav13:GCaMP5G) with a genetically encoded calcium indicator allowed for real-time whole-brain imaging, and subsequent analysis of drug-induced changes in neuronal activity.

Figure 5:
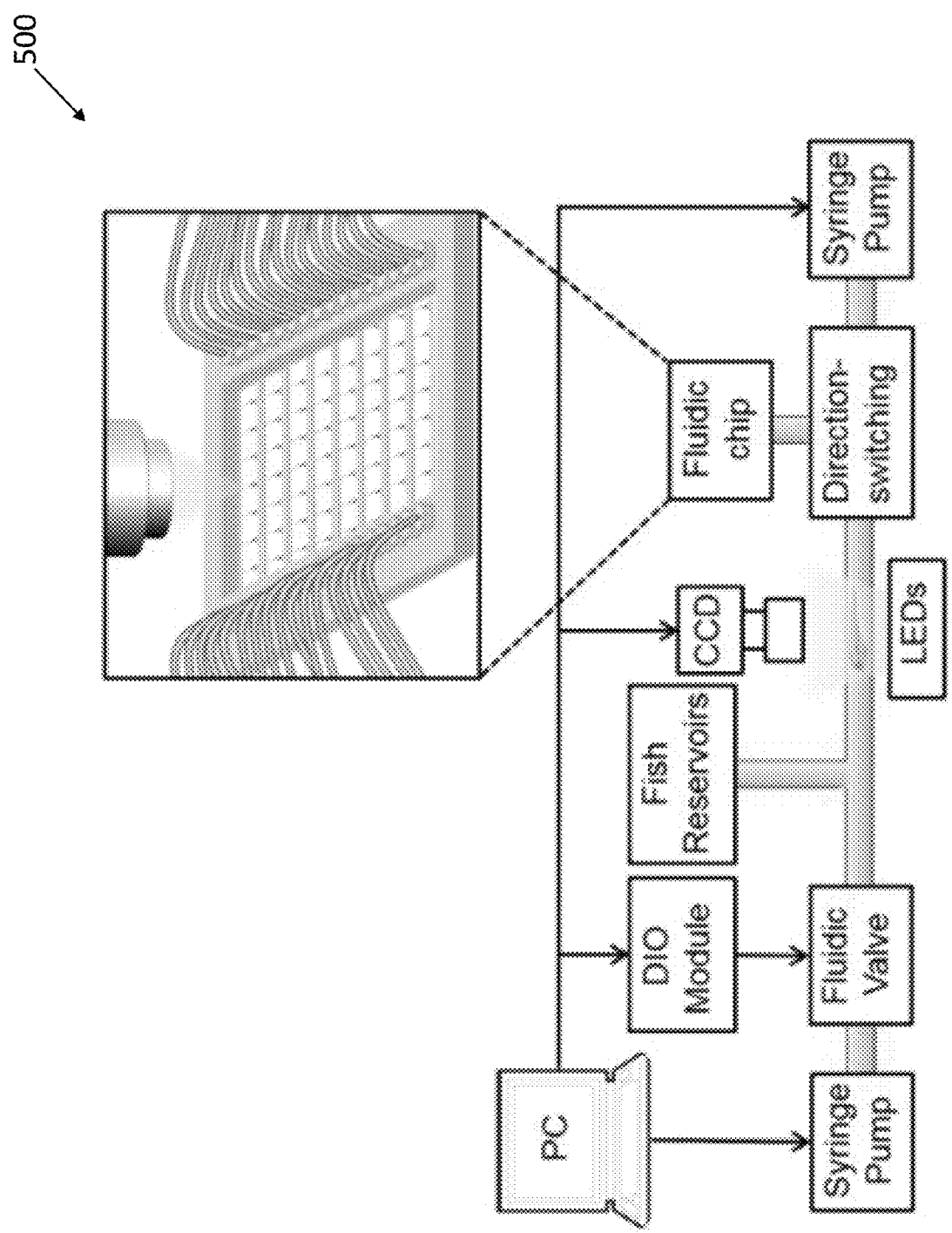
FIG. 5 is block diagram showing an automated system for handling larval zebrafish and drug perfusion in accordance with an alternative embodiment of the present invention.

With reference to FIG. 5, the processing throughput may be further enhanced by a system 500 for larvae loading and transportation that employs digitally controlled syringe pumps, electromagnetic valves and video detection to enable automatic feeding of larvae into the microfluidic chip.

Figure 6:
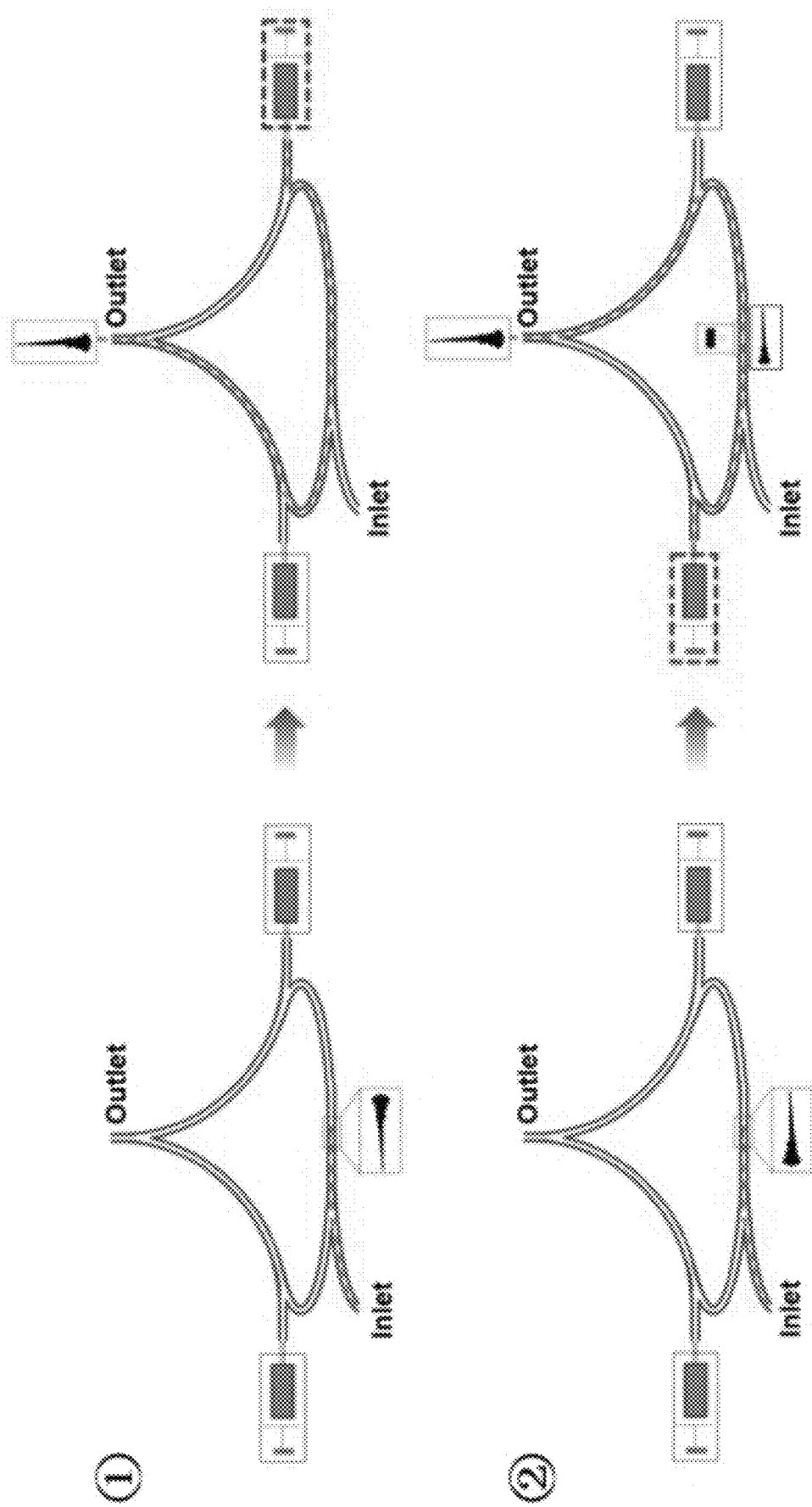
FIG. 6 is an illustration showing a direction-switching-loop for loading the larval zebrafish in opposite directions.
Figure 7:
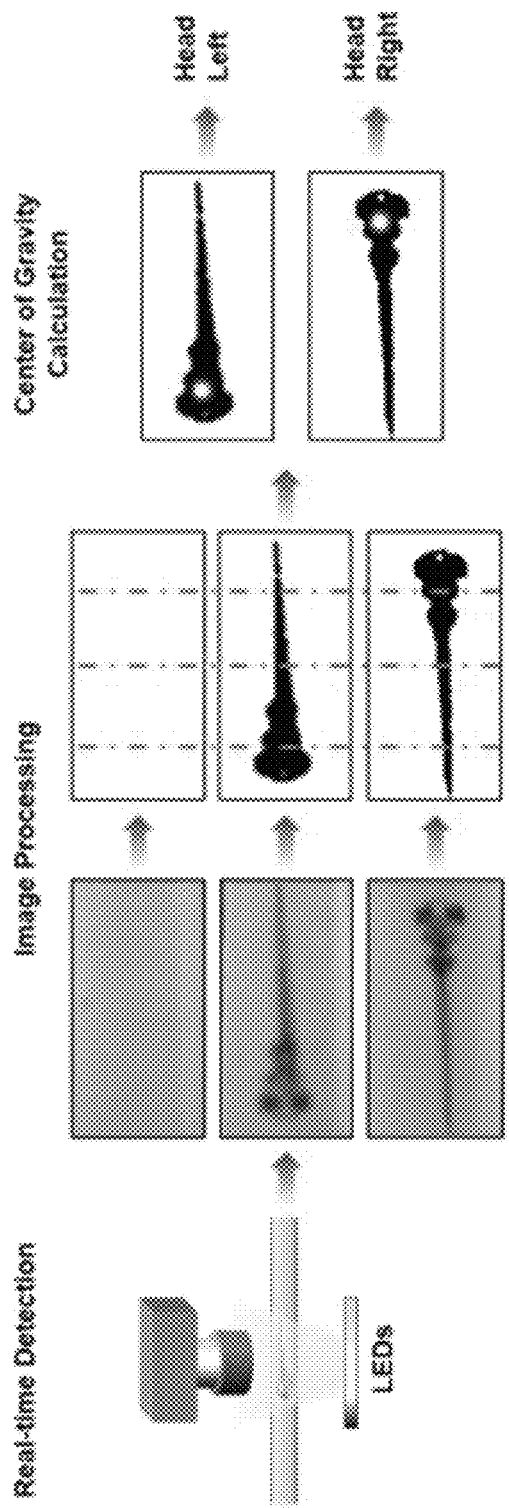
FIG. 7 is an illustration showing a video- or image-detection module coupling with an image processing algorithm for detecting and capturing images of the larval zebrafish.

Referring to FIGS. 6 and 7, there is shown an illustration of the flow direction-switching-loop. In this example, for a larva loaded with head facing forward in panel ①, the right pump (in red box) is engaged to pump the larva into the Fish-Trap chip. For a larva loaded with tail facing forward in panel ②, the left pump (in red box) is engaged to pump the larva into the chip. In panel ① & ②, the actually flow direction indicated by the blue dash line. Therefore, a single imager device is sufficient in the image or video detection module for capturing image frames of the live larvae oriented in both directions.

For example, two syringe pumps (RSP01-B; RISTRON) may be used to load the zebrafish larvae from a reservoir into the capillary fluidic circuitry. A NIDAQ input-output card (NI USB 6525) may be used to digitally control the pumps and the electromagnetic fluidic valves (WK04-010-0.5/1-NC; Wokun Technology) to perform automated control of larva handling cycles. A video detection module may be used detect the passage and the larva head direction, which was used as a trigger signal to the direction-switching-loop module.

The module may be designed to adjust the direction of the larva after loading from the reservoir to ensure each larva was in a tail-forward direction before being loaded into the microfluidic chip. For fast larva detection, the image capturing process may be designed to extract every frame from the real-time recording and convert it to a binary image, and the head portion was then identified by simple center of gravity detection.

Figure 8:
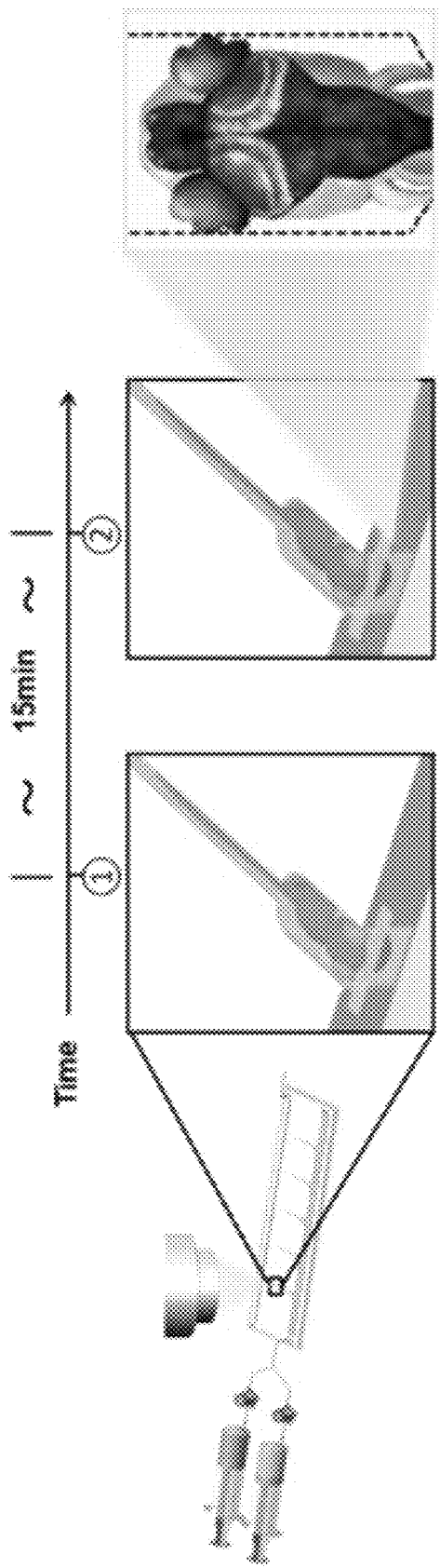
FIG. 8 is an illustration showing a drug prefussion process at the microfluidic channel.
Figure 9:
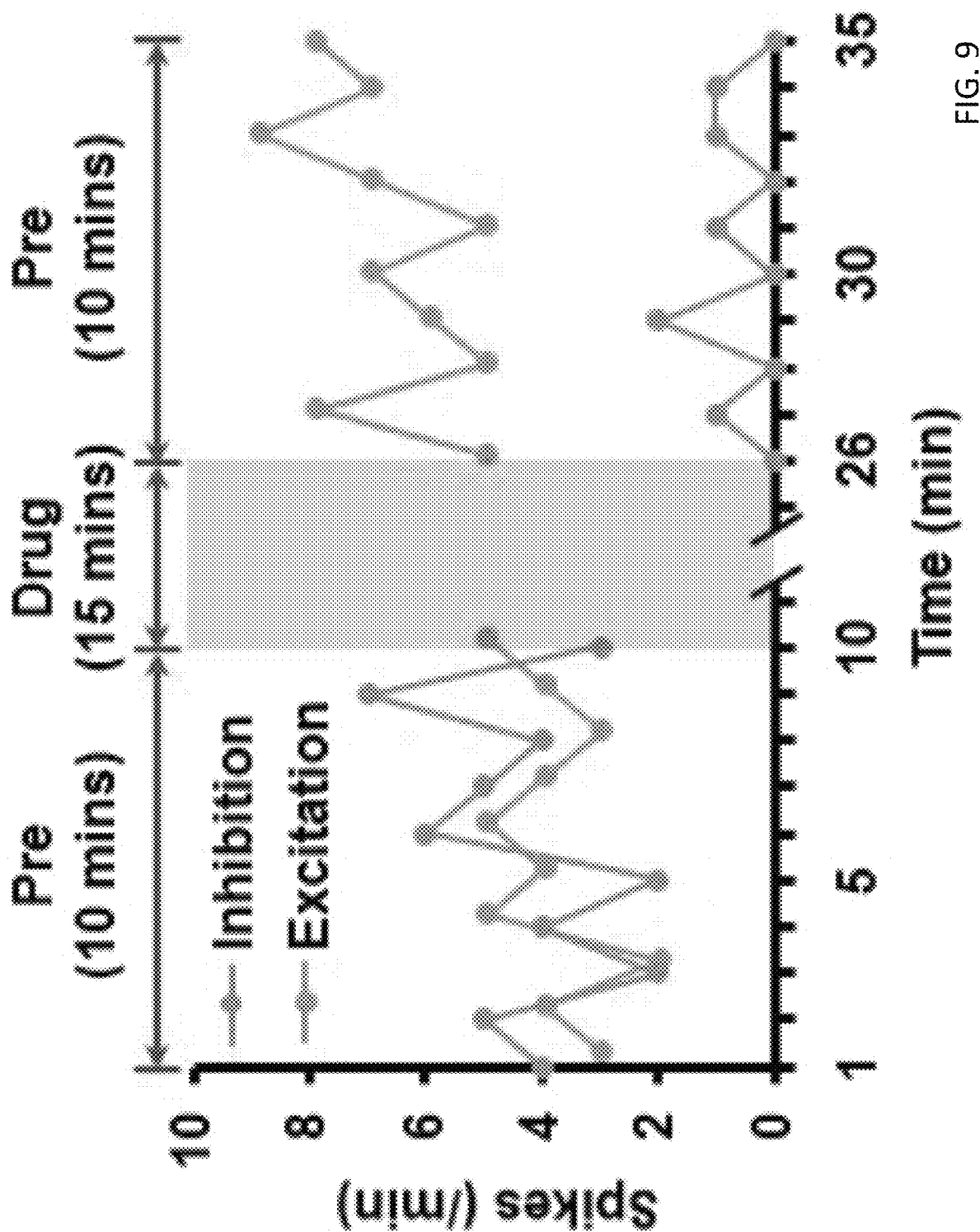
FIG. 9 is a plot showing the change of action potential firing rate in selected neuronal cells from a zebrafish brain, the sample showing inhibition was treated with the typical antipsychotic Loxapine, while the sample data showing excitation follows treatment with Pyrithioxine.

Furthermore, a drug perfusion time may be set in which the two syringes may contain different fluid or solutions such that the changes induced by the drug may be recorded. With reference to FIGS. 8 and 9, to generate the functional BAM of a larva in response to a 15-minute period of chemical perfusion, or "treatment", each larva was imaged over a 10-minute period before and after treatment.

In the experiments performed by the inventors, all drugs or compounds were dissolved in DMSO as a vehicle as ~10 mM stock solutions. Treatment of the larvae was performed simply by switching the perfusion solution after immobilizing larvae in the microfluidic chip as shown in FIG. 8. Final concentrations of compounds tested in the primary screen were ~10 M.

Once the images of the brain of the zebrafish are generated, the images may be further processed, preferably by a transformation module to transform the image data which is embedded with the brain activity of the zabrafish under an influence of a drug or a neuroactive compound. Preferably, the changes of brain activity may be represented by a brain activity map showing the neuroactivity of brain for each of the drug or chemical compound being tested. For example, the known drugs and/or the chemical compound being tested may include central nervous system drugs or agents, which may affect the brain activities during an effective period. On the other hand, some chemical compounds or drugs may induce no effects on the central nervous system of a living species or the zebrafish.

In one example embodiment, the transformation module 106 is arrange to construct the brain activity maps 110 based on counting neural spikes representing changes of brain activity as detected on the images obtained. With reference to FIGS. 1 and 9, readings from multiple focal planes along the Z-axis (ventral direction) were acquired, and accumulated spike counts were derived from the calcium fluctuations of each Z-plane with a lateral resolution of 15.21 $\mu m^2$. The difference in spike-counts between the post- and pre-treatment periods was calculated and projected (by summing up along the Z-axis) to a two-dimensional surface to construct a BAM that reflects changes in brain activity and physiology of an individual larva in response to treatment.

Figure 10:
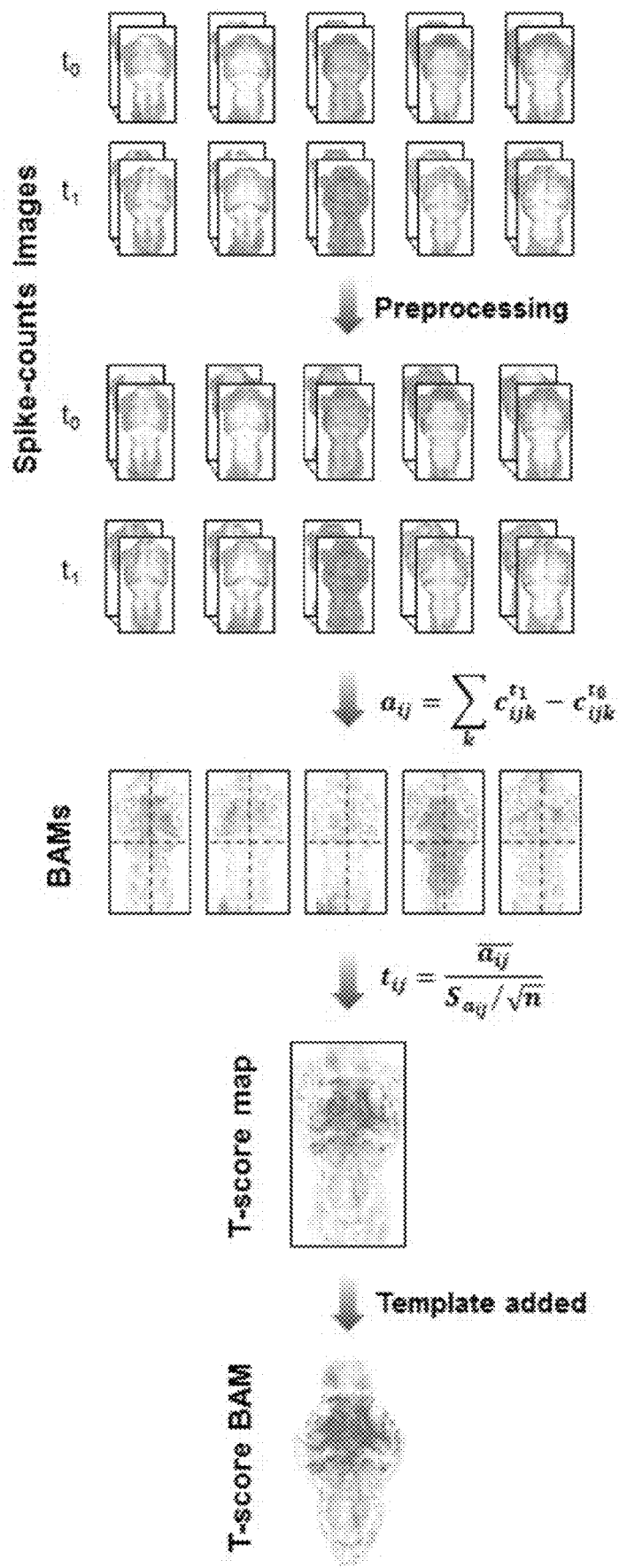
FIG. 10 is an illustration showing an analytical workflow for the generation of T-score brain activity maps (T-score BAMs), including keys steps for calculation of a T-score BAM, involving image-based preprocessing of spike count data, generation of brain activity maps, calculation of a T-score map, as well as filtering with a uniform zebrafish brain template.

With reference also to FIG. 10, a heat map may be used to intuitively display the activation level of the brain. To map brain activity, every collected frame from calcium imaging may be first meshed into small ROIs, each with a size of 15.21 $\mu m^2$. The time series of fluorescence signal in each ROI may then be filtered by a high pass filter to remove the interference from illumination fluctuations. The resulting trace may be used to calculate and visualize the spiking activities. For spike counting, a threshold may be applied to detect spikes from neural activity.

In the experiment, for each compound, the spike count data from five independent zebrafish larvae over a 10-minute period before and a 15-minute period after compound treatment. Before comparison across different samples, all the images were first resized and aligned to a uniform zebrafish brain template with the following process: for each raw image, the dark background was first removed to extract the fluorescent brain region, which was then mapped to the standard template via specific transformative adjustments (e.g. rotation, translation) using the brain center-line as a registration landmark and such that the symmetry with respect to the center-line was maximized in the resulted image. Lastly, the fish eye region was further removed by taking the regions within the template for downstream analysis.

A brain activity map (BAM) $A=[a_{ij}]$ was then derived by taking the change (increase or decrease) of spike counts in each ROI before ($t_0$) and after chemical treatment ($t_1$), and summed across multiple layers along the Z-axis:

$$a_{ij} = \sum_k c_{ijk}^{t_1} - c_{ijk}^{t_0}$$

where $c_{ijk}^{t_0}$ and $c_{ijk}^{t_1}$ represent the spike counts of the ROI at row i and column j of the k-th layer before and after chemical treatment, respectively.

For each compound, BAMs from five individual larvae were acquired following treatment with a 10 $\mu$M dose. To avoid false-positive or false-negative errors potentially introduced by variation among different individuals, the five BAMS for each compound were statistically compared by T-score test at every 15.21 $\mu m^2$ unit across the whole projection surface to extract the brain regions significantly regulated by compound treatment.

Preferably, the transformation module 106 may determine standardize scores, including T-scores, for each of a plurality of regions of interest on each of the brain activity maps associated with the plurality of known drugs and the neuroactive compound. In addition, the transformation module 106 may further generate a plurality of T-score maps associated with the T-scores and each of the brain activity maps. The score maps or the T-score maps may be obtained by filtering the determined T-scores with a template of a brain of the living species.

With reference to FIG. 10, there is shown an analytical workflow for the generation of T-score brain activity maps (T-score BAMs). Shown in the workflow are keys steps for calculation of a T-score BAM, involving image-based pre-processing of spike count data, generation of brain activity maps, calculation of a T-score map, as well as filtering with a uniform zebrafish brain template. In this example, a significance score was assigned to each unit to form a T-score brain activity map (T-score BAM) unique to each compound.

For quantitative assessment of the statistical significance of brain activity regulation by a compound, a matrix of T-scores (T-score BAM), $T=[t_{ij}]$, was calculated for each ROIs across the five BAMs from different biological replicates by:

$$t_{ij} = \frac{\overline{a_{ij}}}{s_{a_{ij}}/\sqrt{n}},$$

where $\overline{a_{ij}}$ was the mean brain activity score of the ROI at row i and column j of the five BAMs, $S_{a_{ij}}$ was the standard deviation of the mean, and n=5 was the number of biological replicates.

Figure 11A:
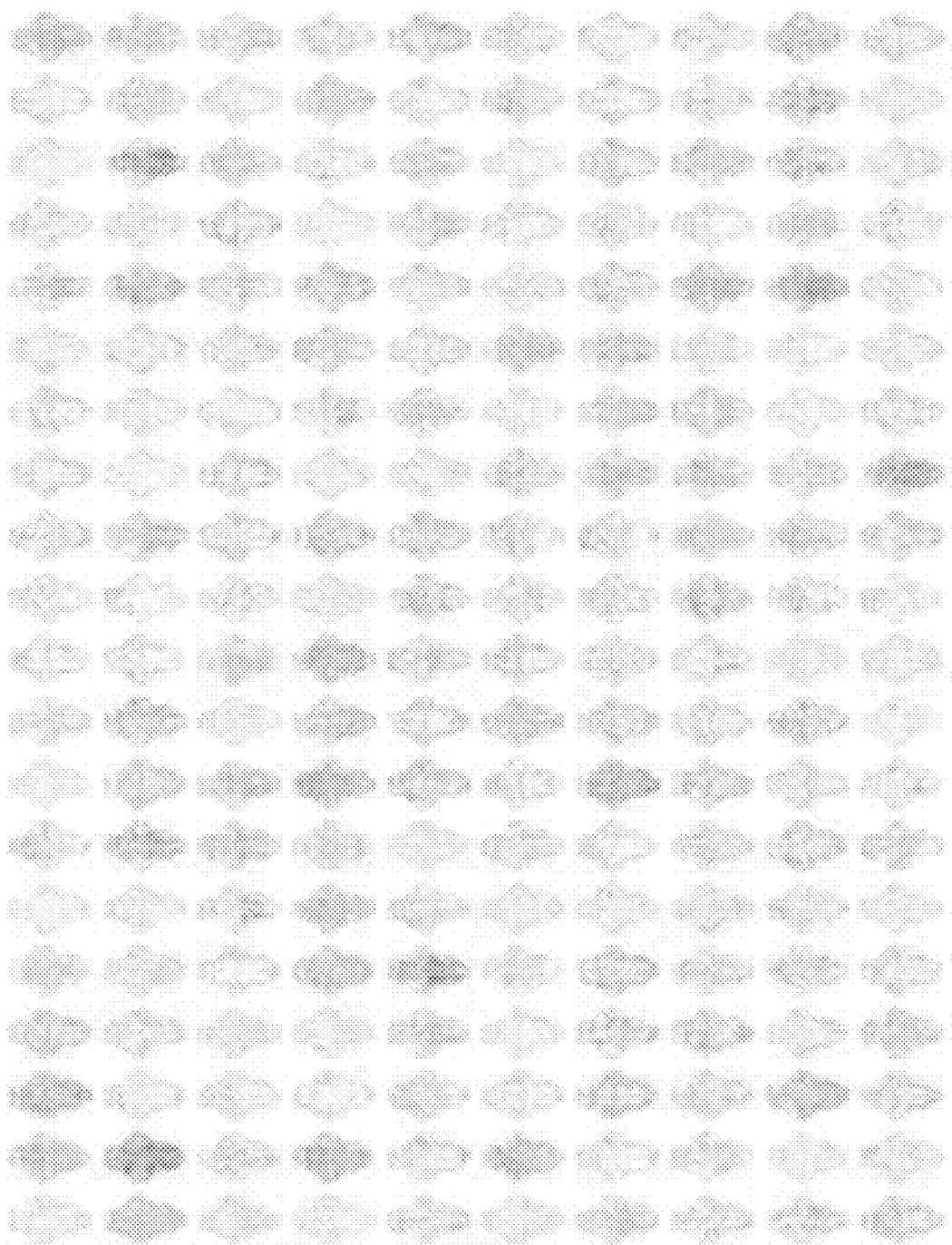
FIG. 11A shows multiple background T-score BAMs calculated from DMSO controls, 5 samples were selected to calculate a background T-score BAM from the in total 50 DMSO controls, and the step was repeated for 1000 times, with 200 T-score BAMs randomly selected and being shown in the Figure.
Figure 11C:
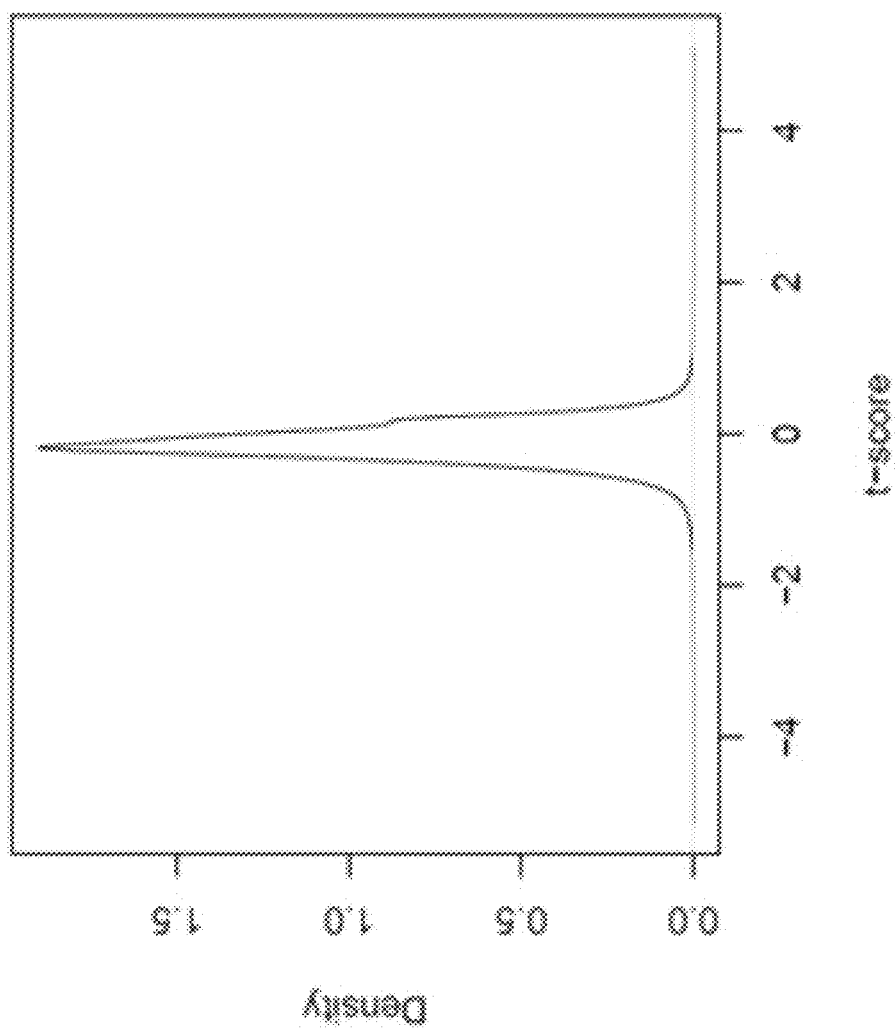
FIG. 11C is a plot showing a pooled distribution of T-scores of FIG. 11B.
Figure 11B:
FIG. 11B shows an average background T-score BAM of 1000 T-score BAMs in total being pooled together to form a background distribution.

With reference to FIGS. 11A to 11C, there is shown background T-score BAMs calculated from DMSO controls. In the control larvae, DMSO treatment resulted in white-noise-like T-score BAMs (n=50). From the in total 50 DMSO controls randomly selected 5 samples were randomly selected to calculate a background T-score BAM, and this step was repeated for 1000 times. 200 T-score BAMs were randomly selected as shown in FIG. 11A. The total 1000 T-score BAMs were pooled together to form a background distribution, with the average background T-score BAM as shown in FIG. 11B, and the pooled distribution of T-scores as shown in FIG. 11C. The background T-score BAMs were white-noise-like, which were distinct from those drug-treated samples.

The HT-BAMing technology presented here enabled large-scale acquisition and rapid analysis of physiologic data and zebrafish brain function. Advantageously, the embodiments of the present invention provides BAM data from larval zebrafish being sufficiently resolved and information-rich to reflect the complex therapeutic effects and changes in CNS physiology caused by exposure to a mechanistically diverse collection of clinically used drugs. The HT-BAMing technique may be applied to a library of 179 clinically used CNS drugs curated to include a variety of distinct mechanisms of action and known therapeutic uses as shown in the following Table.

| No. | Drug Name | ATC code | Chemical structure |
|---|---|---|---|
| 1 | Lacosamide | N03AX18 | O=C(N[C@@H](C(=O)NCc1ccccc1)CCC)C |
| 2 | Rituzole | N07XX02 | FC(F)(F)Oc1ccc2nc(sc2c2)N |
| 3 | Acetazolamide | S01EC | O=S(=O)(c1nnc(s1)NC(=O)C)N |
| 4 | Vorinostat | L01XX38 | O=C(Nc1ccccc1)CCCCCCC(=O)NO |
| 5 | Valproato | N03AG01 | O=C(O)C(CCC)CCC |
| 6 | Chantix | N078A03 | C1C2CNCC1C3.–.CC4.–.NC.–.CN.–.C4C.–.C23.C(C(C(=O)O)O)(C(=O)O)O |
| 7 | Gabapentin | N03AX12 | O=C(O)CC1(CN)CCCCC1 |
| 8 | Amitriplyline | N06AA09 | c3cc2c(/C(c1ccccc1)CCC2)=C\CCN(C)Cc3 |
| 9 | Flavoxate | G04BD02 | O=c1c(OC(c2ccccc2)=C(C)C3.–.O)c3ccc1)OCCN4CCCCC4•Cl |
| 10 | Acamprosate | N07BB03 | CC(NCCCS(O)(=O)=O)=O•[Ca] |
| 11 | Tiagabine | N03AG08 | CC1=C(/C(C2=C(C=CS2)C)=CCCN3CCC[C@@H](C(=O)=O)C3)SC.–.C1•C1 |
| 12 | Fluvoxamine | N06AB08 | COCCC/C(/C1.–.CC.–.CC.–.CC.–.C1)=N\OCCN |
| 13 | Citalopram | N06AB04 | CN(CCC[C@]1(C2.–.CC.–.CC(.–.C2)F)OCC3.–.C1C.–.CC(C#N).–.C3)C•Br |
| 14 | Eletriptan | N02CC06 | CN1CCCC1C2.–.CNC3.–.C2C.–.C(.–.C3)CC3.–.O)(C4.–.CC.–.CC.–.C4).–.O•Br |
| 15 | Methazolamide | S01EC05 | CN1N.–.C(S\N).–.O)S/C1.–.N(C).–.O |
| 16 | Desipramine | N06AA01 | CNCCCN1C2.–.CC.–.CC.–.C2CC3.–.CC.–.CC.–.C13•Cl |
| 17 | Gentamicin | D06AX07 | CN[C@@H](C[C@@H]1CC[C@@H](C[C@@H](O[C@@H]2C@@H](C[C@@H](C[C@@H]-([C@H](C@@H]2O)O)[C@@H]3OC[C@@H](CO)(C@H]3O)NC)C)NN)O1)NC•O.–.S(O)(O).–.O |
| 18 | Roboxetine | N06AX18 | CCOC1.–.CC.–.CC2.–.C(.–.C1)OC(C2.–.CC.–.CC.–.C2)C3CNCCO3•CS(=O)(O)=O |
| 19 | Dextromethorphan | N07XX59 | NS(=O)(CC1.–.NOC2.–.C(.–.C12)=O |
| 20 | Zonisamide | N03AX15 | CC1(O[C@@H]2CO[C@@H]3CO(C)O[C@@H]3[C@@H]2O1)COS(N(=O)=O)C |
| 21 | Topiramate | N03AX11 | COCC1.–.C2O[C@@H]3C[C@@H](C.–.C[C@@H]34CN(CC(C.–.C1).–.C24CO)O•Br |
| 22 | Galantamine | N06DA04 | CCN1.–.CC.–.CC(N2CCN(CC2)CCCCCO3.–.C4.–.C(.–.C3)CCC(N4).–.O).–.C1Cl |
| 23 | Aripreprazole | N05AX12 | CN[C@@]1(C[C@@H](S(.–.O)(C2.–.C1C.–.C(S\N).–.O)=O)S2).–.O)C•Cl |
| 24 | Dorzolamide | S01EC03 | O=C(N(C)(c(C)NC((C(O)C(O)C.–.C/N(C)C(CCCO)N(C)C(CCCO)N(C)C(CCCO)N(C)C(C)CC)- N1).–.O).–.O).–.O).–.O).–.O).–.O)N(C)C(CCCCC)C1.–.O |
| 25 | Mecamylamine | C02BB01 | CC12CC3CC(C1)(CC(C3)(C2)NC•Cl |
| 26 | Cyclosporine | L04AD01 | CC1.–.C(.–.C2C([C@H](CC(.–.C1)CC3CCN(CC4.–.CC.–.CC.–.C4)CC3.–.O)OC•Cl |
| 27 | Memaritine | N06DX01 | CC1.–.C(.–.C(N2CCCCC2.–.N1).–.O)CCN3CCC(CC4.–.NOC5.–.C4C.–.CC(F)C5)CC3 |
| 28 | Donepozil | N06DA02 | CN(CCCN1C2.–.CC.–.CC.–.C2CCC3.–.C1C.–.C(.–.C3)Cl)C•Cl |
| 29 | Risperidone | N05AX08 | CN(CCC.–.C1C2.–.CC.–.CC.–.C2C.–.CC3.–.CC.–.CC.–.C13)C•Cl |
| 30 | Clomipramine | N06AA04 | NCCN1C2.–.CC.–.CC.–.C2C.–.CC3.–.CC.–.CC.–.C13).–.O |
| 31 | Doxepin | N06AA12 | CNCC[C@@H](C1.–.CC.–.CC.–.C1)OC2.–.CC.–.CC.–.C(C(F)(F)F)C.–.C2•Cl |
| 32 | Carbamazepine | N03AF01 | NC(OCC(C1.–.CC.–.CC.–.C1)COC(N).–.O).–.O |
| 33 | Fluoxetine | N06AB03 | OC[C@@H]1C[C@@H](C[C@@H]([C@@H]2CC([C@@H](/C.–.C([C@@H](C[C@@H][C([C@@H](C/C.–.C.–.C.–.C([C@@H]OC)[C@@H]3CC[C@H]- ([C@@](O3)(CCN4CCCN(C4.–.O2).–.O).–.O).–.O)O)O)O)O)OC)C)=O)CC[C@@H]10 |
| 34 | Felbamate | N06AX10 | CC1.–.C(.–.C2CC(.–.CC.–.CC1).–.O)NC(CCC(C.–.C1).–.O)NC(C)C•Cl |
| 35 | Rapamycin | L04AA10 | C[C@@H](C1.–.CC(.–.CC(C1).–.O)NC(C)C•Cl |
| 36 | Bupropion | N06AX12 | CCN(C([C@]1(C2.–.CC.–.CC.–.C2)C[C@@H](CN).–.O)CC•Cl |
| 37 | Milnacipran | N06AX17 | COC1.–.CC.–.CC.–.C([C@@H](C2(CCCCC2)O)CN(C)C)C.–.C1 |
| 38 | Venlafaxine | N06AX16 | CIC1.–.CC.–.CC(CCC(N2CCOCC2).–.O)C.–.C1 |
| 39 | Moclobemide | N06AG02 | CC(CC(C(O)O)CNC |
| 40 | Pregabalin | N03AX16 | CICI1.–.CC2.–.C(.–.C1)OC3.–.CC.–.C2)C.–.C3N.–.C2N4CNCC4 |
| 41 | Amoxapine | N06AA17 | CC(CC(O).–.O)O•CICI.–.CC2.–.C(OC3.–.C([C@@H]4CN(C[C@H]42)C)C.–.CC.–.C3)C.–.C1 |
| 42 | Asenapine | N05AH05 | CN1CCN2C[C@@H](C3.–.CC.–.CC.–.C3C4.–.CC.–.CC.–.C2N4)C.–.C1 |
| 43 | Mirtazaoine | N06AX11 | CN(CCC.–.C1C2.–.CC.–.CC.–.C2C.–.CC3.–.CC.–.CC.–.C13)C•Cl |
| 44 | Cyclobenzaprine | N03BX08 | CN(CCC2.–.C1C2.–.CCCCC2COOCC2).–.OC.–.C1 |
| 45 | Tremadol | N02AX02 | COC1.–.CC.–.CC([C@@]2(CCCCC2C2CN(C)C).–.O)C.–.C1 |
| 46 | Ziprasidone | N05AE04 | CICI1.–.C(.–.C2CC(NC2.–.C1).–.O)CCN3CCN(C4.–.NSC5.–.CC.–.CC.–.C45)CC3 |
| 47 | Tianeprine | N06AX14 | OC(CCCCCCNC1C2.–.C(N(S(.–.O)(C3.–.C1C.–.CC(Cl).–.C3).–.O)C)C.–.CC.–.C2).–.O |

| No. | Drug Name | ATC code | Chemical structure |
|---|---|---|---|
| 48 | Buspirone | N05BE01 | O=C1CC2(CCN1CCCN3CCN(C4=NC=CC=N4)CC3)=O)CCCC2 |
| 49 | Paroxetine | N06AB05 | FC1=CC=C(C2CNCC2COC3=CC4=C(C=C3)OCO4)C=C1•Cl |
| 50 | Piracetam | N06BX03 | O=C(CN1C(CCC1)=O)N |
| 51 | Aniracetam | N06BX11 | COC1=CC=C(N2CCCC2=O)C=C1 |
| 52 | Cyclothiozide | C03AA00 | NS(=O)(C1=C(C=C2NC(C3CC4CC3C=C4)NS(=O)(C2=C1)=O)Cl)=O |
| 53 | Lamotrigine | N03AX09 | NC1=NC(N)=C(C2=C(C(Cl)=C(Cl))N=N1 |
| 54 | Levetiracetam | N03AX14 | CC[C@H](CN)=O)N1CCCC1=O |
| 55 | Perampanel | N03AX22 | O=C1C(C2=CC=CC=C2C#N)=CC(C3=CC=CC=N3)=CN1C4=CC=CC=C4 |
| 56 | Rufinamide | N03AF03 | NC(C1=CN(CC2=C(C=C(C2F)F)N=N1)=O |
| 57 | Agomalaline | N06AX22 | CC(NCCC1=CC=C(OC)C=CC2=CC=C1)=O |
| 58 | Oxandrolone | A14AA08 | C[C@@]1(C[C@H]2[C@@H]3CC[C@H]4CC(OC[C@@]4([C@H]3CC[C@]12C)C)=O)O |
| 59 | Fluphenazine | N05AB02 | OCCN1CCN(CC1)CCCN2C3=C(C=C=C3SC4=C2C=C(C(F)(F)F)C=C4 |
| 60 | Isocarboxacid | N06AF01 | CC1=CC(=C(NNCC2=CC=CC=C2)=O)=NO1 |
| 61 | Tetrabenazine | N05AK01 | O=C1C(CN2C(C1)C3=C(OC)=C(OC)C=CC3CC2)CC(C)C |
| 62 | Amisulpride | N05AL05 | CCN1CCCC1CNC(C2=CC(S(=O)(CC)=O)=C(C=C2OC)N)=O |
| 63 | Baciofen | N03BX01 | NCC(C1=CC=C(C=C1)CC(O)=O |
| 64 | Brinzolemide | S01EC04 | CCN[C@H]1CN(S(=O)(C2=C1C=C(S(N)=O)=O)S2)=O)CCOC |
| 65 | Chlormazanone | M03BB02 | CN1C(S(=O)(CC)=O)=O)C2=CC=C(C=C2)Cl |
| 66 | Entacapona | N04BX02 | CCN(C(C(#N)=C/C1=CC([N+]([O-])=O)=C(C(O)=C1)O)=O)CC |
| 67 | Ethosuximide | N03AD01 | CCC1(CC(NC1=O)=O)C |
| 68 | Flumazenil | V03AB25 | CCOC(C1=C2CN(C(C3=C(N2C=N1)C=CC(F)=G3)=O)C)=O |
| 69 | Tacrine | N06DA01 | NC1=C2CCCCC2=NC3=C1C=CC=C3•Cl•O |
| 70 | Clozapine | N05AH02 | CN1CCN(C2=NC3=C(C=CC(Cl)=C3)NC4=C2C=CC=C4)CC1 |
| 71 | Loxapine | N05AH01 | CN1CCN(C2=NC3=C(C=CC=C3)OC4=C2C=CC(=C4)Cl)CCl•O=C(OCCC(O)=O |
| 72 | Melatonin | N05CH01 | CN(C(C(#N)=C/C1=CC([N+]([O-])=O)=C(C(O)=C1)O)=O)CC |
| 73 | Miansenin | N06AX03 | CN1CCN2C(C3=C(C=CC=C=C2)=C1)NCCN3COCC3•CC4=C(N=NC(C5=CC=CC=C5)=C4)NCCN6COCC6•Cl•Cl |
| 74 | Minaprine | N06AX07 | CC1=CN=NC(C2=CC=CC=C2)=C1NCCN3COCC3•CC4=C(N=NC(C5=CC=CC=C5)=C4)NCCN6COCC6•Cl•Cl |
| 75 | Physosligmine | S01EB05 | [H][C@]12N[CC[C@]](C3=C(N2C)C=CN3C)C=CC(OC(NC)=O)=C3)C |
| 76 | Avandia | A10BD03 | O=C(OCCC(O)=O•CNS(=O)(CC1=CC=C2=C(C=C2CC3SC(NC3=O)=O |
| 77 | Sumatriplan | N02CC01 | CN(CCC=C1C2=C(C=CC=C2)SC3=C1C=C(C=C3)C)•Cl |
| 78 | Chlorprothixena | N05AF03 | CCOC1=C(CO)=OC=C(CCN[C@H](C2=CN3CCCCC3)C=CC=C2CC(O)=O)=C1 |
| 79 | Repaglinide | A10BD14 | CN1CCC(CC1)=C3C3=C(C=C(C4=CC=CC=C4)=O)SC=C3•CC#C[CH]OOO[O] |
| 80 | Ketotifen | R06AX17 | CCO(CCC1=CN=CN1CC2=C=C(C2)OC[C@@](O3)(C4=C(C=C(C4)Cl)CN5C=CN=C5)CC1)=O |
| 81 | Etamidate | N01AX07 | CCOC(N1=CC=C(C=C2)OC[C@@](O3)(C4=C(C=C(C4)Cl)CN5C=CN=C5)CC1)=O |
| 82 | Katocenazole | D01AC08 | CC[N+]([CCNC(CNNCC[N+]](CCNCC1=C(C=CC=C3)C(=C(C=CC3)Cl)CC)=O(C4=C(C=CC=C4)Cl)CC•Cl•Cl |
| 83 | Ambenonium | N07AA30 | ](CCNC(CNNCC[N+]](CCNCC1=C(C=CC=C3)C(=C(C=CC3)Cl)CC)=O(C4=C(C=CC=C4)Cl)CC•Cl•Cl |
| 84 | Valpromide | N03AG02 | CCOC(N1=O)CCC |
| 85 | Retigabine | N03AX21 | CCOC(NC1=CC=C(=C1N)NCC2=CC=C(C=C2)F)=O |
| 86 | Valnoctamide | N05CM13 | CCC(C(C)(N)=O |
| 87 | Pindoiol | C07AA03 | CC(NCC(COC1=CC=CC2=C1C=CN2)OC |
| 88 | Rivestigmine | N06DA03 | CCN(C(OC1=CC=CC([C@@H](N(C)OC)=C1)=O)C•CC#CC[CH]OOOOO[O] |
| 89 | Mifopristone | G03XB01 | [H][C@@]12CC[C@@]|C#CC)(C[C@@]1(C)[C@@H](C3=C4CC(CC=C4[C@@]23[H])=O)C5=CC=CC=C(N(C)C)C=C5)O |
| 90 | Irazodone | N06AX05 | ClC1=CC=CC(N2CCN(CC2)CCCN3N=C4C=CC=CN4C3=O)C1 |
| 91 | Pioglilazone | A10BD05 | CCC1=CN=C(C=C1)CCOC2=CC=C(C=C2)CC3SC(NC3=O)=O•Cl |
| 92 | Clonidino | N02CX02 | ClC1=CC=C(C(Cl)=C1NC2=NCCN2)•Cl |
| 93 | Chlorzoxazone | M03BB03 | ClC1=CC=C2=C(C=C1)OC(N2)=O |
| 94 | Dyphyline | R03DA01 | CN1C2=C(CN(C1=O)C)=N(C=N2)=O |
| 95 | Pizolifen | N02CX01 | CN(CC1)CCC1=C(C2=C(CC3)C=CC2C4=C3SC=C4 |
| 96 | Primidone | N03AA03 | CCC1(C2=CC=CC=C2)C(NCNC1=O)=O |
| 97 | Vincamine | C07AX07 | O=C([C@@][N1C2=C3C=CC=C(C(CC)CCCN5CCC3=C1[C@]54[H])OC |

-continued

| No. | Drug Name | ATC code | Chemical structure |
|---|---|---|---|
| 98 | Ondansetron | A04AA01 | CN1C2=C(C(CC2)CN3C=CN=C3C)=O)C4=C1C=CC=C4 |
| 99 | Tropisetron | A04AA03 | CN1[C@@H]2CC[C@@H]1CC(OC(C3=CNC4=CC=CC=C43)=O)C2•Cl |
| 100 | Bromperidol | N05AD06 | FC1=CC=C(C(CCCN2CCC(C3=CC=C(BrC=C3)(CC2)O)=O)C=C1 |
| 101 | Sibutramine | A10BG03 | CC(CC(C1C2=CC=C(=C2)Cl)CCC1)N(C)C |
| 102 | Benperidol | N05AD07 | O=C1NC2=CC=CC=C2N1C3CN(CCCC(C4=CC=CC(F)C=C4)=O)CC3 |
| 103 | (–)-Eburnamonine | C04AX17 | O=C1C[C@@]([CCC2)(CC][C@]3([H])N2CCC4=C3N1C5=C4C=CC=C5 |
| 104 | Bromocriptine | N04BC01 | O=S(C)(O)=O•[H][C@@]12CCCN1C([C@@H](N3C([C@@]([O[C@@]23O)(C)NC(C)NC([C@H]4CN-([C@@]5[C6=C(NC7=C6(C5=C4)C=C7)Br])[H])C)=O)=O)CC(C)=O |
| 105 | Carbetapentane | R05DB05 | CN1CCC[C@@H]1CCO[C@@H](C2=CC=CC=C2)(C3=CC=CC=C3)C(OC(C)=O)CC(O)=O |
| 106 | Clemestine | D04AA14 | C[N+]12CCC(OC(C3=CC=CC=C3)C4=CC=CC=C4)O)=O)C2)CC1•[Br] |
| 107 | Clidinium | A03CA02 | [H][C@@]12CCCN1C([C@@H](N3C([C@H](NC([C@@H]4CN([C@@]5(CC6=CNC7=CC(C(O)(C)=O)C(O)=OOC(C(O)C)=O)C(O)=O |
| 108 | Dihydroergotamine | N02CA01 | CC(CC(C1C2=CC=C(=C2)Cl)CCC1)N(C)C |
| 109 | Dosulepin | N06AA16 | O=C1NC2=CC=CC=C2N1C3CN(CCCC(C4=CC=CC(F)C=C4)=O)CC3 |
| 110 | Selegiline | N04BD01 | C[C@@H](N(CC#C)CC)CC1=CC=CC=C1 |
| 111 | Ethopropazine | N04AA05 | CCN(C(CN1C2)=C(C=CC=C2)SC3=C1C=CC=C3)C)C•Cl |
| 112 | Mectofenoxete | N06BX01 | ClC1=CC=C(OCC(OCCN(C)C)=O)C=C1•Cl |
| 113 | Metixene | N04AA03 | CN1CCCC(C1)CC2C3=C(C=CC=C3)SC4=C2C=CC=C4•Cl |
| 114 | Phensuximide | N03AA02 | CN1C(CCC2=CC=CC=C2)C(=O)=O |
| 115 | Procyclidine | N04AA04 | OC(C1CCCCC1)(C2=CC=CC=C2)CCN3CCCC3•Cl |
| 116 | Chlorpromazine | N05AA01 | CN(CCCN1C2)=C(C=CC=C2)SC3=C1C=CC=C3)C)C |
| 117 | Biperiden | N04AA02 | BrC1=C(NC=C)OC(C(NCCN)(CC)CC)C4 |
| 118 | Thiethylperazine | R06AD03 | CCSC1=CC2=C(C=C1)SC3=C(N2CCCN4CCN(CC4)C=CC=CC=C3•OC(CC(O)=O)C(O)=O |
| 119 | Tranylcypromine | N06AF04 | N[C@@H]1CC1C2=CC=CC=C2•Cl |
| 120 | Glipizide | A10BB07 | CC1=CN=C(NNCCC2=CC=C(S(=O)NC(NCSCCCCG3)=O)=O)C=C2)=O)C=N1 |
| 121 | Perphenazine | N05AB03 | OCCN1CCN(CC1)CCCN2=C1(CN(C1=O)C)=O)NC=N2•NCCN•CN3C4=C(C(N(C3=O)C)=O)NC=N4 |
| 122 | Aminophyline | R03DA05 | NCCN•NC1=C2N=CN(C2=C(N(C1=O)C)=O)C)=CC=C2)C=O |
| 123 | Sulpiride | N05AL01 | CCN1CCCC1CNC(C2=CC(S(N)(=O)=O)=CC=C2OC)=O |
| 124 | Banzhexol | N04AA01 | OC(C1CCCCC1)(C2=CC=CC=C2)CCN3CCCCC3•Cl |
| 125 | Bromopride | A03FA04 | BrC1=C(NC=C(OC(C(NCCN)(CC)CC))=O)C1 |
| 126 | Amentadine | N04BB01 | NC12CC3CC(C2)CC(C1)C3 |
| 127 | Nialamido | N06AF02 | O=C(NCC1=CC=CC=C1)CCNNC(C2=CC=NC=C2)=O |
| 128 | Fluspiriene | N05AG01 | FC1=CC=C(C(C2=CC=C(F)C=C2)FCCCN3CCC4(N(C5=CC=CC=C5)CNC4=O)CC3)C=C1 |
| 129 | Furosamide | C03CA01 | NS(=O)(C1=CC=C(C(O)=O)=C(Cl)NCC2=CC=CO)=O |
| 130 | Droparidol | N05AD08 | FC1=CC=C(CCCN2CCC(N3C(NC4=C3C=CC=C4)=O)=CC2)C=C1 |
| 131 | Promazine | N05AA03 | CN(CCCN1C2=C(C=CC=C2)SC3=C1C=CC=C3)C•Cl |
| 132 | Pimezide | N05AB04 | FC1=CC=C(C(C2=CC=C(F)C=C2)FCCCN3CCC(N4(NC(NC5=C4C=CC=C5)=O)CC3)C=C1 |
| 133 | Tiapride | N05AL03 | O=C(NCCN(CC)CC)C1=CC(S(=O)(C)=O)=CC=C1OC•Cl |
| 134 | Prochlorperazine | N06AB04 | O=C(/C=C/O)=O)•CN1CCN(CC1)CCCN2C3=C(SC4=CC=C(C=C24)Cl)C=CC=C3 |
| 135 | Trimipremine | N06AA06 | CC(CN1C2)=C(C=C=C2)CCC3=C1C=CC=C3)CN(C)C•O/C=C/C(O)=O |
| 136 | Paliperidone | N05AX13 | O=C1N2CC[C@@H](CCCN2)O)=NC(O)=C1CCN3CC(CC3)C4=NOC5=C4C=CC(F)=C5 |
| 137 | Quetiapine | N06AH04 | OCCOCCN1CCN(CC2N3=CC=CC=C3SC4=CC=CC=C24)CC1•OC(/C=C/C(=O)=O)=O |
| 138 | Enalapril | C09AA02 | O=C([C@@H](N[C@H](CCN1CCC[C@H]1C(O)=O)C)CC2=CC=CC=C2)=O |
| 139 | Synephrina | C01CA08 | CNCC(C1=CC=C(O)C=C1)O |
| 140 | Itopride | A03FA07 | COC1=C(OC)C=C(NC2=CC(NCC3=CC=C(C13)=O)=O)C=C1 |
| 141 | Oxcarbezepine | N03AF02 | NC(N1C2=CC=CC=C2C(CC3=CC=CC=C13)=O)=O |
| 142 | Iioperidone | N05AX14 | COC1=C(OCC(C)=O)C=C(C1OCCNH2CCC(C3=NOC4=C3C=CC(F)=C4)CC2 |
| 143 | Sparterine | C01BA04 | N12CCCCC[C@@H][CN3CCCCC[C@@H]43]C[C@@H]4C2 |
| 144 | Sorafenib | L01XE05 | CNC(C1=NC=C(OC2=CC=C(=C2)NC(NC3=CC(C(F)(F)F)=C(Cl)C=C3)=O)C=C1)=O |
| 145 | Domperidone | A03FA03 | ClC1=CC2=CN(CN2)=O)C3CCN(CC3)CCCN4C5=CC=CC=C5NC4=O)C=C1 |
| 146 | Claboprid | A03FA06 | ClC1=C(N)C=C(C(NC2CCN(CC2)CC3=CC=CC=C3)=O)C1•OC(CC(O)=O)C(O)=O |

-continued

| No. | Drug Name | ATC code | Chemical structure |
|---|---|---|---|
| 147 | Procaine hydochloride | C05AD05 | CCN(CCOC(C1=CC=C(C=C1)N)=O)CC•Cl |
| 148 | (−)-Epigallocatechin gallate | D06BB12 | O=C(C1=CC(O)=C(O)C(O)=C1)O[C@@H]2CC3=C(C=C(C=C3O)O)O[C@@H]2C4=CC(O)=C(O)C(O)=C4 |
| 149 | Idebenone | B04BC04 | CCCN(CCC1=C2CC(NC2=CC=C1)=O)CCC•Cl |
| 150 | Thioridazine | B06BX13 | O=C1C(CCCCCCCCO)=C(OC(OC)=C1OC)=O |
| 151 | Nefazodone | N05AC02 | CSC1=CC2=C(C=C1)SC3=CC=CC=C3N2CCC4CCCN4C•Cl |
| 152 | Guanfacine | N06AX06 | CCC1=NN(C(N1CCOC2=CC=CC=C2)=O)CCCN3CCN(C4=CC(Cl)=CC=C4)CC3•Cl |
| 153 | Rasagiline | C02AC02 | NC(NC(CC1=C(C=CC=C1Cl)Cl)=O)=N—Cl |
| 154 | Vinpocetine | N04BD02 | C#CCN[C@@H]1CCC2=CC=CC=C12 |
| 155 | Nicergoline | N06BX18 | O=C1=C[C@@](CCC2)(CC)[C@@H]3N2CCC4=C3N1C5=CC=CC=C45)OCC |
| 156 | Fipexide | C04AE02 | CO[C@]12C[C@H]CN[C@@H]1CC3=CN(C4=CC=CC2=C34)C)COC(C5=CC(Br)=CN=C5)=O |
| 157 | Propentofylina | N06BX05 | ClC1=CC=C(OCC(N2CCN(CC3=CC4=C(OCO4)C=C3)CC2)=OC=C1•Cl |
| 158 | Oxiracetam | N06BC02 | O=C(N1CCCCC(O)=O)N)CC2=C(N(CCCC)C=N2)C1=O |
| 159 | Pyrithioxine | N06BX07 | O=C1N(CC(CC1O)=O)N |
| 160 | Progabide | N06BX02 | OC1=C(O)N=CC(SSCC2=C(CO)(CO)=C(O)N=C2)=C1CO |
| 161 | Ataluren | N03AG05 | NC(CCCN)C1=CC=C(CC2=NOC(C3=CC=CC=C3F)=N2)=C1)O |
| 162 | Sapropterin | M09AX03 | O=C(C1=CC=C(C2=NOC(C3=CC=CC=C3F)=N2)=C1)O |
| 163 | Trifluoperazine | A16AX07 | CC(O)[C@H](O)C1CNC2=C(N1)C(N=N(N)N2)=O•Cl |
| 164 | Flunarizine | N05AB06 | CN1CCN(CCCN2C3=CC=C(=C1)C(N2CCN(C=C=C3=CC=CC=C(=C4)C(F)(F)F)CC1•Cl |
| 165 | Levosulpiride | N07CA03 | FC1=CC=C(C(N2CCN(C=C=C3=CC=CC=C3OC2)C4=CC=C(F)C=C4•Cl |
| 166 | Desvenlafexine | N05AL07 | CN1CCC[C@H]1CNC(C2=CC=CC(S(N(=O)=O)=C2)OC)=O |
| 167 | Chlorpheniramine | N06AX23 | CN(CCC(C1=CCCCC1)OC2=CC=C(C=C2)OC=C(C2O)C |
| 168 | Lurasidone | R06AB04 | CN(CCC(C1=CC=CC=N1)C2=CC=C(C=C2)Cl)C•O=C(O)C=C1C(O)=O |
| 169 | Remoxipride | N05AE05 | O=C1[C@H]2[C@@H]3CC[C@H][C@H]2CN1C[C@@H]2CN1C[C@@H]4CCC[C@@H]4CN5CCN(C6=NSC7=CC=CC=C67)CC5)=O)C3•Cl |
| 170 | Kelorolac | N05AL04 | CN1CCC[C@H]1CNC(C2=CC=C2C(=CC(Br)=C2OC)OC)=O•Cl |
| 171 | Tizanidine | M01AB15 | OC(C1CCN2C1=CC=C2C(23=N5N=C2C=C1)NC3=NCCN3•Cl |
| 172 | Serlindote | M03BX02 | ClC1=C(C2=N5N=C2C=C1)NC3=NCCN3•Cl |
| 173 | Molindone | N05AE03 | FC1=CC=C(N2C=C(C3=C2C=CC(Cl)=C3)C4CCN(CC4)CCN5CCNC5=O)C=C1 |
| 174 | Vorlioxetine | N05AE02 | CC1=C(CC2=C(NC2=C1C(CCC2)N3CCNCNC3CCOCC3)=O)C•Cl |
| 175 | Excitalopram | N06AX26 | CC1=C(OC2=C(C=C2)N3CCNCC3)NC=CC(O)=C1•Br |
| 176 | Flumazenil | N06AB10 | CN(CCC[C@@]1(C2=CC=C(C=C2)F)OCC3=C1C=CC(C#N)C3)C•O=C(O)C(O)=O•O |
| 177 | Alphaxalone | V03AB25 | CCOOC(C1=C2NC(C3=C(N2C=N1)C=C(F)=C3)=O)C=O |
| 178 | Etifoxine | N01AX05 | O=C1[C@H]2[C@@H](CC[C@@H]3C[C@@H]23C)O)[C@@H]4CC[C@@H](CC[C@@H]4(C1)C)(C)C)=O |
| 179 |  | N05BX03 | ClC1=CC=C2N=C(OC(O)(C2=C1)C3=CC=CC=C3)NCC•Cl |

With reference to FIGS. 12A to 12C and 13, it is also observed that the drug treatment did not affect the health of the animals, as ~95% of larvae remained alive and healthy when released from the system. The majority of the drugs tested (91.6%) did, indeed, induce acute changes in zebrafish brain function with reproducible BAM patterns and, accordingly, T-score BAMS unique to that drug.

Figure 12A:
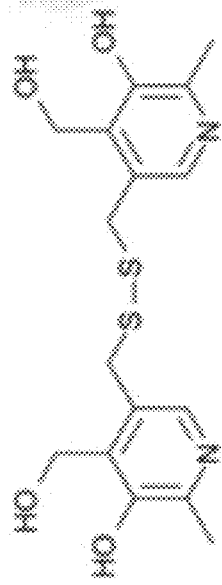
FIGS. 12A to 12C illustrates respectively T-score BAMs showing the regulation of brain physiology induced by different CNS drugs including Loxapine, a dibenzoxazepine-class typical antipsychotic; Pyrithioxine, a synthetic, dimeric, disulfide bridged, derivative of vitamin B6 (Pyridoxine) with psychostimulant/nootropic activity; and Ethopropazine, a phenothiazine derivative with anti-cholinergic, antihistamine, and anti-adenergic activities used as an anti-parkinsonian medication.
Figure 12B:
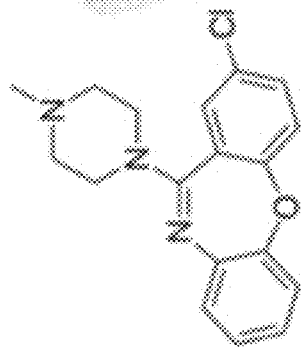
Figure 12C:
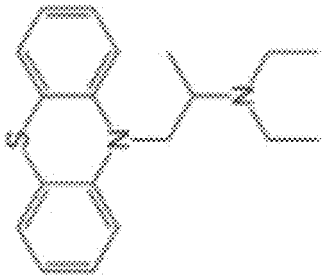
Figure 13:
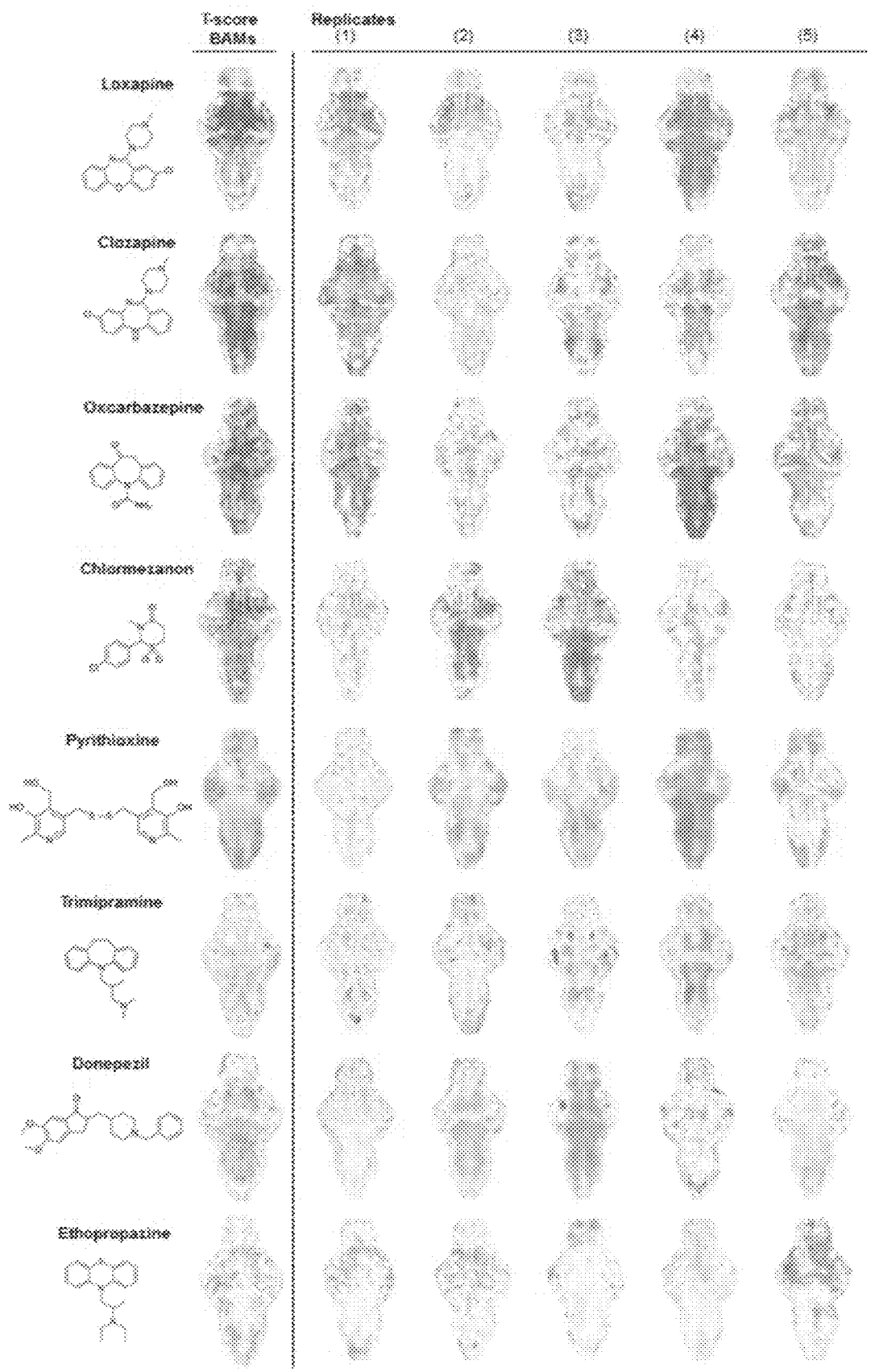
FIG. 13 illustrates T-score BAMs generated by drugs of both similar and varying structure, the BAM to the right of the compounds is the composite map from the five replicates BAMs depicted on the right for each larvae.
Figure 14:
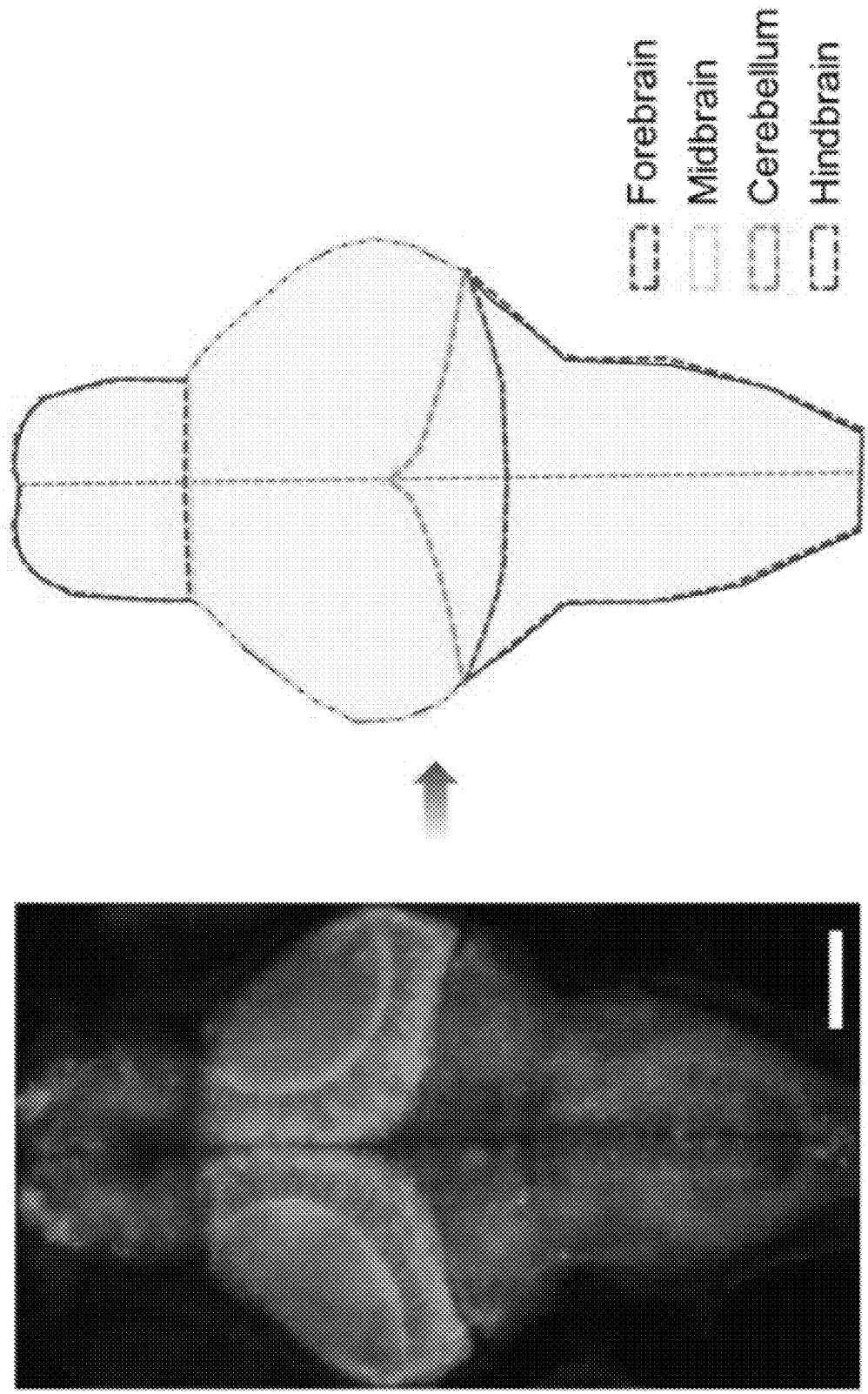
FIG. 14 is an image and a corresponding illustration of the larval zebrafish brain in the selected uniform template, with major brain regions labelled using the dotted line with different colors, the scale bar is 100 μm.

For example, referring to FIGS. 12A and 14 loxapine, a typical antipsychotic drug, resulted in increased neural activity in the forebrain but marked decrease in spikes elsewhere in the brain, whereas pyrithioxine, a psychostimulant, increased activity brain-wide as shown in FIG. 12B, and ethopropazine, used to treat extrapyramidal symptoms in patients with Parkinson's disease, induced robust upregulation in neural activity only in the forebrain and hindbrain as shown in FIG. 12C.

Collectively, these results support that BAMs provide a spatially and functionally encoded phenotype directly associated with therapeutic potential of different (or different types of) CNS drugs. To investigate this further, the inventors have tested a larger collection of bioactive compounds.

Preferably, the BAMs provide a functional description of the therapeutic potential of CNS drugs, it may be further assumed that similar BAMs would have an association with a functional drug category that covers a set of compounds, regardless of their chemical structures or molecular mechanisms.

Figure 15:
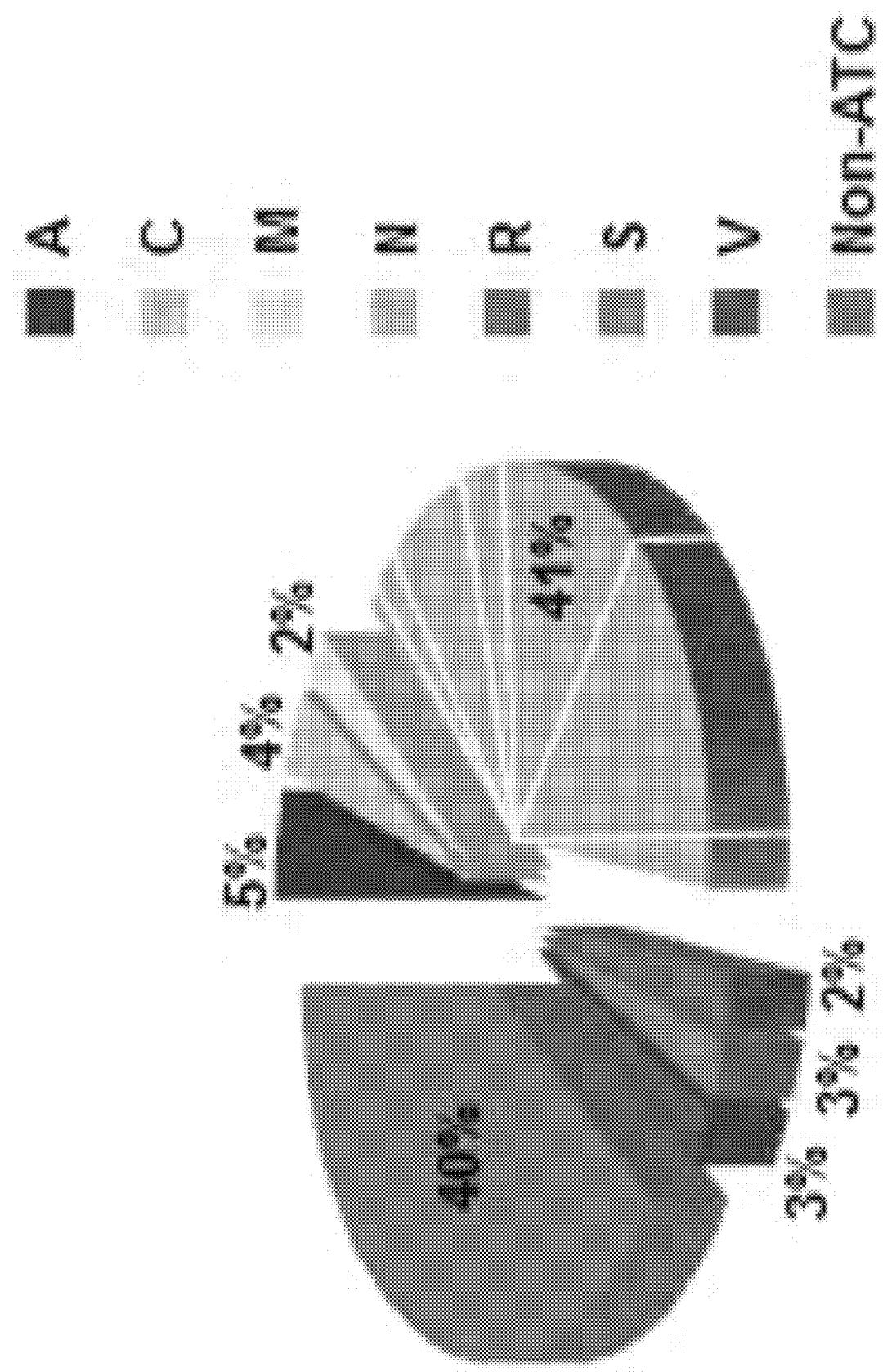
FIG. 15 is a chart showing a distribution of the drug library containing clinically used drugs (with ATC codes) and non-clinical compounds, the abbreviations are: A, alimentary tract and metabolism; C, cardiovascular system; M, musculo-skeletal system; N, nervous system; R, respiratory system; S, sensory organs; V, various; Non-ATC, compounds without ATC codes.

With reference to FIG. 15 and the above Table showing the list of the clinical drugs, the complete set of T-score BAMs from the 179 clinical drugs spanning a total of seven different functional categories defined by the WHO ATC system was analyzed. The processing module may further apply principle component analysis (PCA) to decompose the plurality of T-score maps into a plurality of characteristic features of the BAM patterns. Once these characteristic patterns were extracted from all the T-score BAMs, the principle components (PCs) were used to define a multi-dimensional vector space, in which each T-score BAM was projected onto the PC vector space by assuming a linear combination of all PCs.

The processing module 112 and/or the transformation module 106 may be implemented using a computer or a computer server. The computer may comprise suitable components necessary to receive, store and execute appropriate computer instructions, such that when these computer instructions are executed by the processing unit in the computer device, the these modules are operable to process the image data provided from the imaging module and is capable of predicting a neuropharmacology of the neuroactive compound based on the raw image data obtained.

With reference to FIG. 16, the top 20 PCs that accounted for the major pattern variation (>50%) across all T-score BAMs were identified, and subsequently used to reconstruct the T-score BAMs while minimizing background noise.

Figure 17:
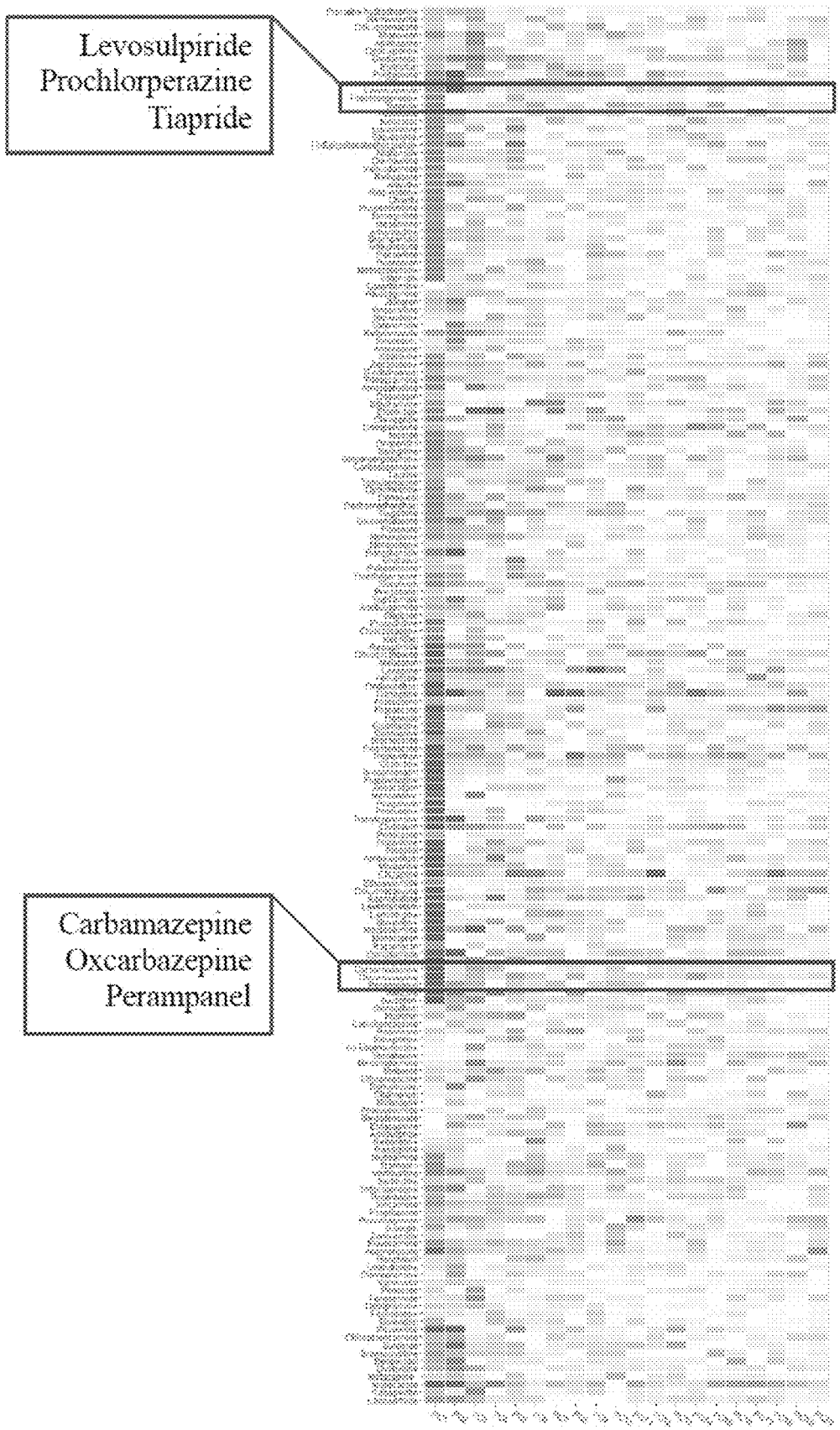
FIG. 17 is a chart showing 20-dimensional pheno-print vectors (characterized by the top 20 PCs) for 179 clinical drugs.

After decomposition into the PCs, each characteristic T-score BAM was converted to a dimensionality-reduced "Pheno-Print" represented by a 20-dimensional vector, referring to FIG. 17.

Figure 18:
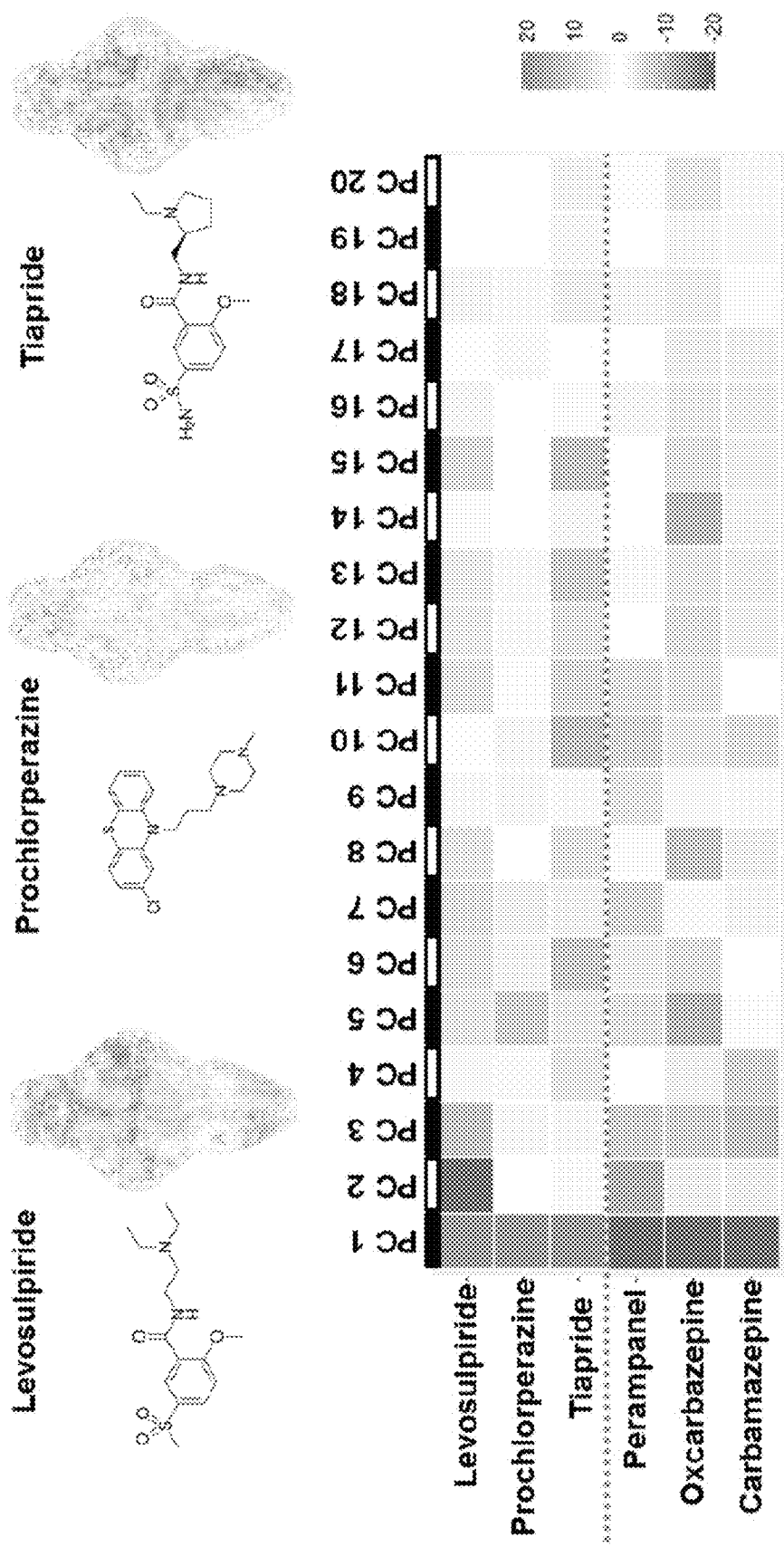
FIG. 18 shows examples of some functionally related drugs that share similar pheno-print vector, the Chemical structures and T-score BAMS of three drugs with similar pharmacological effects, including levosulpiride, prochlorperazine and tiapride; and Pheno-prints of different drugs with indicated locations in FIG. 17, including levosulpiride, prochlorperazine, tiapride, perampanel, oxcarbazepine and carbamazepine.
Figure 19:
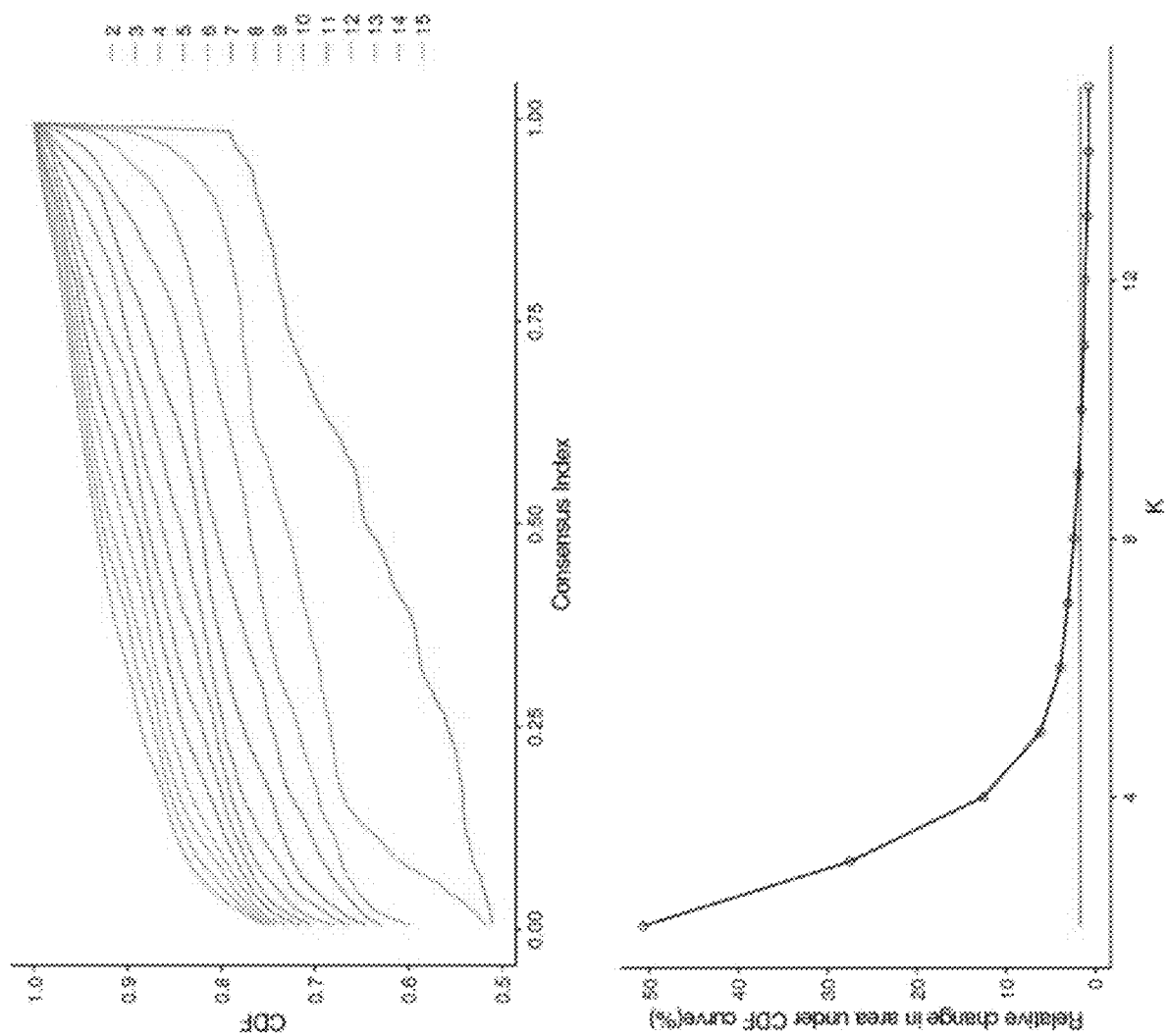
FIG. 19 are plots showing identification of the 10 optimal clusters based on consensus clustering; the upper plot shows empirical cumulative distribution function (CDF) for different numbers of clusters ranging from 2 to 15, and the lower plot shows relative changes in area under the CDF curve as the number of clusters (K) increase from 2 to 15, When K increases from 10 to 11 and so on, the area under the CDF curve does not increase substantially (<1%), as indicated by the red line.
Figure 20:
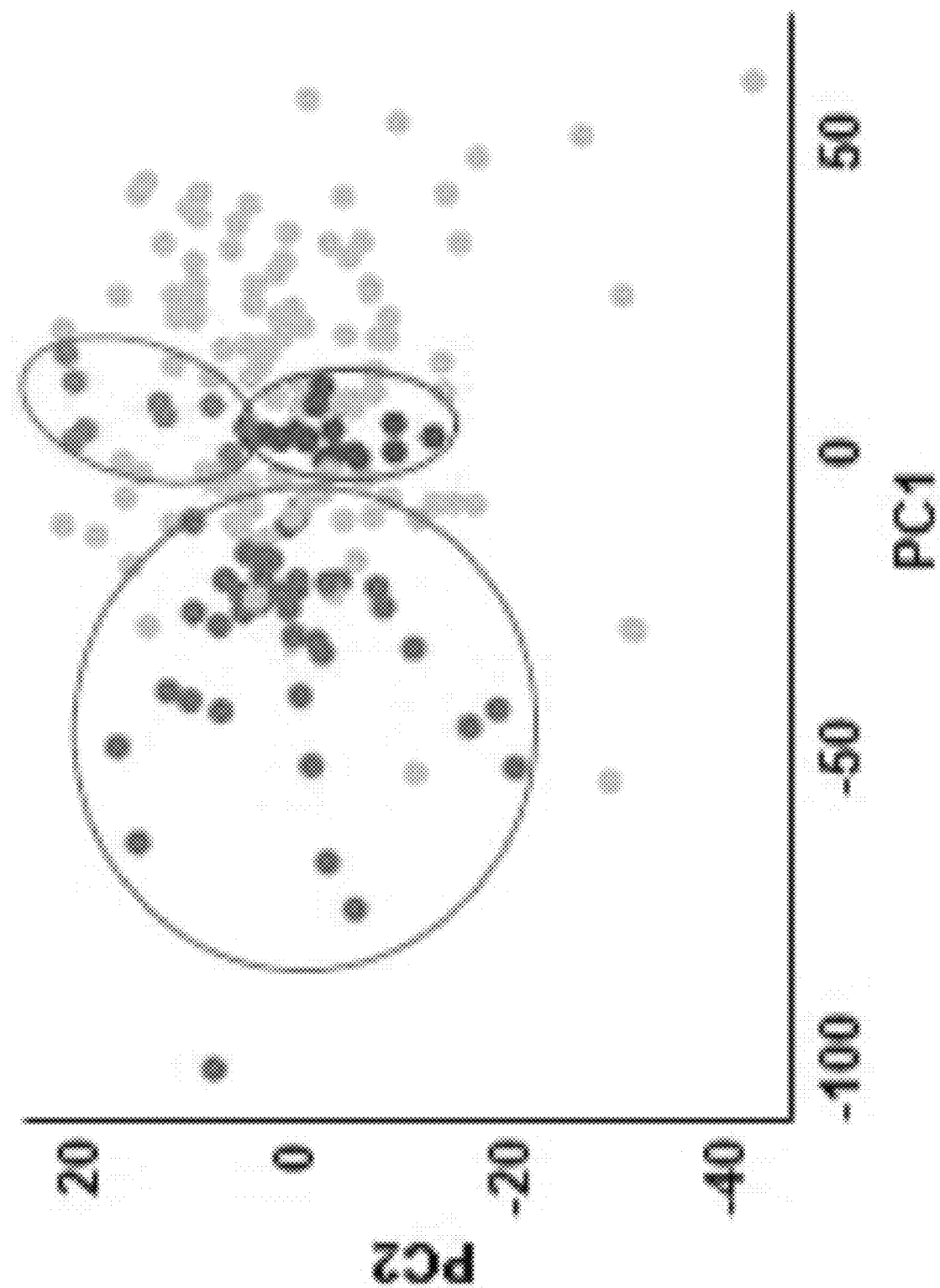
FIG. 20 is a plot showing visualization of the coherence for the 179 drugs in a two-dimensional space constructed by the first two principle components (PCs)

With reference to FIGS. 18 to 19, it is observable that some functionally related drugs shared similar Pheno-Prints. For example, levosulpiride and tiapride, two D2 dopamine receptor antagonists with similar chemical structures that are both used clinically to treat psychiatric disorders, had similar Pheno-Prints. In addition, their Pheno-Prints are similar to that of prochlorperazine, another D2 dopamine receptor antagonist antipsychotic drug with a very different chemical structure than either levosulpiride or tiapride.

The processing module 112 is further arranged to generate the functional classifiers based on the plurality of characteristic features obtained by a supervised clustering processing or an unsupervised clustering processing. Referring to FIG. 19, unsupervised classification may be applied to detect, in blinded fashion, the intrinsic coherence among similar T-score BAMs, subsequently defined as functional clusters of the tested drugs. Specifically, consensus clustering 21 may be applied to the library of Pheno-Prints (in 20 dimensions) corresponding to the 179 clinical drugs.

With reference to FIGS. 20 to 23, as visualized in a two-dimensional space constructed by the first two PCs, some major BAM clusters (e.g. clusters 3, 4, and 8) may be observable. Pheno-Print clustering led to the identification of ten BAM clusters. For each cluster, the T-score maps for in-cluster drugs were averaged to derive a representative cluster pattern. It may be also observed that, while the BAM clusters were relatively distant from each other, there was substantial coherence within each individual BAM cluster for in-cluster drugs.

Figure 23:
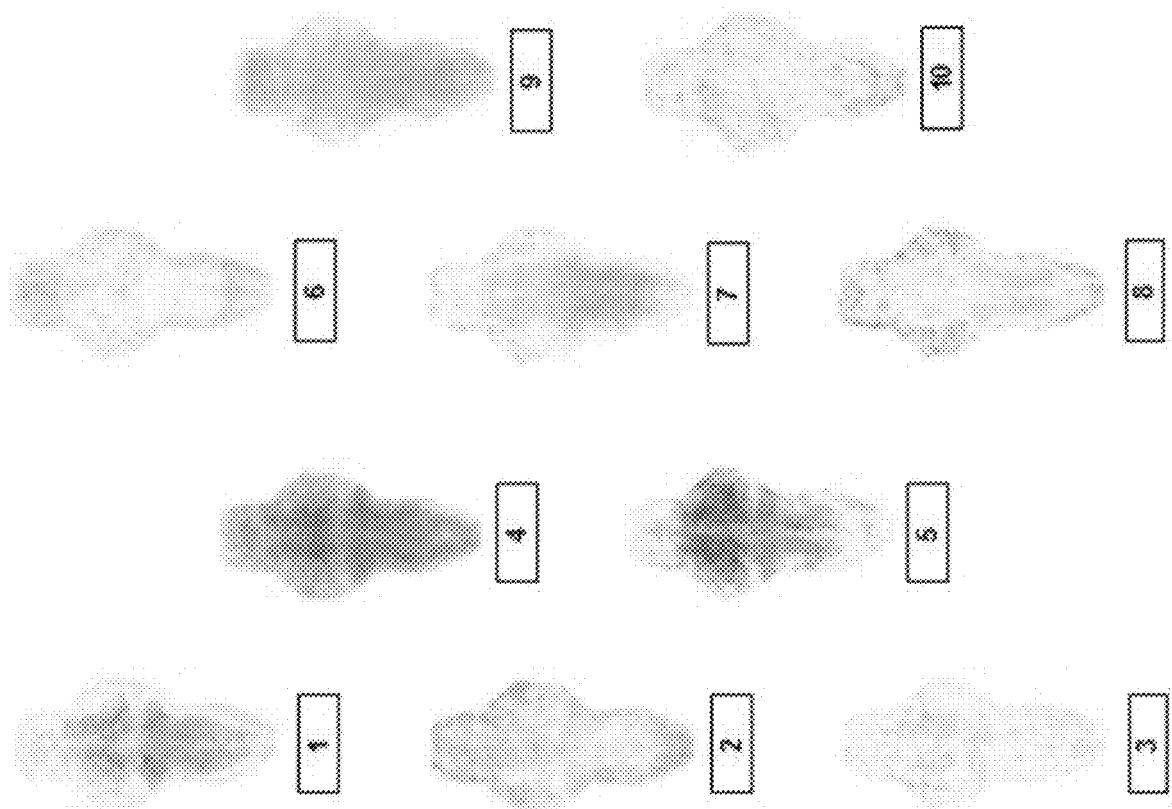
FIG. 23 are illustrations of representative cluster patterns derived by taking mean of all T-score BAMS for drugs in the ten BAM clusters identified.

Using the T-score BAMs for the training set of 179 clinical drugs, unsupervised classification may be employed to dissect the phenotypic diversity. First, to reduce the dimensionality and noise, principal component analysis (PCA) was applied to all T-score BAMs. The top 20 principal components (PCs) were used to construct the Pheno-Prints for further analysis. Next, with reference to FIG. 21, consensus clustering based on hierarchical clustering with bootstrap resampling (n=1000) 21. 10 optimal phenotypic BAM clusters were identified, as the area under the empirical cumulative distributions functions (CDF) curve did not increase substantially (<1%) from 10 to 11 clusters, and so on, as shown in FIG. 19. For each BAM-cluster, a representative cluster pattern as shown in FIG. 23 was calculated by taking the mean of the T-score BAMs over all in-cluster compounds.

A one-tailed Wilcoxon signed-rank test may be performed for each drug, which showed that the Pheno-Prints of within-cluster drugs are significantly (FDR-adjusted $P<10^{-5}$ for all drugs) different than the Pheno-Prints of out-of-cluster drugs. For any drug in a particular cluster, its averaged in-cluster consensus score (the mean of the consensus scores by pairing the drug with every other drug in the same cluster) is significantly higher (FDR-adjusted $P<10^{-5}$ for all drugs) than the averaged out-of-cluster consensus score (the mean of the consensus scores by pairing the drug with every drug outside the cluster), suggesting that the common features of BAMs could be related to specific effects on CNS physiology shared among those in-cluster drugs.

Figure 24:
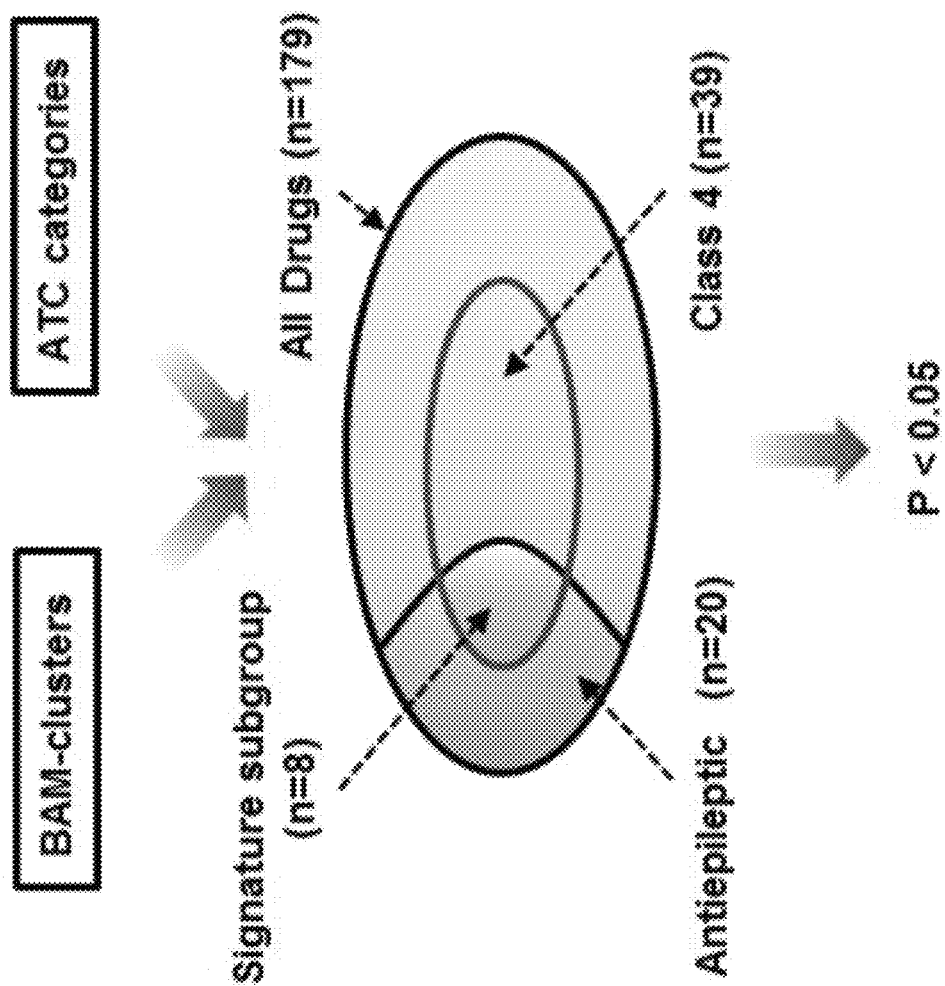
FIG. 24 is an illustration showing schematics of the hypergeometric test for overrepresentation of a specific ATC category by a phenotypic BAM-cluster.

Next, the relationship between the BAM clusters and the therapeutic function of the 179 compounds in the library and the clinical use(s) of the compounds classified by the WHO ATC system may be identified. To avoid over-representation of ATC categories by the identified BAM clusters, referring to FIG. 24, a hypergeometric test may be performed for statistical analysis of the link between the two systems, which uses a discrete probability distribution to calculate the statistical significance of the subgroup overlaps and is an established method to determine whether a sub-population (e.g., drugs belonging to an ATC category) is overrepresented in a sample (e.g., drugs of a BAM cluster).

To link identified phenotypic BAM clusters to therapeutic drug categories, hypergeometric tests were performed for over-representation. In the test for over-representation of an ATC category in a BAM cluster, the hypergeometric p-value is calculated as the probability of observing k or more drugs of an ATC category (from the whole population of all 179 drugs in the training set) in total n drugs of a specific BAM cluster. For each pair of BAM cluster and ATC category, the resulting P-values were used to identify nominally statistically significant associations (P<0.05). For ATC-associated BAM clusters, the significant overlap between a BAM-cluster and an ATC category was defined as the signature subgroup.

To predict the therapeutic function of non-clinical compounds in the test set, a two-step prediction strategy may be used. First, a random forest classifier was built using R package 'randomForest' (with parameter ntree set to 100) based on the clustering results from the training set of 179 clinical drugs, in order to classify the 121 non-clinical compounds into the 10 phenotypic BAM clusters. For this purpose, all T-score BAMs of the test set were projected to the PC space of the training set to derive their Pheno-Prints and used as inputs for the classifier. Secondly, for compounds that were relegated to ATC-associated BAM clusters, the prediction was further prioritized based on the Pearson correlation coefficient between each compound's Pheno-Print and the signature subgroup's centroid in the PC space.

Figure 25:
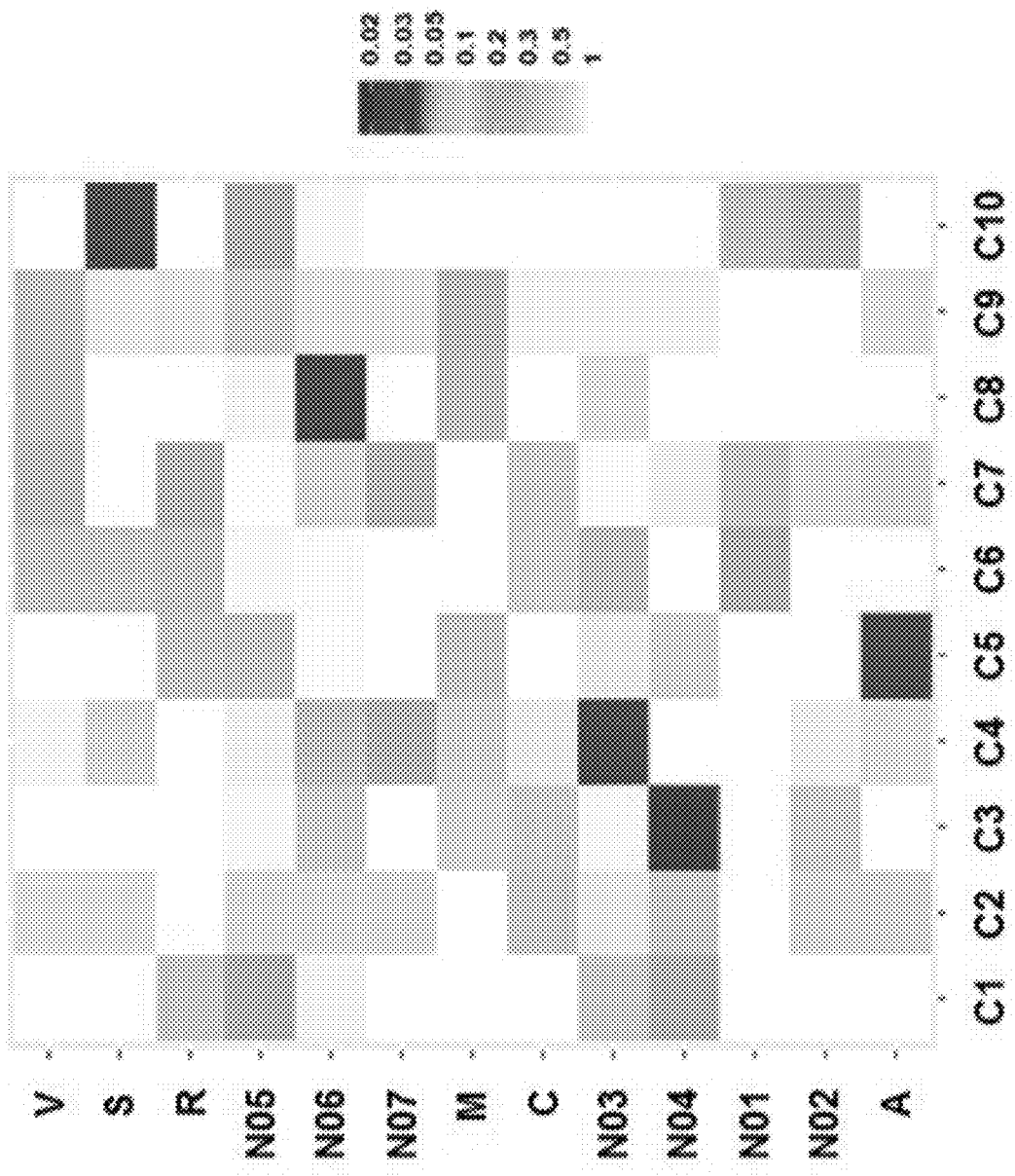
FIG. 25 is a heat map illustrating statistical associations between ATC categories and identified BAM-cluster, the Color coding is based on p-values derived from the hypergeometric tests (red: lower P-values or more significant association; gray: higher p-values or less significant association)
Figure 26:
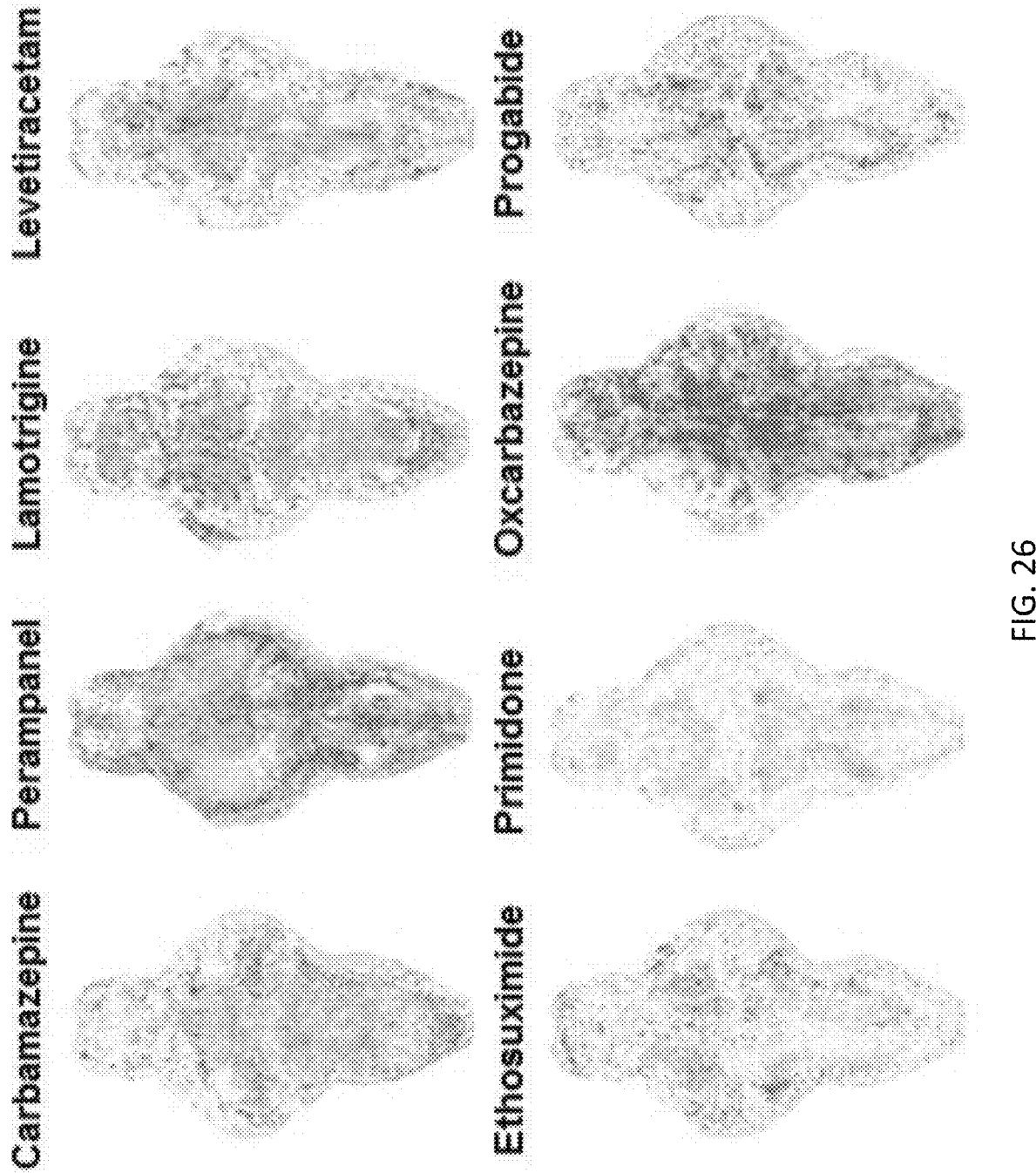
FIG. 26 are the T-score BAMS of the drugs in the signature subgroup of cluster 4, which is significantly associated with N03:Anti-epileptics ATC category.

With reference to FIG. 25, several BAM clusters (e.g. clusters 3, 4, and 8) were found to have significant overlap with different ATC categories (e.g. N04:Anti-parkinson drugs, N03:Anti-epileptics and N06:Psychoanaleptics) (P<0.05, hypergeometric tests). In particular, BAM cluster 4 was found to have a strong association with N03:Anti-epileptics ATC category, with a signature subgroup of eight drugs within the cluster that resulted in inhibition of activity across almost the entire brain. Referring to FIG. 26, this signature subgroup is comprised of carbamazepine, oxcarbazepine, perampanel, lamotrigine, levetiracetam, ethosuximide, primidone, and progabide.

With reference to FIG. 27, within this signature subgroup that clustered together, the structurally similar compounds are thought to exert their clinical effects through binding to a common molecular target, such as the structurally related sodium channel blockers carbamazepine and oxcarbazepine. More compelling, however, was the observation that compounds with significant diversity in their chemical structure and molecular mechanism also appeared in this signature subgroup. Notably, some compounds (e.g. levetiracetam and piracetam) with similar chemical structures, but different ATC-category based therapeutic functions, were successfully differentiated by their distinct BAMS.

Despite their similar chemical structures, referring to FIG. 28, levetiracetam and piracetam are employed in different clinical applications; levetiracetam (N03AX14) is a broad-spectrum anti-epileptic drug that affects neuronal signaling by binding to and affecting synaptic vesicle glycoprotein 2A (SV2A) function, whereas piracetam (N06BX03) is an allosteric modulator of the AMPA receptor and has been recognized for putative effects as a cognitive enhancer and an adjunctive agent for myoclonus in case reports 22.

The BAM-based clustering successfully separated these two drugs into distinct BAM clusters (clusters 4 and 8) associated with the different ATC categories of N03:Anti-epileptics and N06: Psychoanaleptics, respectively.

Preferably, the processing module 112 further predicts a neuropharmacology of the neuroactive compound based on the association, using a statistical analysis and/or a machine learning process for processing the acquired brain activity maps. Advantageously, the computationally identified association of BAM clusters with clinical ATC categories reveals a drug screening strategy that is based purely on brain physiology, which does not require any prior knowledge of chemical structure or molecular target. For an unknown compound, the relegation of its functional activity map to an ATC-associated BAM-cluster would indicate higher probability for the compound to be a hit for that particular ATC category.

The BAM cluster method may be further validated by predicting the neuropharmacology of an additional "test set" comprised of 121 compounds currently without ATC codes, as shown in the Table below.

| No. | Drug Name | ATC code | Chemical Structure |
|---|---|---|---|
| 1 | Tubestatin A | no entry | O=C(C1=CC=C(CN2C3=C(C4=C2C=CC=C4)CN(C)CC3)C=C1)NO•Cl |
| 2 | NADH | no entry | NC(C1=CN([C@H]2O[C@@H](C(C2)O)COP(OP(OC[C@@H]3O[C@H](N4C=NC5=C(N=CN=C45)N)C(C3O)O)(O[K])=O)(O[K])=O)C=CC1)=O |
| 3 | CX-546 | no entry | O=C(C1=CC2=C(OCCO2)C=C1N3CCCCC3 |
| 4 | CX-614 | no entry | O=C(C1=CC2=C(OCCO2)C=C1O3)N4C3CCC4 |
| 5 | Ibutamoren | no entry | O=S(C)(N1CC2(CCN(C(C(COC3=CC=CC=C3)NC(C(CN)=O)=O)CC2)C4=CC=CC=C4)=O |
| 6 | AL-108 | no entry | Asn-Ala-Pro-Val-Ser-Ile-Pro-Gln |
| 7 | Ethoxzolamide | no entry | CCOC1=CC2=C(N=C(S(N)(=O)=O)S2)C=C1 |
| 8 | NBI-31772 | no entry | O=C(C(N)N1[C@@](CN[C@H](C(O)=O)C3)O)=N1)C(C(O)C(O)=C2)O•O |
| 9 | NNZ-2586 | no entry | O=C(C(N)N1[C@@](CN[C@H](C(O)=O)CCC(O)=O)=O)C(CC1•Cl |
| 10 | Theanine | no entry | O=C([C@H](CCC(NCC)=O)N)O |
| 11 | IDRA-21 | no entry | CC(N1)NC2=CC=C(C=C2S1(=O)=O)Cl |
| 12 | BIX-02194 | no entry | COC1=CC=C/C=N/C(C=C1)=NC(N3CCN(CCC3)=NC(N4CCN(CC4)CC5=CC=C(C=C5)=C2C=C1OC•Cl•Cl |
| 13 | Tebimorelin | no entry | CCNN(C=C/N(C(OH)(CC1=CC=C(C=C2=C1CN(C@H](CC3=CC=CC=C3)(NC)=O)C)=O)C=O)C•O |
| 14 | Pimevanserin | no entry | CC(COC1=CC=C(C=C1)CN(C2=CN(CC2)=OCC3=CC=C(C=C3)F)=O)C=C1)C |
| 15 | DOV-216,303 | no entry | CIC1=CC=C(C23CNCCC2C3)C=C1Cl•Cl |
| 16 | Bicifadine | no entry | CIC1=CC=C(C23CNCCC2C3)C=C1•Cl |
| 17 | Indatreline | no entry | CNC1CC(C2=CC=C(C1)C(C1)=C2)C3=C1C=CC=C3•Cl |
| 18 | GYKI-52466 | no entry | CC1=NN=C(C2=CC=C(N)C=C2)C3=CC4=C(OCO4)C=C3C1•Cl |
| 19 | Fanapaner | no entry | FC(F)(F)C1=CC(N(C(N2CP(O)(O)=O)=O)=O)=C2C=C1N3CCOCC3 |
| 20 | BIMU-8 | no entry | O=C(N1C2=CC=CC=C2N(C(C)C)C1=O)N3C[C@@]([N4C)[H])CC[C@@]4[H])C3•Cl |
| 21 | 1,8-Dihydroxyflavone | no entry | O=C1C=C(C2=CC=CC=C2)OC3=C1C=CC(O)=C3O |
| 22 | Gaboxadol | no entry | OC1=NON2=C1CCNC2•Cl |
| 23 | LM22A-3 | no entry | CC(NC1=CC=C(/C=C(C2=NN(CCO)C(N)=C2C#N)C#N)C=C1)=O |
| 24 | LM22A-4 | no entry | O=C(NC1=CC=CC(NCCO)=NC=CC(NNCO)=O)=C1)NCCO |
| 25 | (+)-Bicuculline | no entry | CN1CCC2=CC=C3=C2[C@H]1[C@@H]4OC(C5=CC=C(C=C6=C5OCO6)=O)OCO3 |
| 26 | Nisoxetine | no entry | CNCC(OC1=CC=CC=C1OC)C2=CC=CC=C2•Cl |
| 27 | Vanoxerine | no entry | FC1=CC=C(C=C1)C(OCCN2CCN(CC2)CCC3=CC=CC=C3)C4=CC=C(C=C4)F•Cl |
| 28 | Forskolin | no entry | [H][C@@]1(CCC(C)(C)[C@@]2([C@@H]2[C@@H](O)[C@@]3(O[C@@])OC([C@@]3(O[C@@](C[C@@]12C)O)=C)(C)C)[H]])[H])CO |
| 29 | AR-A014418 | no entry | O=C(NCC1=CC=C(OC)C=C1)NC2=NC=C(N+)[O-])=OS2 |
| 30 | ING-135 | no entry | O=C1C(C2=CN(C)C3=CC=C(Br)C=C32)=C(C4=COC5=C4C=CC=C5)C(N1)=O |
| 31 | Huperzine A | no entry | CC1=C[C@H]2CCN(C3)=C([C@@](C1)(C2=C(O)NC=CC3=O |
| 32 | Volinensertin | no entry | COC1=CC=C(C=C1)N(C2CN(CC2)CCC3=CC=C(C=C3)F)O)=C1OC |
| 33 | 8-Bromo-cAMP | no entry | BrC1=NC2=CN(N=CN=C2N1C3O4COP(OC4C3O)(O)=O[Na] |
| 34 | Bromoindirubin-3-oxime | no entry | BrC(C=C1)=CC2=C1NC(C2=C3C)NO)=C4C=CC=C3CNO)N/3 |
| 35 | Cytisine | no entry | O=C1C=CC=C2N1C[C@@H]3CNC[C@H]2C3 |
| 36 | Difluorobenzocurcumine | no entry | O=C(/C=C(/C=C/C=C/C(/O)=C/C(OC)=C1)=O)=CC2=C(F)C(F)=C2)C=C3=CC(OC)=C(OC)C=C3 |
| 37 | Tacedinaline | no entry | O=C(NC1=CC=CC=C1NC2=CC=C(NC(C)=O)C2 |
| 38 | TDZD-8 | no entry | O=C(N1CC2=CC=C(C)N(C)SC1=O |
| 39 | Oxanflatin | no entry | O=C(/NO)/C=C/C#CC1=CC=C(N(S(=O)(C2=CC=CC=C2)=O)=C1 |
| 40 | EMD-386,088 | no entry | CIC1=NC2=C(NC(=C)C2=C3=CCNCC3)C=C1•Cl |
| 41 | SB-216763 | no entry | O=C([C@]1(CCCC2(C@@])[C@H](C(C@@H](C(H](C@@]3(H)C)C2C3=CN(C1)C=C(C=C4)NC2=O |
| 42 | Colforsin dapropate | no entry | C=C([C@@]1(CCC(C)([C@H](C(C@@])3(H)C(C@@]1(C(@H](C@@)(C@@]23C)OOC(CCN(C)C)C)=O)(CC(OC)=OCC)=O)C•Cl |
| 43 | RG-108 | no entry | O=C1C(C(=C(N2C(C(/C=C/C3=CN(C1)C3)NC4=CC=CC=C43)=O |
| 44 | Antalarmin | no entry | CC1=C(N2C(C=C(C)N3=C2N=CC(CCC)=N3=C(CC)CC)=C1•Cl |
| 45 | TCS 1205 | no entry | O=CCN[C@H](C1=CC=C(C=C1)C(C)C=C(N3C3CC.Cl |
| 46 | CP-154,526 | no entry | CCCCN(C1=NC(C)=NC2=C1C(C)=CN2C3=C([N+](O=)=O)C=C3)=O |
| 47 | GYKI-53655 | no entry | O=C1N(CNC)CC(C2=C1C=C3C=C(OCO4)C=C4C=C(C=C3OCC.Cl |
| 48 | Nefiracetam | no entry | O=C1N(CCC(=O))CC(NC=C2=CC(C)=C(C)C2)=O |

| No. | Drug Name | ATC code | Chemical Structure |
|---|---|---|---|
| 49 | Hexaralin | no entry | NCCCC[C@@H](CN)=O)NC[C@@H](CC1=CC=CC=C1)NC[C@H](CC2=CNC3=CC=CC=C23)NC-([C@H](C)NC([C@@H](CC4=C(NC5=CC=CC=C45)NC([C@@H](CC6=CNC=N6)N=O)=O)=O)=O |
| 50 | Nociceptin | no entry | O=C(NCCNCCNCCN[C@@H](CC1=CC=CC=C1)CN[C@@H](CC6=CNC[C@@H](C)NC[C@@H](CCCCN)=N)CN[C@@H](CCCCN)C(=O)N[C@@H](CCCN(C)N)=NC(N[C@@H](CCCCN)=NC(N[C@@H](CC(C)C)N[C@@H](CCCCN)C(N[C@@H](CCCCN)=O)C-(N[C@@H](CO)C)N[C@@H](CO)C)N=C(N)N=C(N)N=C1)C(=O)C(=O)=O)=O)=O)=O)[C@@H](CC2=CC=CC=C2)N |
| 51 | Fursultiamine | no entry | O=CN(CC1=C(N)N=C(N)=C1)C(=C(CCO)SSCC2OCCC2 |
| 52 | Spiperone | no entry | FC1=CC=C(CCCCN2CCC3(NCN3C4=CC=CC=C4)=O)CC2)=O)C=C1 |
| 53 | Harmaline | no entry | CN1=NCCC2=C1NC3=C2C=CC(OC)=C3 |
| 54 | Kavain | no entry | O=C1C=C(OO)C[C@H](/C=C/C2=CC=CC=C2)O1 |
| 55 | P7C3 | no entry | OC(CN1C2=C(C3=C1C=CC(Br)=C3)C=C(Br)C=C2)CNC4=CC=CC=C4 |
| 56 | Letrepirdine | no entry | CC1=CC=C(CCN2C3=C(CN(C)CC3)C4=C2C=CC(C)=C4)C=N1=C5=CC=C(CCN6C7=C(CN(C)CC7)C8=C8C=CC(C)=C8)C=N5•Cl•Cl |
| 57 | Benzydamine | no entry | CN(C)CCCOC1=NN(CC2=CC=CC=C2)C3=C1C=CC=C3 |
| 58 | Berberine | no entry | COC(=CC1=C2C=[N+](CC3)C4=C3C=C5C(OCO5)=C4)=C1)=C20C•[Cl] |
| 59 | Ciorgyline | no entry | ClC1=CC(=C(C1)=C20CC#CN(C)CC#C•Cl |
| 60 | Ethaverine | no entry | CCOC1=CC2=C(C=C10COC=CN=C2OCC3=CC=C(OCC)C(OCC)C3=C1 |
| 61 | Girigolide | no entry | O=[C@@H]1C(OC@@H]2C[C@@]34C[C@H]5C[C@@H]1C[C@@]36[C@H](C[C@H]2O[C@@H]0[C@@H]]24[C@@]12O[C@]O5)=O)=O)(C)(O)C=O |
| 62 | Idazoxan | no entry | C1(C2OC3=CC=CC=C3O2)=NCCN1•Cl |
| 63 | Pirlindole | no entry | CC1=CC2=C(N3CCNC4C3=C2CCC4)C=C1•CS(O)(=O)=O |
| 64 | Rolipram | no entry | O=C1NCC(C2=CC(OCC3CCCC3)=C(OC)C=C2)OC)C1 |
| 65 | Dizocilpine | no entry | C[C@@]12C3=CC=CC=C3C[C@H](N2)OC4=CC=CC=C14•O=C([C=C/C([O-])=O |
| 66 | SKF 89976A | no entry | OC(C1CN(CCC=C(C2=CC=CC=C2)C3=CC=C3)CCC1)O•Cl |
| 67 | NNC 05-2090 | no entry | OC1(C2=CC=CC=C20)CCN(CCCN3C4=CC=C(C5=CC=C3C=CC=C5)C=C4)CC1•Cl |
| 68 | NNC 711 | no entry | O=C(C1=CCCN(CCON=C(C2=CC=CC=C2)C3=CC=CC=C3)C1)O•Cl |
| 69 | Cotinine | no entry | O=C1N[C@@H](CC1)C2=CC=CN=C2)C |
| 70 | Famprofazone | no entry | C1C(C(=O)C)=C(N(C(C)C)=C(C2=CC)N(N)C13=CC=CC=C3 |
| 71 | CGP 55845 | no entry | O=P(CC1=CC=C(C1)NC[C@@H](O)CN[C@@H](C2=CC=C(C1)C=C1)C=C1)C(C)C)=C1)C2)O•Cl |
| 72 | Baicalin | no entry | O=C1C=C(C2=CC=CC=C2)OC3=C1(OC)=C(O[C@H]2C[C@@H](O)[C@H](O)[C@H](C(O)=O)O2)C(O)=C3 |
| 73 | Anisodarmine | no entry | OCC(C1=CC=CC=C1)C(O[C@H]2C[C@@H]3C[C@@H](N3C)[C@@H](O)C2)=O |
| 74 | DU-14 | no entry | OCC(C1=CC=CCCCCCCC)=O/C=C1)N=O |
| 75 | Piperlonguminine | no entry | O=C(NCC(C)C)/C=C/C=C/C1=CC=C(OCO2)C1 |
| 76 | Roscovitine | no entry | CC(N1C=NC2=C(NCC3=CC=CC=C3)N=C(N(CC)CCO)N=C12)C |
| 77 | Palmaline | no entry | COC1=C(OCC2=C[N+]3CCC=C4C=C(OCO(OC)=C3)=C4C=CC=C1•C(Cl=] |
| 78 | Ipsapirone | no entry | O=C(C1=C2C=C(C[C@H](/C(=CC3=C(OCO3)C=C3)C=C1)NN(CCCCN3CCN(CCCCN3C4=NC=CC=C4)CC3)S2(=O)=O |
| 79 | Perospirone | no entry | O=C1N(CCCCN2CCN(C3=NSC4=C3C=CC=C4)CC2)C([C@@]5[H])C([C@@]15[H])=O |
| 80 | Tandospirone | no entry | O=C1N(CCCCN2CCN(CC2)C3=NC=CC=N3)C([C@H]4C([C@@H]5CC[C@@H]4C5)=O |
| 81 | RG-108 | no entry | O=C(O)[C@@H](N1C(C=CC=C2)=C2C1=O)CC3=CNC4=CC=CC=C43 |
| 82 | Entinostat | no entry | NC1=CC=CC=C1NC(C2=CC=C(CNC(OCC3=CN=CC=C3)=O)C=C2)=O |
| 83 | Icarin | no entry | O=C1C(O[C@H]2[C@@H](O)[C@@H]([C@H](O)[C@@H]2O)C)=C(C3=CC=C(OC)=C3)OC4=C1C(O)=CC(O[C@@H]5O[C@@H](C)[C@H](O)[C@@H](O)[C@@H]5O)=C4C[C@@H](C=C(C)C)[C@@H]5O- |
| 84 | Yangonin | no entry | COC(=C1)=CC=C/C2=CC(=C(C=C(C=C(O(C=C)C)=C3)O)=O |
| 85 | Epigallocetechin | no entry | O[C@@H]1CC2=C(O[C@@H](C3=CC(O)=C(O)=C(O)C3)C1)C=C(O)C=C2O |
| 86 | Kavahin | no entry | COC1=CC(O[C@H](/C=C/C2=CC=CC=C2)C3=CCC(=O)C1)=O |
| 87 | Rotundine | no entry | COC1=C(C2=C(C[C@@H]3C4=CC(OC)=C(OC)=C4CCN3C2)C=C1)OC |
| 88 | Keerpferol | no entry | O=C(C1=CO)C(O)=C(O)C=C1O)C2=CC=C(O)C=C2 |
| 89 | Pregnenolone | no entry | CC([C@H]1CC[C@H]2[C@@H]3CC=C4C[C@@H](O)CC[C@@]4(C)[C@H]3CC[C@@]12C)=O |
| 90 | Resveratrol | no entry | O=C(OC)C1=CC=C(/C=C/C2=CC(O)=CC(O)=C2 |
| 91 | FG-4592 | no entry | O=C(O)CNCC1=NC(C2=CC=CC=C3C3)C=C1 |
| 92 | PNU-120596 | no entry | COC1=CC=C(C=C1NC2=C3CNCC4=NOC(C)=C3)=O)C1 |
| 93 | TWS119 | no entry | OC1=CC=C(OC2=C3C(NC4=CC(O)=CC=C4)=NC=NC3=NC=C2)C=C1 |
| 94 | Salidroside | no entry | OC[C@@H](O1)[C@@H](O)[C@H](O)[C@@H](O)[C@@H]1OCCC2=CC=C(O)C=C2) |
| 95 | Cyticine | no entry | O=C1N=C(C=CN1[C@@H2O][C@H](CO)[C@H](O)[C@H](O)1 |

-continued

| No. | Drug Name | ATC code | Chemical Structure |
|---|---|---|---|
| 96 | Piperine | no entry | O=C(/C=C/C=C/C1=CC2=C(OCO2)C=C1)N3CCCCC3 |
| 97 | Picamilone | no entry | O=C(NCCCC([O-])=O)C1=CC=CN=C1•[Na+] |
| 98 | EX-527 | no entry | O=C([C@@H]CNC2=C3C=C(Cl)C=C2)=C3CCC1N |
| 99 | Genistein | no entry | OC1=C(C2=COC3=C(C2=O)C(O)=CC(O)=C3)C=C1 |
| 100 | Daidzein | no entry | OC[C@H]1O[C=H]([C@@H]([C@H]([C@@H]1O)O)OC2=CC=C3C(C4=CC=C(C=C4)O)=COC3=C2)=O |
| 101 | UNC 0224 | no entry | CN1CCCN2=C3C=C(OC)C(OCCCN(C)C)=CC3=NC(N4CCN(C)CCC4)=N2CC1 |
| 102 | IOX1 | no entry | OC(C1=C2C=CC=NC2=C(C=C1)O)=O |
| 103 | Hydroxytacrine | no entry | NC1=C2C(O)CCCC2=NC3=CC=CC=C13•O=C(/O)C=C/C(O)=O |
| 104 | (R)-Raclofen | no entry | NC([C@@H](C1=CC=CC=C(C=C1)Cl)CC(O)=O |
| 105 | Sultoraphane | no entry | CS(CCCCN=C=S)=O |
| 106 | Picamilone | no entry | O=C(C1=CN=CC=C1)NCCCCC(O)=O |
| 107 | Ampalos | no entry | O=C(N1CCCCC1)C2=CC=C3N=CC=NC3=C2 |
| 108 | Sophorein | no entry | OC1=CC2=C(C(O)=C(C3=CC=C(C(O)=C3)O)O2=O)C3OJO2)=O)C(O)=C1 |
| 109 | Sumanirole | no entry | CC(N1CC(NC2=C3C=C(OC)(OCCCN4CCCC4)=CC3=NC(C5CCCCC5)=N2)CC1)C |
| 110 | UNC 0638 | no entry | CC(N1CC(NC2=C3C=C(OC)(OCCCN4CCCC4)=CC3=NC(C5CCCCC5)=N2)CC1)C |
| 111 | UNC 0546 | no entry | COC1=CC2=C(NC3CCN(C4CCCCC4)CC3)N=C(N5CCN(C(C)C)CC5)N=C2C=C1OCCCN6CCCCC6 |
| 112 | YC-5-169 | no entry | O=C(CCCCCCCC(C1=C(NC=CC=C1)=O)NC2=CC=C(C3=CN(C4=CC=C(C4)N=N3)=CC=C2 |
| 113 | Safinamide | no entry | O=C([C@H](C)NCC1=CC=C(OCC2=CC(F)=CC=C2)C=C1)N |
| 114 | CHIR-98014 | no entry | NC1=NC(NCCNC2=NC=C(N3C=CN=C3)(C4=CC=C(Cl)C=C4O)=N2)=CC=C1[N+]([O-])=O |
| 115 | IOX2 | no entry | C=C(NCOOOC1=C(OC2=CC=CC2N(CC3)CC)=NC4=C2CCCCC4)C=C1 |
| 116 | Bioranserin | no entry | FC1=CC=C(C2=CC(N3CCN(CC3)CC)=NC4=C2CCCCC4)C=C1 |
| 117 | Ganaxolone | no entry | C([C@H]1CC[C@@H]2[C@]1(C)CCC[C@@H]3[C@@H]2CC[C@@H]4[C@]3C=C[C@@H](IC)(C)C4=O |
| 118 | Harmane | no entry | CC1=NC=CC2=C1NC3=CC=CC=C32 |
| 119 | Sazetidine | no entry | OCCCCC#CC1=CC(OCC2CCN2)=CN=C1•OCCCCC#CC3=CC(OCC4CCN4)=CN=C3•Cl•Cl |
| 120 | AK-7 | no entry | CC(=C(NC1=CC=CC(Br)=C1C2=CC=CC(S(=O)(N3CCCCC3)=O)=C2 |
| 121 | PF 4778574 | no entry | CC(S(=O)N[C@@H]1[C@@H](C=C)=CC=C(C3=CC=C(#N)S3)C=C2)COCC1)=O)C |

Figure 29:
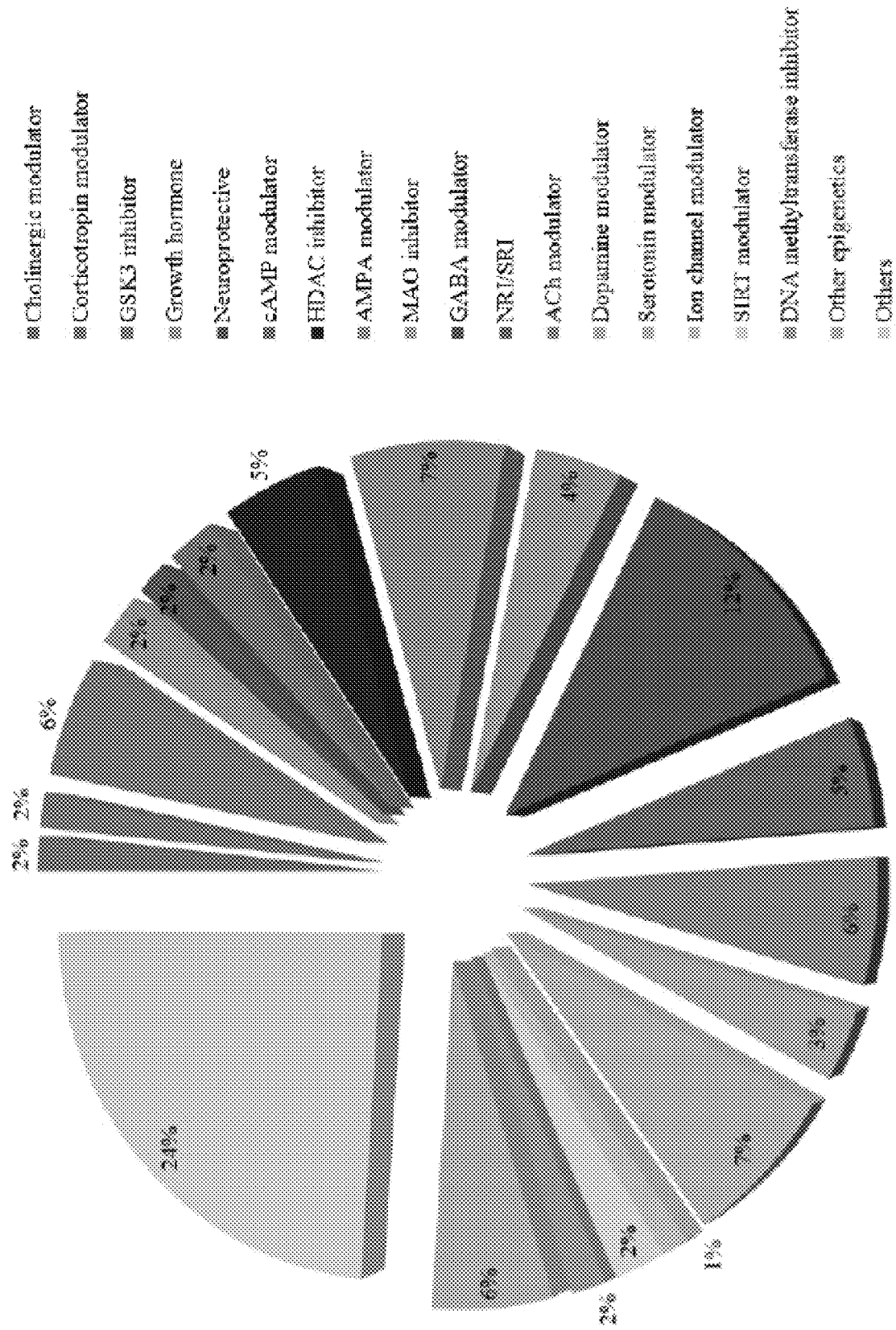
FIG. 29 is a chart showing a diversity of the non-clinical set in terms of pre-annotated mechanisms.

Such test set was constructed in a random manner to ensure sufficiently large coverage of different molecular target, as illustrated in FIG. 29. The goal during this portion was to employ BAM-based phenotyping to predict the potential therapeutic role of these "test set" non-clinical compounds using a two-step prediction methodology.

Figure 21:
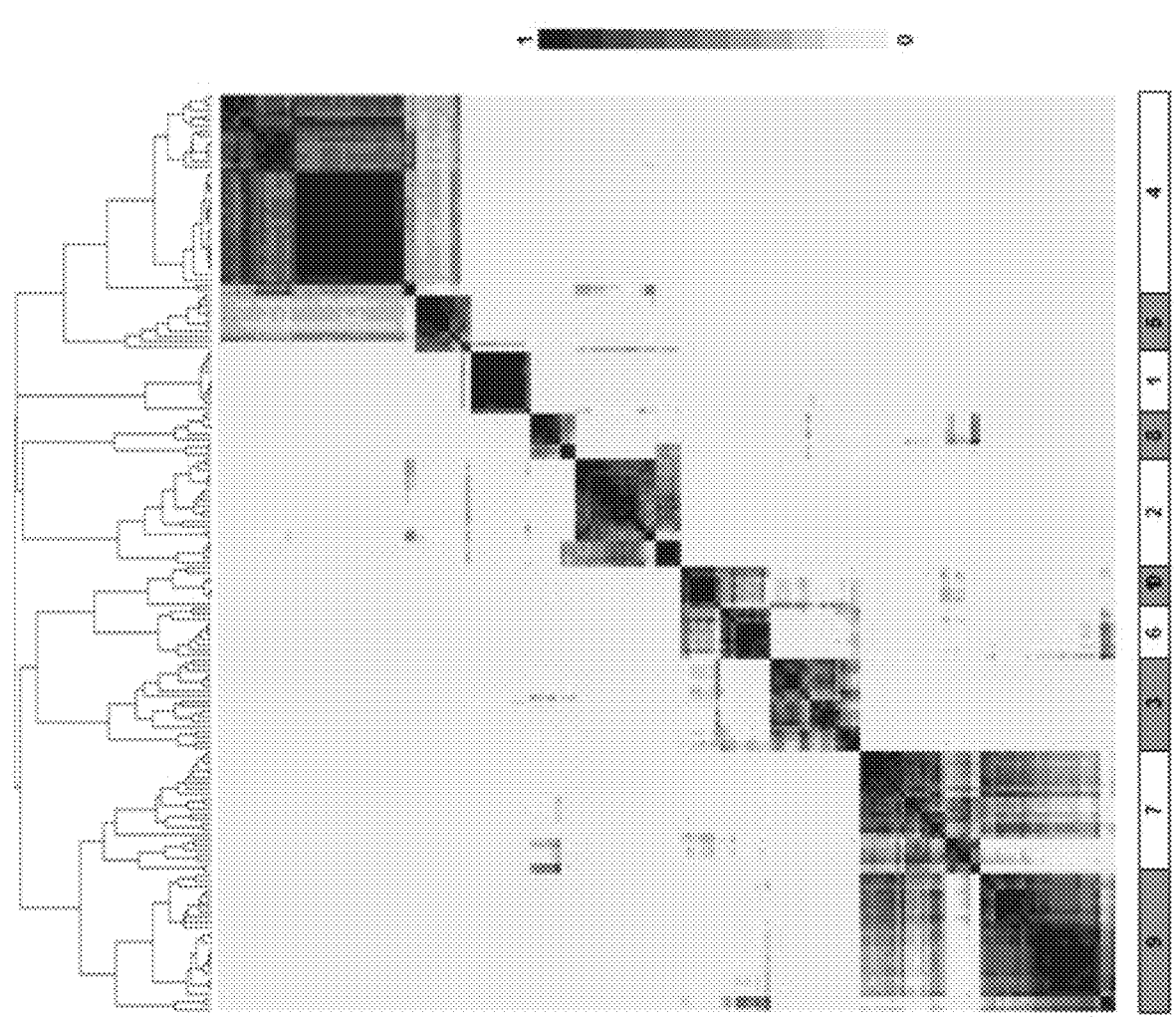
FIG. 21 is an illustration showing consensus clustering identified 10 phenotypic BAM clusters, the heat map was the consensus matrix illustrating the frequency of the scenario that two compounds in a pair were clustered together, the color of the heat map is proportional to the frequency scores of the consensus matrix, ranging from 0 to 1.
Figure 22:
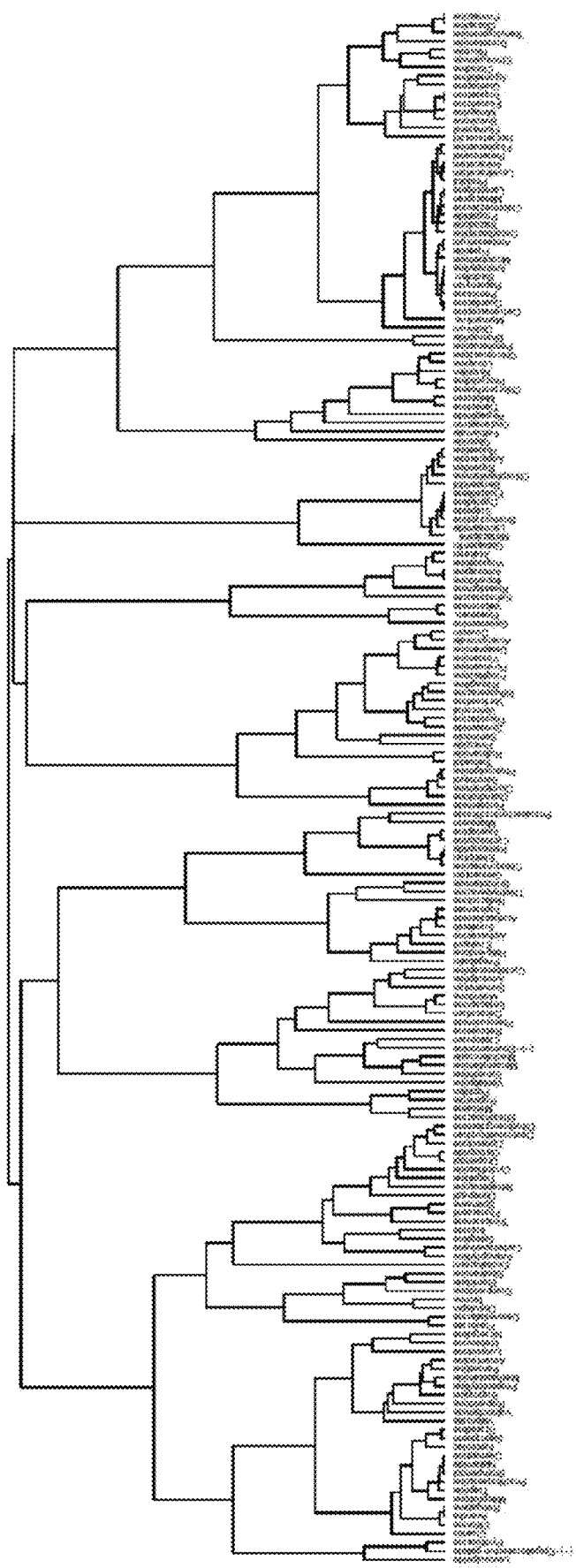
FIG. 22 is a dendrogram illustrating consensus clustering results with drug names.
Figure 30A:
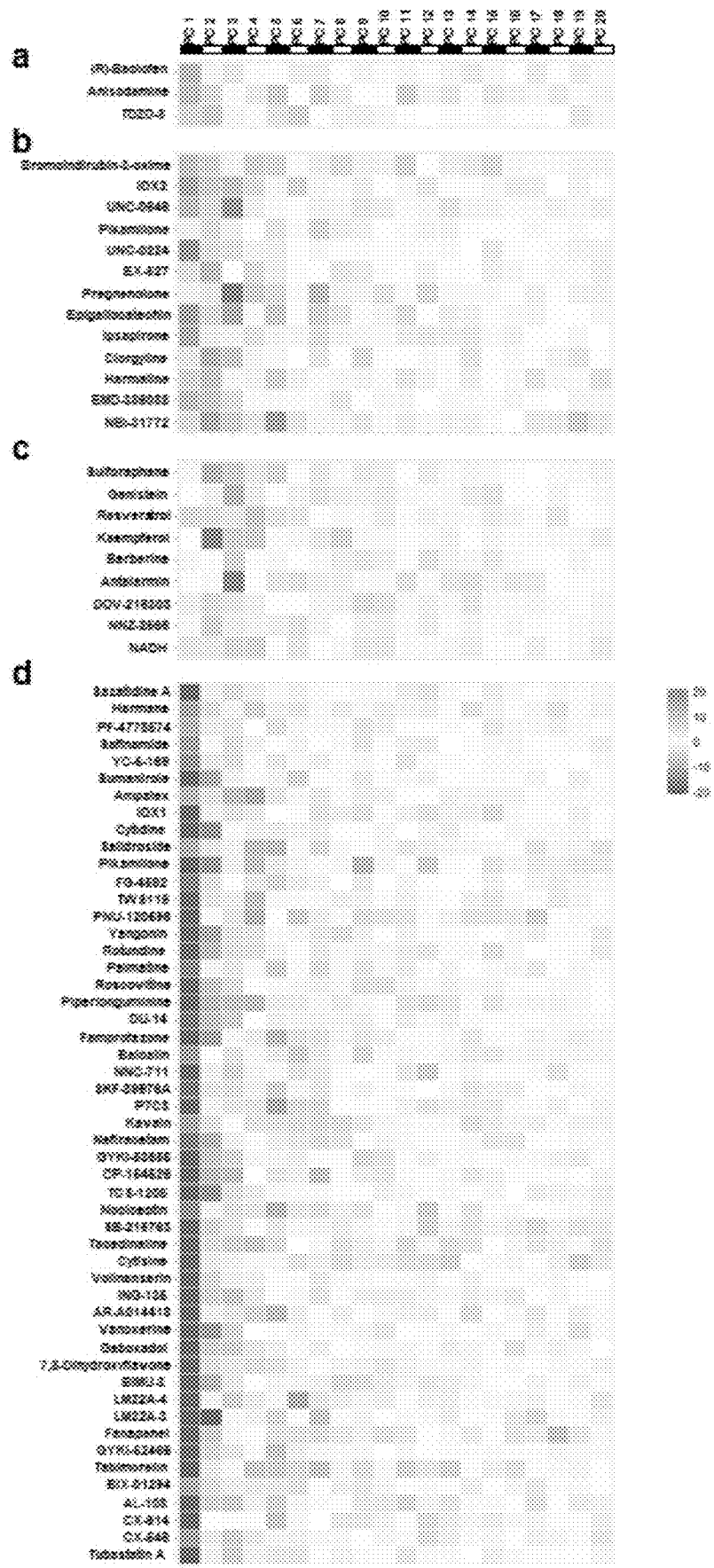
FIGS. 30A and 30B are charts showing 10 predicted clusters of the non-clinical used compounds with the 20-dimensional pheno-prints.
Figure 30B:
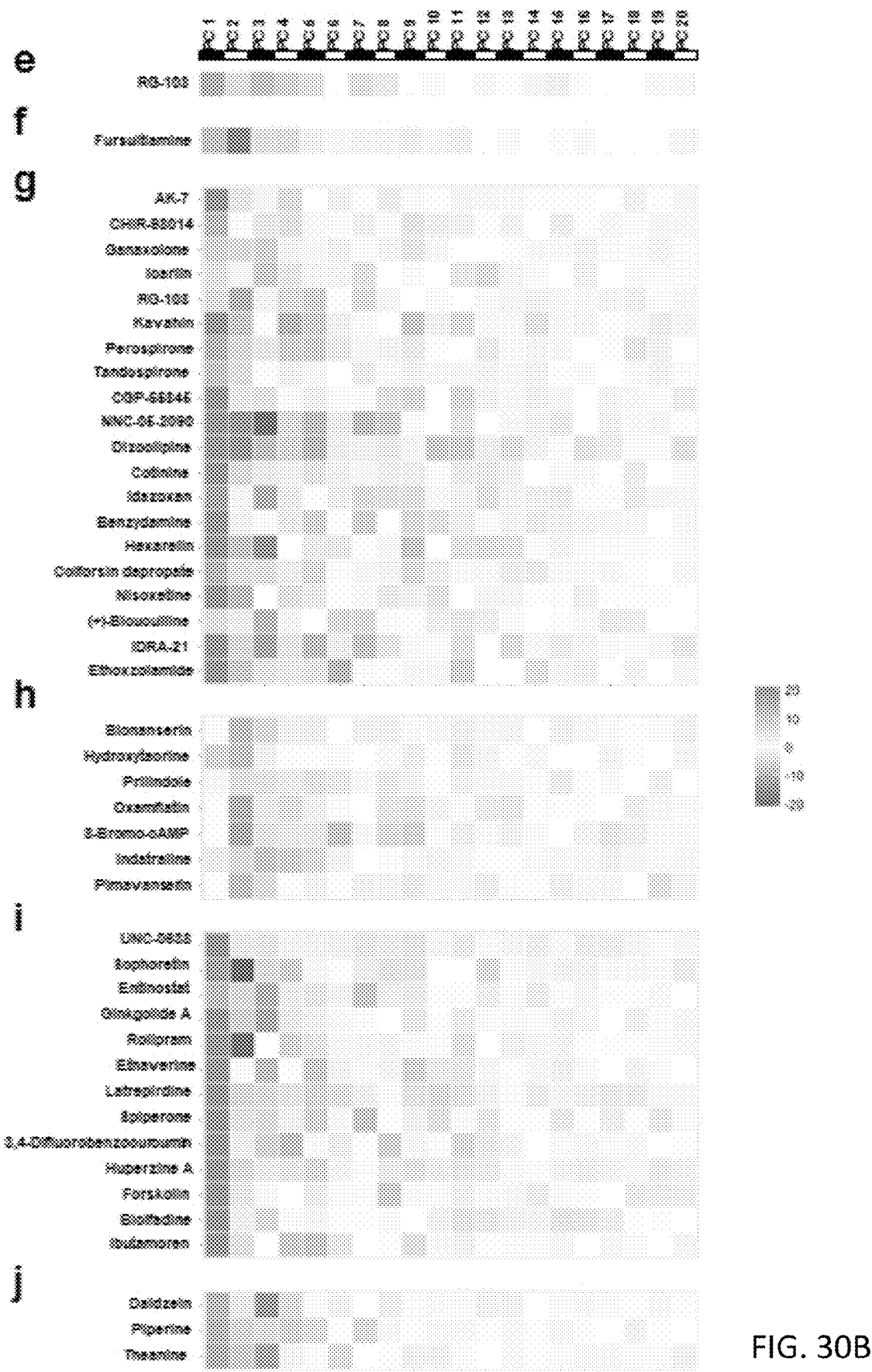

First, the clustering result from the "training set" (179 ATC-coded drugs) was used to generate a random forest classifier as shown in FIG. 21, which is a machine learning paradigm that employs an ensemble of decision trees for robust classifications. Referring to FIGS. 30A and 30B, the processing module 112 computationally assigned the 121 compounds into one of the ten BAM clusters previously generated from the "training set".

Second, compounds from the "test set" that were assigned to those clusters with significant association with ATC categories (clusters 3, 4, and 8) were further prioritized based on the Pearson correlation coefficient (therapeutic potential) between the compound's Pheno-Print and the centroid (in 20 dimensional PC space) of all drugs in the signature subgroup of a particular BAM-cluster, as illustrated in FIG. 31. This correlation was then used as a quantitative index to rank the therapeutic potential of the classified compounds.

Figure 32:
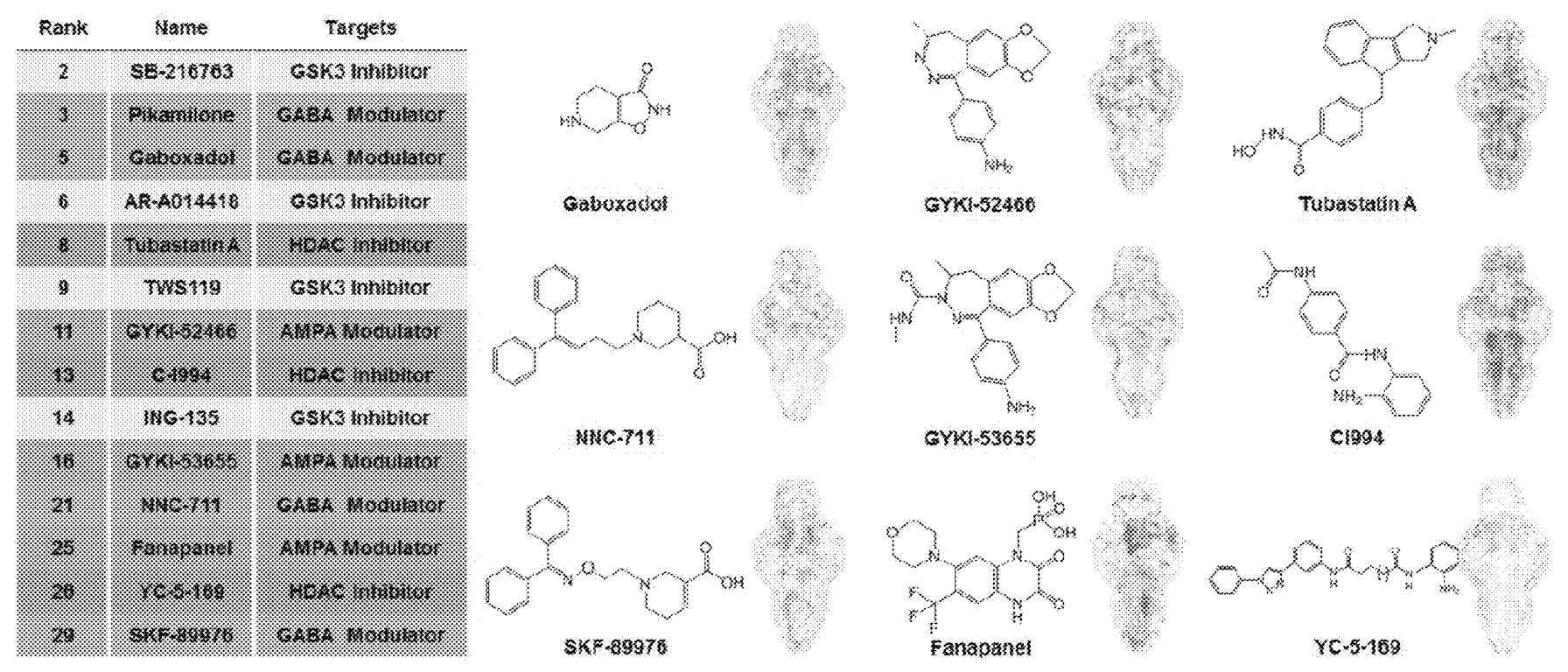

With reference to FIG. 32, in parsing the therapeutic potential of compounds, it may be observed that predicted cluster was enriched for potential anti-epilepetics among the top-ranked compounds: of the top 30 compounds, more than 47% anti-epilepetics properties are well supported in some other examples as shown in FIG. 33.

In particular, gaboxadol, SKF89976A, and NNC-711 have previously been reported to have anti-epileptic activity in animal models 23-25. SKF89976A and NNC-711 share highly similar chemical structures and are both inhibitors of GABA uptake. Another group of potent N03:Anti-epileptics candidates were AMPA receptor antagonists, including GYKI-52466, GYKI-53655 and fanapanel, whose anti-epilepetics properties are supported in some examples.

Of note, AMPA receptors antagonists are a new addition to the anti-epileptic armamentarium, as evidenced by the recent approval of the first anti-seizure drug in this class, perampanel, a selective, non-competitive antagonist used as adjunctive therapy in partial-onset seizures and the treatment of primary generalized tonic-clonic seizures.

In addition to compound classes with previously reported anti-epileptic activity, it is observed that the compound CI-994 was also predicted as a top-ranked N03:Anti-epileptics candidate. CI-994 is a known modulator of epigenetic mechanisms through its activity as a sub-class I selective histone deacetylase (HDAC) inhibitor, Structurally, CI-994 is an acetylated derivative of the substituted benzamide dinaline, which may be a CNS-penetrant, anticonvulsant agent based upon in vivo testing in rodents.

Consistent with a role for HDAC inhibition as being a factor in driving the BAM profiles that cluster CI-994 within the predicted N03:Anti-epileptics group, an additional top-ranked prediction, YC-5-169, shares key structural feature with CI-994, namely an ortho-aminoanilide group that chelates zinc atoms in the active site of HDACs.

Furthermore, a second compound, Tubastatin-A, was also amongst the top ranked predicted compounds in the N03: Anti-epileptics group; due to its hydroxamic acid rather than ortho-aminoanilide group, Tubastatin A has a broader activity profile that includes HDAC6 and HDAC10 inhibition in addition to class I HDACs at higher doses. These results suggest that inhibition of HDACs may present a novel mechanism of action for development of future anticonvulsants.

Figure 34:
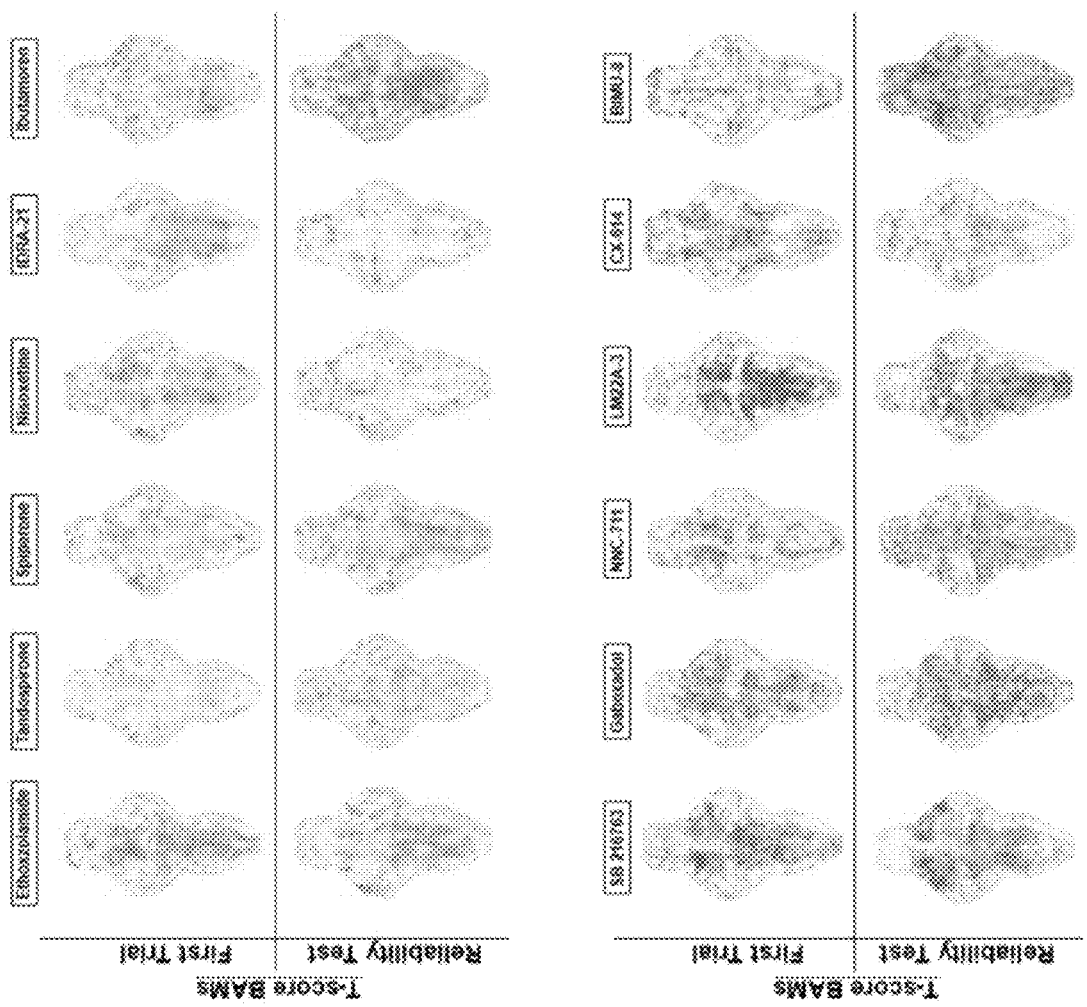
FIG. 34 is an illustration showing the results of a reliability test using a small group of compounds in the test set, including a comparison of the classification based on the T-score BAMS between the first trial and the reliability test, examples of T-score BAMS acquired from the first trial and the reliability test in some compounds that showed BAMS indicative of enhanced neural activity and silenced neural activity.

To test the reliability of this HT-BAMing-based compound screening strategy, we repeated the analysis on a small subgroup of 20 compounds randomly selected from the test set. With reference to FIG. 34, most of the T-score BAMs were similar to that acquired in the first trial. After inputting the re-acquired BAMs into the classifier, it is observed that 90% (18 of 20) of the compounds were assigned to the same cluster as in the first trial, indicating the screening strategy and analysis is highly reproducible.

Figure 35:
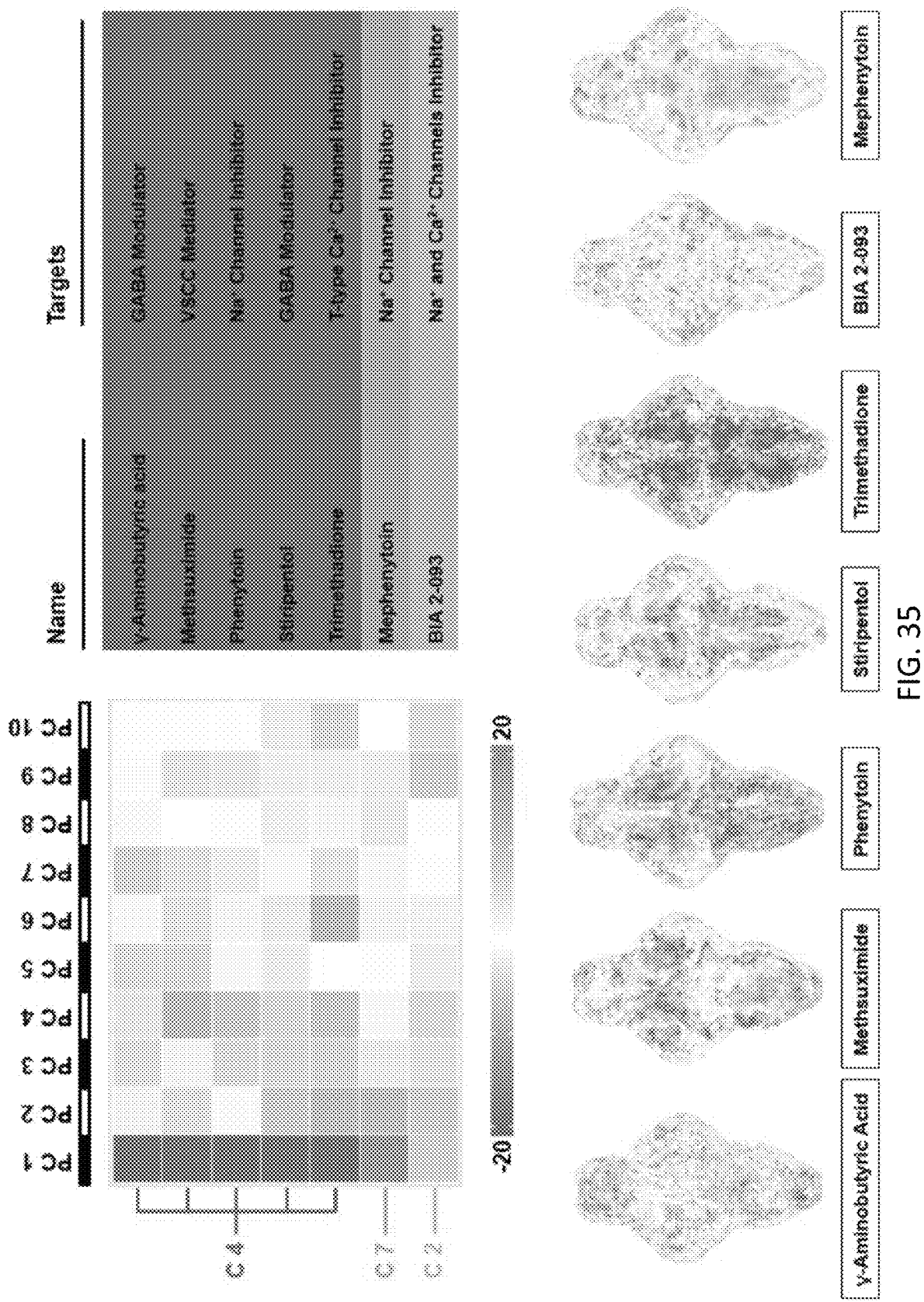
FIG. 35 shows prediction validation results using extra clinical antiepileptic drugs that were not included in the training set, the classification of the drugs using the associated pheno-prints is derived from according T-score BAMS, the dark-blue shaded table shows the drugs with correct prediction, the abbreviations are: C4, Cluster 4; C7, Cluster 7; C2, Cluster 2; PC, principle components, the T-score BAMS of the seven tested antiepileptic drugs are also shown.

In another validation experiment, with reference to FIG. 35, seven additional clinical anti-epileptics that were not present in either the training or test sets were tested. Using only their BAMs as inputs, five of the seven drugs (~70%) were classified to cluster 4 (N03:Anti-epileptics cluster), and were ranked among the top hits within the cluster when added to the results from the test set.

With reference to FIG. 36, this included the inhibitory neurotransmitter GABA, the GABA(A) receptor positive allosteric modulator and possible lactate dehydrogenase inhibitor stiripentol, the voltage-sensitive calcium channel antagonists methsuximide and trimethadione, and the sodium channel antagonist phenytoin. These results demonstrate the generalizability of the present method to compounds not tested in the original screen and that it may be anticipated that as the classification will be improved as compounds are continuously added to the training set library.

Figure 37:
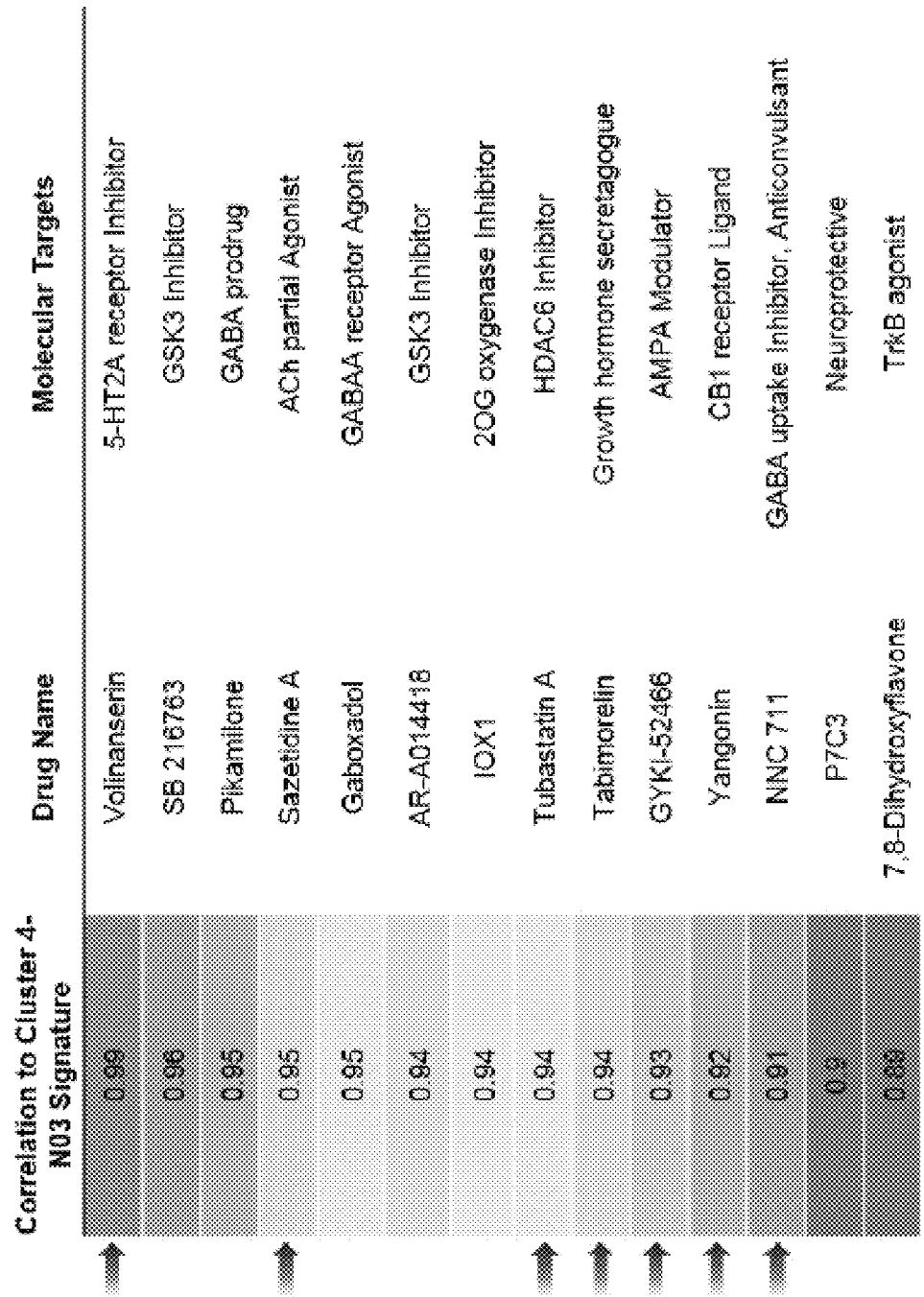
FIG. 37 is a table showing compounds tested in the behavioral assay in larval zebrafish using PTZ seizure model, blue arrows indicate the "hit" compounds with anti-seizure efficacy in the PTZ model.

To validate the results of our machine learning-based therapeutic classification of activities of bioactive compounds, referring to FIG. 37, 14 top-ranked anti-epileptic candidates for testing in the pentylenetetrazole (PTZ) induced zebrafish seizure model were selected. PTZ is a non-competitive antagonist of γ-aminobutyric acid type A (GABA(A)) receptor-mediated chloride currents that may be used to study seizure phenomenon across a wide range of vertebrates, including zebrafish.

Figure 38:
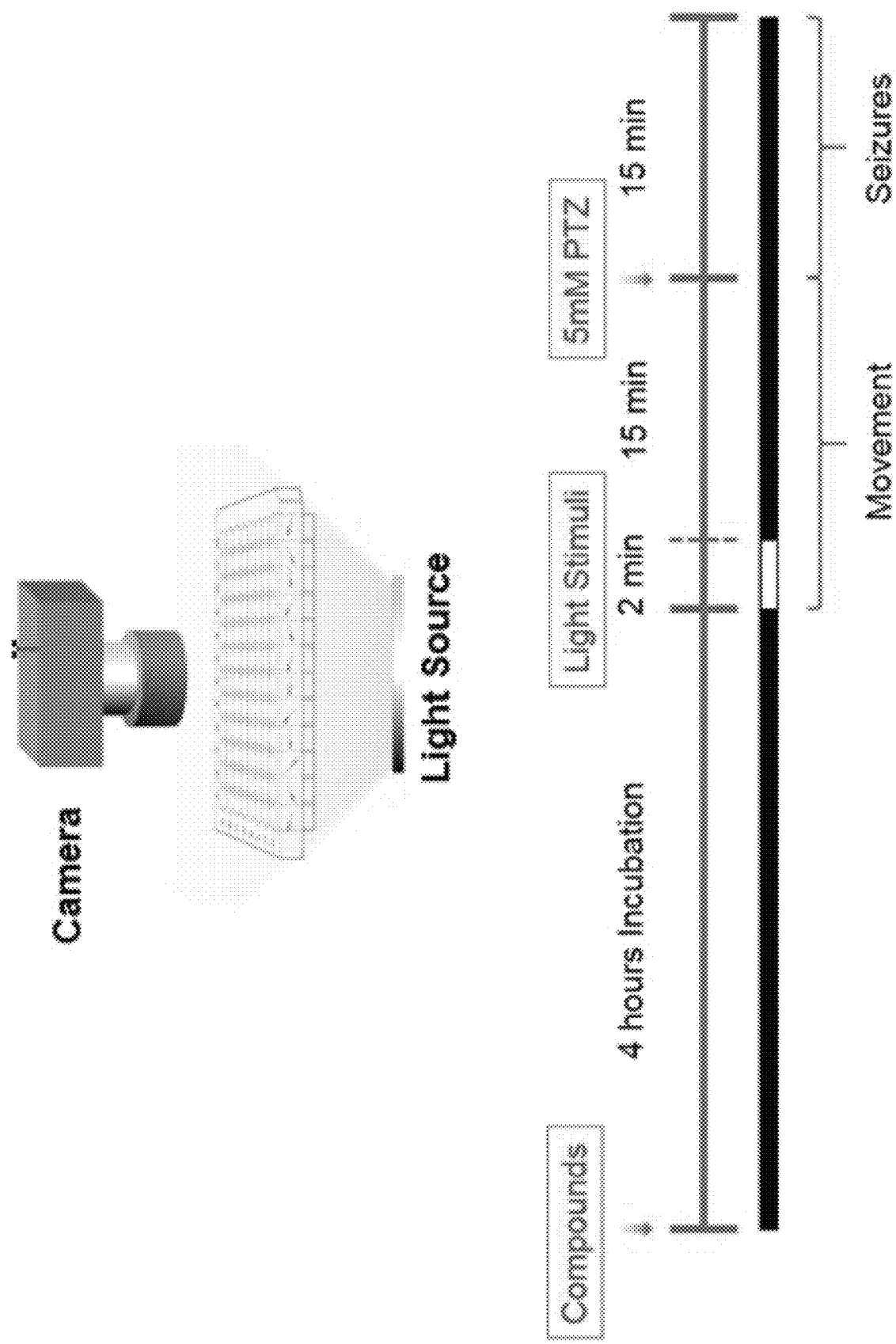
FIG. 38 is an illustration showing schematic of the setup for the behavioral test and the experimental protocol for validation of the hit compounds using behavioral test in PTZ-seizure animal model.
Figure 40E:
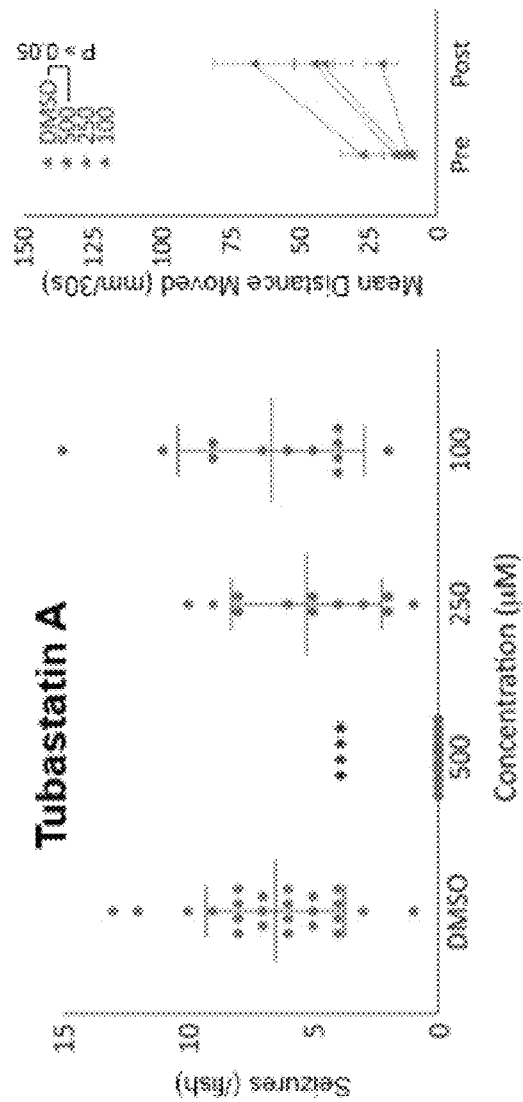
Figure 40F:
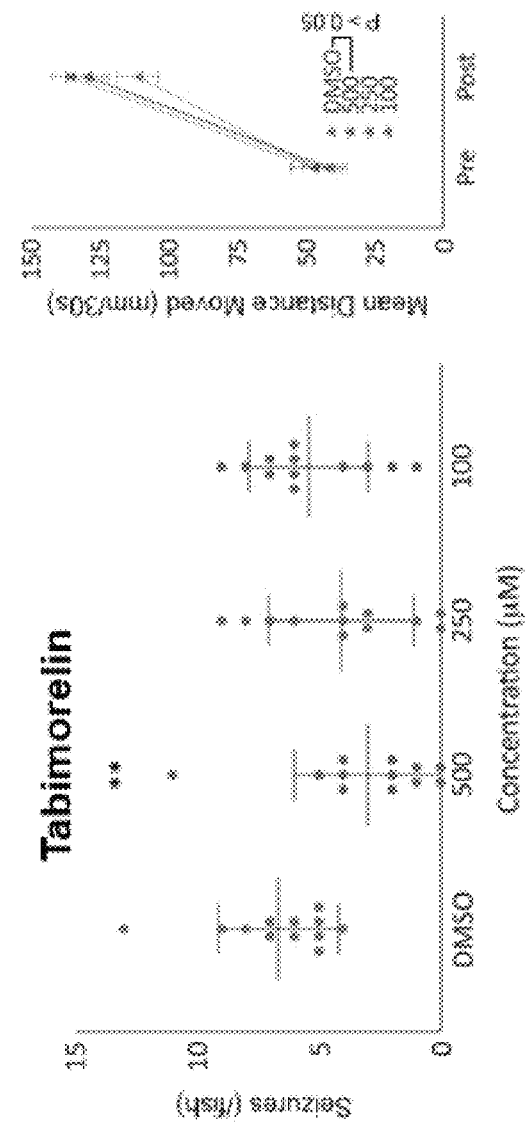

By blocking inhibitory neurotransmission mediated by GABA(A) receptors this leads to a proconvulsant effect. In these experiments, with reference to FIG. 38, following a four-hour drug incubation period, zebrafish larvae were pre-monitored for normal movements/swimming behavior for 17 minutes. At two minutes, the lights were turned off, which should normally induce a rapid increase in movement; failure to increase movement suggested fish were sedated or otherwise unable to respond normally to the stimulus. At the 17-minute mark, the larvae were treated with PTZ to a final concentration of 5 mM, and the number of seizures per larva and the average number of seizures at each concentration were quantified for 15 minutes following PTZ exposure.

After excluding 2 compounds were insoluble at higher concentrations, larva pre-treated with seven of the 14 compounds tested were found to have fewer seizures than the DMSO-treated control larvae without sedating the fish. For example, with reference to FIGS. 39A and 39B, pre-treatment with NNC-711, resulted in marked reduction in seizures following PTZ treatment, even with concentrations as low as 25 μM, without an apparent effect on zebrafish locomotor behavior.

The experimental protocol uses a 96-well plate, with one zebrafish larva (5 days post-fertilization) in 90 μL of fish water in each well. 10 μL of a 10× solution of compound in 10% DMSO was added to each well to achieve the final concentration shown in the data, and for a final concentration of 1% DMSO. For each concentration, there were 12 fish, and each plate had a group of control larva treated with 1% DMSO (final concentration). Final concentrations of compounds were 500 µM, 250 µM, and 100 µM, except in the case of compounds found to be highly insoluble in water, in which cases the final concentrations were 50 µM, 25 µM and 10 µM; insoluble compounds tested at these lower concentrations were 7,8-dihydroxyflavone, AR-A014418, P7C3, volinanserin, and yangonin. The larvae were pretreated with compound for four hours, followed by a two minute dark stimulation to ensure fish were not sedated, followed by a 15 minutes period of observation for deviation from the anticipated normal movement/swimming behavior. A quick change from light to dark induces an increase in activity in zebrafish. After a 15 minute observation period, the larvae were treated with PTZ to a final concentration of 5 mM, and the number of seizures per larva at each concentration quantified for 15 minutes following PTZ treatment. The DanioVision platform (Noldus) was used to perform the animal behavioral recoding and analysis.

With reference to FIGS. 39C to 39E, Such pharmacological effects could also be observed in the diametrically opposed BAMS from zebrafish treated in the same manner. NNC-711 is thought to principally act through the inhibition of GABA uptake from the synaptic cleft and glia via inhibition of SLC6A1 (solute carrier family 6 member 1; (GAT1)) leading to increased GABA-ergic neurotransmission. These observations in the PTZ zebrafish seizure model are therefore consistent with the anticonvulsant efficacy of NNC-711 in rat models of induced epilepsy.

Another candidate predicted from the BAMS analysis to have anti-epileptic activity was, GYKI-52466, a non-competitive AMPA receptor antagonist, which was tested and confirmed in the PTZ seizure model. In agreement, GYKI-52466 has been shown previously to have anticonvulsant activity in a kainic-acid induced seizure model in mice 39.

In addition to the examples of NNC-711 and GYKI-52466, for which retrospective support can be provided for their efficacy from the literature, there were also several non-obvious activities of the predicted hits when tested in the PTZ model. With reference to FIGS. 40A to 40F, for example, volinanserin, a highly selective 5-HT2A receptor antagonist that has been tested as a potential antipsychotic, antidepressant, and sleep aid in pre-clinical models, but has not been reported to have anti-seizure activity, reduced seizures in our PTZ seizure model at relatively low does.

Yangonin is a kavalactone that, in the oncology literature, induces autophagy and inhibits the mTOR pathway, and is a novel CB1 receptor ligand, but with no reported anti-seizure activity. Also, the HDAC6 inhibitor Tubastatin-A reduced seizure count at a final concentration of 500 µM, the upper end of the concentration range employed in these experiments.

Overall, the hit compounds employed in the behavior validation studies were selected based on their Pearson correlation coefficient rank within the N03:Anti-epileptic cluster (all had a correlation coefficient of 0.89-0.99) and with an eye towards including a diverse array of putative mechanisms of action, not based on chemical structure or previously published results on their clinical effects. That seven of the 14 compounds tested demonstrated anti-seizure activity in the PTZ model supports the HT-BAMing technology using zebrafish as a physiology-based screening tool for pharmacological discovery.

When compared with alternative methods of recombinant DNA technology and tissue culture techniques, the embodiments of the present invention is more advantageous. The methods for functional CNS drug screening in larval zebrafish by using HT-BAMing technology may be capable of rapidly assessing changes in brain physiology and activity in response to exposure to a compound at the level of cellular resolution across an entire zebrafish brain.

In contrast, pharmaceutical discovery for CNS diseases have increasingly relied on simplified targets consisting of recombinant proteins or heterologous cellular models. Screening methods using organism models are limited in their ability to perform large-scale chemical screens based on direct evaluation of organ-specific physiology in a complex animal model. Here, we describe a novel strategy.

Using HT-BAMing, a collection of BAMs is generated, each of which reflects the changes in brain physiology caused by exposure to a particular compound in a library of bioactive compounds and approved drugs. As part of this screening strategy, a novel computational and machine learning-based process may be implemented to analyze the large-scale BAM dataset, and successful prediction of drug leads for neurological diseases without any prior chemical or molecular knowledge of the compound library may be obtained.

Double-blind analysis of a "training set" containing 179 CNS-active drugs revealed that the phenotypic BAMs naturally form coherent clusters, which were further discovered to have strong association with the clinical usage of those medications, based on their functional WHO ATC classification. This strategy was then validated in a "test set" of 121 non-clinical compounds without an ATC code. By employing the coherent BAM clusters derived from 179 ATC-coded drug set as a classifier, predictions about the potential therapeutic application of these compounds may be obtained. This association between BAM clusters and ATC categories bridges the enormous gap between high-throughput physiology phenotyping and the potential therapeutic applications of unknown compounds.

Notably, the BAM-based clustering and prediction are solely based on the modulation of brain activity following exposure to a compound. Therefore, it is not surprising to see a dramatic diversity, both in chemical structures and molecular targets, for compounds within the identified BAM clusters. In particular, for BAM cluster 4, which is strongly associated with the N03:Anti-epileptics ATC category, the signature subgroup for this cluster contains drugs targeting six different major molecular targets. This result suggests that the BAM-based assay according to the embodiments of the present invention provides a drug screening platform with the potential to accommodate the pathophysiologically complex nature of many brain disorders, including epilepsy and other disorders with network imbalance such as those caused by neurodegeneration 45, or autism spectrum disorders such as Rett syndrome 46 and Pitt-Hopkins syndrome 47. Indeed, screening of the test set of 121 compounds correctly clustered potent N03:Anti-epileptic compounds, and, critically, identified several important new lead structures for development of novel anti-epileptics, including volinanserin and yangonin.

In validating the prediction results using the PTZ seizure model, seven of the 14 compounds tested (50%) decreased seizure frequency without affecting normal behavior. Given that PTZ is a non-competitive GABA antagonist, the fact that the other seven compounds tested were negative in the PTZ model may reflect limited sensitivity of the PTZ model to detect anti-seizure activity mediated through a pathway other than GABA rather than true lack of efficacy as potential anti-seizure agents.

This exemplifies the power of the HT-BAMing based screening strategy to function independent of any particular pharmacological model, and also highlights the necessity of secondary functional phenotyping methods that are not limited by the knowledge of the pathophysiology of a disorder at the molecular level or to only a limited number of pharmacological models that may have inherent biases in their sensitivity. This is particularly powerful in a disorder such as epilepsy, in which seizures represent the common phenotypic expression of a multifactorial propensity towards seizure activity. Identification of compounds with previously unrecognized anti-epileptic activity may improve understanding of changes at the genetic, epigenetic and cellular levels that create and propagate a chronic tendency towards seizure.

Although the experiments focused on the analysis of anti-seizure drugs in this proof-of-concept study, the results suggest that the HT-BAMing based screening method can be applied to advance novel pharmacological discovery in other complex brain diseases. Two other BAM clusters from the training set, clusters 3 and 8, had significant overlap with ATC categories N04:Anti-Parkinson drugs and N06:Psychoanaleptics, respectively. The top-ranked prediction from the N04:Anti-Parkinson drugs ATC category, berberine, has been shown in mice to increase dopamine levels, similar to the pro-dopaminergic drugs entacopone and ropinirole.

Also, the top hit in the N06:Psychoanaleptics category, hydroxytacrine, shares in common the mechanism of acetylcholinesterase inhibition that the Alzheimer's disease drugs galantamine and rivastigmine in the BAM cluster 8 have. It is expected that the use of ATC clinical drugs to construct a larger training set should facilitate the translation of the pharmacological profiles of non-ATC compounds from zebrafish to humans.

Advantageously, the use of HT-BAMing technology may provide insight into mechanisms of action of poorly understood pharmacological agents and novel compounds, particularly as the number of "reference" BAMS obtained from treatment with well-characterized compounds with known mechanisms of action increases. The HT-BAMing based screening strategy presented here can be refined in several ways. For example, the clustering analysis can be refined by taking advantage of more advanced machine learning methods such as recursive cortical network or deep learning algorithms; relevant structure-specific information in the BAMS may be spatially encoded for analysis.

To further improve the methods, obtaining BAMS at several time-points following one-time or repeated dosing may help identify compounds capable of affecting the course of CNS disorders through longer-term changes in CNS activity.

In addition, more advanced whole-brain imaging and analysis methods; including registration to brain atlases could help identify specific cell populations affected by compounds. Finally, the use of HT-BAMing in conjunction with zebrafish models of CNS disorders created through the introduction of causal genetic variants using CRISPR/Cas and related genome engineering strategies, has tremendous potential to advance an understanding of systems neuropharmacology and to assist in the discovery of novel disease-modifying pharmacological agents to expand the treatment options available to patients with CNS disorders.

It will also be appreciated that where the methods and systems of the present invention are either wholly implemented by computing system or partly implemented by computing systems then any appropriate computing system architecture may be utilised. This will include stand alone computers, network computers and dedicated hardware devices. Where the terms "computing system" and "computing device" are used, these terms are intended to cover any appropriate arrangement of computer hardware capable of implementing the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A method for analyzing neuropharmacology of a drug, comprising the steps of:
   providing a set of brain activity maps representing changes of a brain activity of a living species under an influence of a plurality of known drugs each consisting of a known chemical structure;
   determining standardized scores for each of a plurality of regions of interest on each of the brain activity maps associated with the plurality of known drugs and a chemical compound;
   obtaining a plurality of score maps associated with the standardized scores and each of the brain activity maps;
   clustering the set of brain activity maps to form a plurality of functional classifiers, the step of clustering comprising the step of applying principle component analysis to decompose the plurality of score maps into a plurality of characteristic features; and
   classifying a brain activity map associated with the chemical compound using the functional classifiers so as to predict a neuropharmacology of the chemical compound.

2. A method for analyzing neuropharmacology of a drug in accordance with claim 1, wherein the step of classifying the brain activity map associated with the chemical compound using the functional classifiers comprises the step of identifying a relationship between the set of brain activity maps and at least one therapeutic function of the known chemical structures of the plurality of known drugs.

3. A method for analyzing neuropharmacology of a drug in accordance with claim 2, wherein the step of classifying a brain activity map associated with the chemical compound using the functional classifiers comprises the step of ranking the chemical compound based on the identified relationship associated with the known chemical structures of the plurality of known drugs.

4. A method for analyzing neuropharmacology of a drug in accordance with claim 3, wherein the relationship is represented as a plurality of coefficients and/or factors being used for the ranking.

5. A method for analyzing neuropharmacology of a drug in accordance with claim 1, wherein the standardized scores includes T-scores.

6. A method for analyzing neuropharmacology of a drug in accordance with claim 1, wherein each of the plurality of score maps is obtained by filtering the determined standardized scores with a template of a brain of the living species.

7. A method for analyzing neuropharmacology of a drug in accordance with claim 1, wherein the step of clustering the set of brain activity maps to form a plurality of functional classifiers comprises c the step of generating the functional classifiers based on the plurality of characteristic features obtained by a supervised clustering method or an unsupervised clustering method.

8. A method for analyzing neuropharmacology of a drug in accordance with claim 1, wherein the living species includes a zebrafish.

9. A method for analyzing neuropharmacology of a drug in accordance with claim 8, wherein the living species includes a zebrafish larva.

10. A method for analyzing neuropharmacology of a drug in accordance with claim 1, wherein the plurality of known drugs include central nervous system drugs or agents.

11. A method for analyzing neuropharmacology of a drug in accordance with claim 1, wherein the chemical compound includes a neuroactive compound.

12. A method for analyzing neuropharmacology of a drug, comprising the steps of:
    generating a set of brain activity maps representing changes of a brain activity of a living species under an influence of a chemical compound and each of a plurality of known drugs, the plurality of known drugs each consisting of a known chemical structure, the step of generating comprising the step of obtaining images of a brain of the living species under the influence of each of the plurality of known drugs and the chemical compound;
    processing image raw data of a plurality of image frames obtained in an image capturing process performed on the living species so as to construct each of the images;
    clustering the set of brain activity maps to form a plurality of functional classifiers; and
    classifying a brain activity map associated with the chemical compound using the functional classifiers so as to predict a neuropharmacology of the chemical compound.

13. A method for analyzing neuropharmacology of a drug in accordance with claim 12, wherein the step of generating the set of brain activity maps further comprises the step of constructing the brain activity maps based on counting neural spikes representing changes of brain activity as detected on the images obtained.

14. A method for analyzing neuropharmacology of a drug in accordance with claim 12, further comprising the step of immobilizing the living species so as to obtain the plurality of image frames.

15. A method for analyzing neuropharmacology of a drug in accordance with claim 14, further comprising the step of orienting the living species being immobilized so as to obtain the plurality of image frames.

16. A method for analyzing neuropharmacology of a drug in accordance with claim 15, wherein the living species is immobilized and oriented by a microfluidic device.

17. A method for analyzing neuropharmacology of a drug in accordance with claim 16, wherein the living species is loaded to the microfluidic device using hydrodynamic forces.

18. A method for analyzing neuropharmacology of a drug in accordance with claim 12, wherein the living species includes a zebrafish.

19. A method for analyzing neuropharmacology of a drug in accordance with claim 18, wherein the living species includes a zebrafish larva.

20. A method for analyzing neuropharmacology of a drug in accordance with claim 12, wherein the plurality of known drugs include central nervous system drugs or agents.

21. A method for analyzing neuropharmacology of a drug in accordance with claim 12, wherein the chemical compound includes a neuroactive compound.

22. A system for analyzing neuropharmacology of a drug, comprising:
    an imaging module arranged to generate images of a brain of a living species;
    a transformation module arranged to generate, based on the images generated by the imaging module, a set of brain activity maps representing changes of a brain activity of a living species under an influence of a plurality of known drugs each consisting of a known chemical structure, and a brain activity map associated with a chemical compound; and
    a processing module arranged to cluster the set of brain activity maps to form a plurality of functional classifiers, and to classify the brain activity map associated with the chemical compound using the functional classifiers so as to predict a neuropharmacology of the chemical compound.

23. A system for analyzing neuropharmacology of a drug in accordance with claim 22, wherein the processing module is arranged to process the set of brain activity maps and/or the brain activity map using a statistical analysis and/or a machine learning process.

24. A system for analyzing neuropharmacology of a drug in accordance with claim 23, wherein the processing module is arranged to classify the brain activity map by identifying a relationship between the set of brain activity maps and at least one therapeutic function of the known chemical structures of the plurality of known drugs.

25. A system for analyzing neuropharmacology of a drug in accordance with claim 24, wherein the processing module is further arranged to rank the chemical compound based on the identified relationship associated with the known chemical structures of the plurality of known drugs.

26. A system for analyzing neuropharmacology of a drug in accordance with claim 23, wherein the transformation module is further arranged to determine T-scores for each of a plurality of regions of interest on each of the brain activity maps associated with the plurality of known drugs and the chemical compound.

27. A system for analyzing neuropharmacology of a drug in accordance with claim 26, wherein the transformation module is further arranged to generate a plurality of T-score maps associated with the T-scores and each of the brain activity maps.

28. A system for analyzing neuropharmacology of a drug in accordance with claim 27, wherein each of the plurality of T-score maps is obtained by filtering the determined T-scores with a template of a brain of the living species.

29. A system for analyzing neuropharmacology of a drug in accordance with claim 27, wherein the processing module is arranged to apply principle component analysis to decompose the plurality of T-score maps into a plurality of characteristic features.

30. A system for analyzing neuropharmacology of a drug in accordance with claim 29, the processing module is further arranged to generate the functional classifiers based on the plurality of characteristic features obtained by a supervised clustering processing or an unsupervised clustering processing.

31. A system for analyzing neuropharmacology of a drug in accordance with claim 22, wherein the transformation module is arranged to construct the brain activity maps based on counting neural spikes representing changes of brain activity as detected on the images obtained.

32. A system for analyzing neuropharmacology of a drug in accordance with claim 22, wherein the imaging module is arranged to process image raw data of a plurality of image frames obtained by an imager capturing the living species so as to generate each of the images.

33. A system for analyzing neuropharmacology of a drug in accordance with claim 32, further comprising a microfluidic device arranged to load the living species to a position to facilitate the imager to capture the living species so as to generate each of the images.

34. A system for analyzing neuropharmacology of a drug in accordance with claim 33, wherein the microfluidic device is further arranged to immobilize the living species.

35. A system for analyzing neuropharmacology of a drug in accordance with claim 34, wherein the microfluidic device is further arranged to orient the living species.

36. A system for analyzing neuropharmacology of a drug in accordance with claim 33, wherein the microfluidic device is arranged to load the living species using hydrodynamic forces.

37. A system for analyzing neuropharmacology of a drug in accordance with claim 33, wherein the microfluidic device includes one or more microfluidic channel adapted to accommodate one or more of the respective living species.

38. A system for analyzing neuropharmacology of a drug in accordance with claim 22, wherein the living species includes a zebrafish.

39. A system for analyzing neuropharmacology of a drug in accordance with claim 37, wherein the living species includes a zebrafish larva.

40. A system for analyzing neuropharmacology of a drug in accordance with claim 22, wherein the plurality of known drugs include central nervous system drugs or agents.

41. A system for analyzing neuropharmacology of a drug in accordance with claim 22, wherein the chemical compound includes a neuroactive compound.

* * * * *